United States Patent
Ravindranath et al.

(10) Patent No.: US 6,218,166 B1
(45) Date of Patent: Apr. 17, 2001

(54) ADJUVANT INCORPORATION INTO ANTIGEN CARRYING CELLS: COMPOSITIONS AND METHODS

(75) Inventors: Mepur H. Ravindranath, Los Angeles; Donald L. Morton, Malibu, both of CA (US)

(73) Assignee: John Wayne Cancer Institute, Santa Monica, CA (US)

( * ) Notice: Subject to any disclaimer, the term of this patent is extended or adjusted under 35 U.S.C. 154(b) by 0 days.

(21) Appl. No.: 08/462,106

(22) Filed: Jun. 5, 1995

Related U.S. Application Data

(63) Continuation-in-part of application No. 08/353,549, filed on Dec. 9, 1994, now abandoned.

(51) Int. Cl.$^7$ .......................... A61K 39/00; A61K 45/00; A61K 39/40; A61K 39/395

(52) U.S. Cl. ..................................... 435/240.2; 424/240.1; 424/277.1; 424/283.1; 424/184.1; 424/78.31; 424/278.1; 424/179.1; 424/174.1; 424/150.1; 424/201.1

(58) Field of Search ............................ 424/240.1, 277.1, 424/283.1, 184.1, 78.31, 278.1, 179.1, 150.1, 201.1, 174.1; 435/240.2

(56) References Cited

U.S. PATENT DOCUMENTS

| | | | |
|---|---|---|---|
| 4,435,386 | 3/1984 | Ribi et al. ........................... | 424/177 |
| 4,436,727 | 3/1984 | Ribi ..................................... | 424/177 |
| 4,436,728 | 3/1984 | Ribi et al. ........................... | 424/177 |
| 4,505,899 | 3/1985 | Ribi et al. ........................... | 514/8 |
| 4,505,900 | 3/1985 | Ribi et al. ........................... | 514/2 |
| 4,520,019 | 5/1985 | Ribi et al. ........................... | 424/195.1 |
| 4,579,945 | 4/1986 | Schwartzman et al. ............ | 336/127 |
| 4,629,722 | 12/1986 | Ribi .................................... | 514/2 |
| 4,844,894 | 7/1989 | Ribi .................................... | 424/8 |
| 4,866,034 | 9/1989 | Ribi .................................... | 514/2 |
| 4,877,611 | 10/1989 | Cantrell ............................... | 424/88 |
| 4,950,645 | 8/1990 | Vosika et al. ....................... | 514/8 |
| 4,987,237 | 1/1991 | Myers et al. ........................ | 549/222 |
| 5,102,663 | 4/1992 | Livingston et al. ................. | 424/88 |
| 5,290,551 | 3/1994 | Berd .................................... | 424/88 |
| 5,312,620 | 5/1994 | Ribi .................................... | 424/78.31 |
| 5,840,317 | * 11/1998 | Morton . | |
| 5,882,654 | * 3/1999 | Morton . | |
| 5,993,828 | * 11/1999 | Morton . | |
| 6,075,134 | * 6/2000 | Bertozzi et al. . | |

FOREIGN PATENT DOCUMENTS

WO 91/16347  10/1991  (WO) .

OTHER PUBLICATIONS

Seigler et al, Ann. Surg. 190/3:366–372, 1979.*
Eisenthal et al, 1993, Cancer Immunol Immunother 36:300–306.*
Isuchida et al, 1989, New Horizons of Tumor Therapy, pp315–324.*
Gillette et al, 1976 Int. J. Cancer 18: 216–222.*
Longnecker et al, 1993, Annals of N Y Acad Sciences 690:276–291.*
Ravindranath et al, 1991, Int'l Rev. Immunol 7: 303–329.*
Fisher et al, 1981, Surgical Clin. NorthAm. 61(6):1267–77.*
Livingston et al, 1983. Int. J. Cancer 31:567–75.*
Slingluff et al. 1988. J. Surgical Oncol. 39: 139–147.*
Weisenberger et al, 1982. J. Biol. Resp. Modifers 1:57–66.*
Elias et al 1992, J. Surgical Oncology 50:144–148.*
Bystryn 1990. Cancer & Metastases Rev. 9:81–91.*
Ramakrishma et al, 1993 Cancer Immunol Immunother 36:293–299.*
Kuus–Reichel et al, 1994. Hybridoma 13(1):31–36.*
Reintgenatal, 1991, Seminars in Surg. Oncol. 7:192–198.*
Eggers et al 1985, Cancer Immunol Immunother. 19:43–45.*
Laucius et al, 1977. Cancer 40:2091–93.*
Jensen et al, 1988. APMIS, 96:257–264.*
Pardoll et al, 1993, Immunol Today. 14(6):310–316.*
Semann 1987. Eds Kallman In: Rodent Tumor Models in Expt'al CancerTherapy pp 12–15 Pergamon Press NY.*
Kaiser et al, 1981, Surg. Clin. of NorthAm. 61(6):1249–57.*
Eilber et al, 1988, Am. J. Clin. Oncol. 11(1):39–45.*
Mitchell et al 1988, Cancer Res. 48:5883–5893.*
Barth et al, 1995, Cancer, 75:726–734.*
Hodge 1996, Cancer Immunol. Immunother. 43:127–134.*
Galligioni et al, 1993, Ann. NY Acad. Sci. 690:367–369.*
Sanderson et al, 1974. Nature, 248:690–691.*
Revesz. 1960, Cancer Res. 60:443–451.*
Baker et al., "Ability of Monophosphoryl Lipid A to Augment the Antibody Response of Young Mice," *Infection and Immunity*, 56(12):3064–3066, 1988.*
Baker et al., "Inactivation of Suppressor T–Cell Activity by Nontoxic Monophosphoryl Lipid A," *Infection and Immunity*, 56(5):1076–1083, 1988.*
Baker et al., "Enrichment of Suppressor T Cells by Means of Binding to Monophosphoryl Lipid A," *Infection and Immunity*, 58(3):726–731, 1990.*
Baker et al., "Structural Features That Influence the Ability of Lipid A and Its Analogs To Abolish Expression of Suppressor T Cell Activity," *Infection and Immunity*, 60(7):2694–2701, 1992.*

(List continued on next page.)

*Primary Examiner*—Nita Minnifield
(74) *Attorney, Agent, or Firm*—Fulbright & Jaworski LLP

(57) ABSTRACT

Disclosed are compositions and methods for enhancing the antibody and T cell response to cellular antigens by incorporating an immunopotentiating agent into the cellular membrane or into an intracellular compartment. Such adjuvant-incorporated cell compositions are useful in methods to increase immune responses against antigens, including immunologically cryptic tumor cell antigens, and may be employed to generate useful diagnostic antibodies, to elicit anti-tumor effects in immunized animals, and to significantly prolong survival in animals with cancer.

103 Claims, 23 Drawing Sheets

OTHER PUBLICATIONS

Baker et al., "Molecular Structures That Influence the Immunomodulatory Properties of the Lipid A and Inner Core Region Oligosaccharides of Bacterial Lipopolysaccharides," *Infection and Immunity,* 62(6):2257–2269, 1994.*

Banerji et al., "Membrane Lipid Composition Modulates the Binding Specificity of a Monoclonal Antibody Against Liposomes," *Biochimica et Biophysica Acta.,* 689:319–326, 1982.*

Brade et al., "An Artificial Glycoconjugate Containing the Bisphosphorylated Glucosamine Disaccharide Backbone of Lipid A Binds Lipid A Monoclonal Antibodies," *Infection and Immunity,* 61(10):4514–4517, 1993.*

Bystryn et al., "Immunogenicity of a Polyvalent Melanoma Antigen Vaccine in Humans," *Cancer,* 61:1065–1070, 1988.*

Chase et al., Effect of Monophosphoryl Lipid A on Host Resistance to Bacterial Infection, *Infection and Immunity,* 53(3):711–712, 1986.

Chen et al., "Activation of Macrophages From Aging Mice by Detoxified Lipid A," *Journal of Leukocyte Biology,* 49:416–422, 1991.

Cho et al., "Antitumor effect of monophosphoryl lipid A, polyadenylic–polyuridylic acid and cisplatin on B16 melanoma–induced pulmonary metastasis in mice," *Journal of the Korean Society for Microbiology,* 29(2):231–244, 1994.

Elliott et al., "The D–Galactosamine Loaded Mouse and Its Enhanced Sensitivity to Lipopolysaccharide and Monophosphoryl Lipid A: A Role for Superoxide," *Journal of Immunotherapy,* 10:69–74, 1991.

Fitzgerald, "Syphilis vaccine: up–regulation of immunogenicity by cyclophosphamide, Ribi adjuvant, and indomethacin confers significant protection against challenge infection in rabbits," *Vaccine,* 9:265–271, 1991.

Garg & Subbarao, "Immune Response of Systemic and Mucosal Lymphoid Organs to Pnu–Immune Vaccine as a Function of Age and the Efficacy of Monophosphoryl Lipid A as an Adjuvant," *Infection and Immunity,* 60(6):2329–2336, 1992.

Grabarek et al., "Endotoxic Lipid A Interaction with Human Platelets," *The Journal of Biological Chemistry,* 265(14):8117–8121, 1990.

Hraba et al., "The Influence of Monophosphoryl Lipid A (MPL™) on Erythrocyte Autoantibody Formation," *Immunobiol.,* 189:448–456, 1993.

Johnson et al., "Structural Characterization of Monophosphoryl Lipid A Homologs Obtained from *Salmonella minnesota* Re595 Lipopolysaccharide," *The Journal of Biological Chemistry,* 265(14):8108–8116, 1990.

Johnston & Bystryn, "Effect of Cell Wall Skeleton and Monophosphoryl Lipid A Adjuvant on the Immunogenicity of a Murine B16 Melanoma Vaccine," *Journal of the National Cancer Institute,*83(17):1240–1245, 1991.

Kuhn et al., "Characterization of the Epitope Specificity of Murine Monoclonal Antibodies Directed Against Lipid A," *Infection and Immunity,* 60(6):2201–2210, 1992.

Livingston et al., "The Serologic Response to Meth A Sarcoma Vaccines after Cyclophosphamide Treatment is Additionally Increased by Various Adjuvants," *The Journal of Immunology,* 135(2):1505–1509, 1985.

Masihi et al., "Effects of Nontoxic Lipid A and Endotoxin on Resistance of Mice to *Toxoplasma gondii*," *Journal of Biological Response Modifiers,* 7:535–539, 1988.

Mitchell et al., "Active–Specific Immunotherapy for Melanoma," *Journal of Clinical Oncology,* 8(5):856–869, 1990.

Morton & Ravindranath, "Active Specific Immunotherapy with Vaccines," *Cancer Medicine,* 3rd Ed., Holland et al., Lea & Febiger, Philadelphia, Section XVIII–2, pp. 913–926, 1993.

Morton et al., "Polyvalent Melanoma Vaccine Improves Survival of Patients with Metastatic Melanoma," *Annals of the New York Academy of Sciences, Specific Immunotherapy of Cancer with Vaccines,* 690:120–134, 1993.

Morton et al., "Tumor Gangliosides as Targets for Active Specific Immunotherapy of Melanoma in Man," *Biological Function of Gangliosides,* Svennerholm et al., Elsevier, Amsterdam, Ch. 19, pp. 250–275, 1994.

Myers et al., "Monophosphoryl Lipid A Behaves as a T–Cell–Independent Type 1 Carrier for Hapten–Specific Antibody Responses in Mice," *Infection and Immunity,* 63(1):168–174, 1995.

Qureshi & Takayama, "Purification and Structural Determination of Nontoxic Lipid A Obtained from the Lipopolysaccharide of *Salmonella Typhimurium,*" *The Journal of Biological Chemistry,* 257(19):11808–11815, 1982.

Rabinovich et al., "Vaccine Technologies: View to the Future," *Science,* 265:1401–1404, 1994.

Ravindranath et al., "Attachment of Monophosphoryl Lipid A (MPL) to Cells and Liposomes Augments Antibody Response to Membrane–bound Gangliosides," *Journal of Autoimmunity,* 7:803–816, 1994.

Ravindranath et al., "Efficacy of tumor cell vaccine after incorporating monophosphyoryl lipid A (MPL) in tumor cell membranes containing tumor–associated ganglioside," *Experientia,* 50:648–653, 1994.

Ravindranath et al., "Factors affecting the fine specificity and sensitivity of serum antiganglioside antibodies in ELISA," *Journal of Immunological Methods,* 169:257–272, 1994.

Ribi, "Beneficial Modification of the Endotoxin Molecule," *Journal of Biological Response Modifiers,* 3:1–9, 1984.

Rudbach et al., "Immunotherapy with Bacterial Endotoxins," *Adv. Exp. Med. Biol.,* 256:665–676, 1990.

Schuster et al., "Production of Antibodies Against Phosphocholine, Phosphatidylcholine, Sphingomyelin, and Lipid A by Injection of Liposomes Containing Lipid A," *The Journal of Immunology,* 122(3):900–905, 1979.

Takada et al., "Molecular and Structural Requirements of a Lipoteichoic Acid from *Enterococcus hirae* ATCC 9790 for Cytokine–Inducing, Antitumor, and Antigenic Activities," *Infection and Immunity,* 63(1):57–65, 1995.

Tanamoto, "Free Hydroxyl Groups are not Required for Endotoxic Activity of Lipid A," *Infection and Immunity,* 62(5):1705–1709, 1994.

Tanamoto, "Dissociation of Endotoxin Activities in a Chemically Synthesized Lipid A Precursor after Acetylation," *Infection and Immunity,* 63(2):690–692, 1995.

Verma et al., "Adjuvant Effects of Liposomes Containing Lipid A: Enhancement of Liposomal Antigen Presentation and Recruitment of Macrophages," *Infection and Immunity,* 60(6):2438–2444, 1992.

Vosika et al., "Phase–I study of intravenous modified lipid A," *Cancer Immunol. Immunother.,* 18:107–112, 1984.

Ravindranath et al., "An Epitope Common to gangliosides O–Acetyl–$G_{D3}$ and $G_{D3}$ Recognized by Antibodies in Melanoma Patients after Active Specific Immunotherapy," *Cancer Research,* 49:3891–3897, Jul. 1989.

Zhang et al., "Immune Sera and Monoclonal Antibodies Define Two Configurations for the Sialyl Tn Tumor Antigen," *Cancer Research,* 55:3364–3368, Aug. 1995.

PCT International Search Report, mailed Apr. 23, 1996.

* cited by examiner

ADJUVANT INCORPORATION INTO ANTIGEN CARRYING CELLS: COMPOSITIONS AND METHODS

The present application is a continuation-in-part of U.S. patent application Ser. No. 08/353,549, filed Dec. 9, 1994 (now abandoned), the entire text and figures of which disclosure is specifically incorporated herein by reference without disclaimer. The U.S. Government owns rights in the present invention pursuant to grant number PO1 CA12582 from the National Institutes of Health.

BACKGROUND OF THE INVENTION

I. Field of the Invention

The present invention relates generally to the fields of antigens, antibodies and adjuvants. The invention particularly provides for the generation of enhanced immune responses by associating or incorporating an immunopotentiating agent onto a natural cellular membrane or into an intracellular compartment. In a specific instance, the invention is exemplified by incorporating an adjuvant, such as a lipopolysaccharide-like adjuvant, into tumor cells and onto their outer membranes.

II. Description of the Related Art

Methods for manipulating the immune system to achieve a desired effect have been known for many years, and are used both in the prevention and therapy of disease and in immunization protocols to generate specific antibodies for other uses, e.g., in diagnostics. However, generating an appropriate immune response is not always a straightforward matter. Particular problems arise with antigens that are "immunologically cryptic", in which cases the immune responses are often too weak to be of practical use.

The problems associated with generating immune responses apply to a wide range of clinical and laboratory protocols, with one of the most important areas being that of cancer treatment and therapy. Various modalities of therapy have been used during the past 30 years to treat cancer, including radiation and chemotherapy, radical surgery and immunologically-based protocols. The generation of immune responses to isolated tumor antigens using microbial adjuvants has also been described (U.S. Pat. No. 4,877,611). Melanoma cell vaccines using shed antigens are available (e.g., U.S. Pat. No. 5,194,384; Bystryn et al., 1988; Livingston et al., 1987a). However, this has certain limitations and melanoma still poses a significant health problem worldwide (Elder et al., 1995).

Portoukalian (1978) recognized the importance of gangliosides as tumor-associated antigens in human melanoma. Since this work, interest in the biochemical and immunological characteristics of tumor-related gangliosides has increased. Essentially, gangliosides are glycolipids containing sialic acids and are important membrane bound components of normal and neoplastic cells (Portoukalian, 1978). Immunologically, they are recognized as T-cell independent antigens (Hardings et al., 1991; Ishioka et al., 1992; Freimer et al., 1993) and suppressors of cellular immune functions (Kawaguchi et al., 1989; Morrison et al., 1989; Miller & Esselman, 1975; Lengle et al., 1979; Whisler & Yates, 1980; Prokazova et al., 1988; Portoukalian, 1989; Hoon et al., 1988; Chu & Sharom, 1993).

Solid tumors of neuroectodermal origin produce and shed large quantities of immunosuppressive sialoglycolipids or gangliosides (Ravindranath & Morton, 1991). Human cutaneous malignant melanoma expresses gangliosides $GM_3$, $GD_3$, $GM_2$, $GD_2$ and $O-AcGD_3$ (Ravindranath & Irie, 1988), whereas B-16 murine melanoma expresses only $GM_3$ (Takahashi et al., 1988). The shedding of gangliosides by solid tumors leads to significantly elevated levels of gangliosides in the sera of cancer patients, as compared to normal subjects (Kloppel et al., 1977; Horgan, 1982; Katopodis et al., 1982; Munjal et al., 1984; Dwivedi et al., 1990; Tautu et al., 1988).

Intraperitoneal administration of $GM_3$ into the B16 melanoma-bearing mice has been reported to significantly augment melanoma growth, suggesting that $GM_3$ shed from tumor cells may favor tumor growth, possibly by suppressing immune-surveillance (Takahashi et al., 1988). In support of this observation, it has also been demonstrated that $GM_3$ preferentially suppresses the generation and activity of the cytotoxic lymphocytes in tumor bearing mice, suggesting that melanoma-derived $GM_3$ in circulation may impede antitumor functions of the immune system. $GM_3$ has also been found to be immunosuppressive in humans (Hachida et al., 1993; 1994).

Although anti-ganglioside antibodies are recognized as naturally occurring autoantibodies (Gillard et al., 1989), their level remains low even after repeated immunizations with purified gangliosides (Bogoch, 1960). Several investigators have attempted to induce antibody response to gangliosides by admixing gangliosides with foreign carrier proteins. These include, amongst others, pig serum (Rapport & Graf, 1969; Sherwin et al., 1964); serum albumin (Pascal et al., 1966; Koscielak et al., 1968); human erythrocyte glycoprotein (Naiki et al., 1974); foreign erythrocytes (Yokoyama et al., 1963); and a mixture of meningococcal outer membrane proteins, cationized bovine serum albumin, multiple antigenic peptides, polylysine and keyhole limpet (molluscan) hemocyanin (Helling et al., 1993).

The use of non-toxic microbial adjuvants with isolated and purified tumor-associated antigens was described in U.S. Pat. No. 4,877,611. The use of bacterial carriers, such as *Salmonella Minnesota* or *Mycobacterium bovis* (Livingston et al., 1987a; U.S. Pat. No. 5,102,663) has also been reported to augment antibody response against gangliosides in human and in murine studies. However, $GM_3$ bound to cell membranes in humans (Livingston et al., 1987b), and purified and free GM3 in mice (Livingston et al., 1987a), induced poor antibody responses. It has not been established whether the failure to induce antibody responses is due to crypticity of the antigen or failure to be recognized by the antigen presenting system.

It has been shown that attaching lipopolysaccharide (LPS) and lipid A to synthetic membranes (liposomes) can result in the generation of an immune response to membrane components. This has been proposed to be connected with macrophage recruitment (Verma et al., 1992). Research has shown that immunization of mice with lipid A-attached liposomes induced antibody against components of the liposomes, whereas liposomes without lipid A failed to elicit any response (Schuster et al., 1979; Banerji et al., 1982; Verma et al., 1992). Recently, Freimer et al. (1993) have also studied the T-cell independent antibody response to purified gangliosides using lipid A as an adjuvant. However, the use of lipid A as an immunological adjuvant in humans is precluded by the toxicity of lipid A.

Monophosphoryl lipid A (MPL) is a nontoxic derivative of lipid A from Salmonella (Qureshi et al., 1985; Ribi, 1984; Johnson et al., 1987). MPL has comparable biological activities to lipid A, including B cell mitogenicity, adjuvanticity, activation of macrophages and induction of interferon synthesis (Ribi et al., 1984, 1986; Verma et al., 1992). Johnston & Bystryn (1991) tested the combined effect of mycobacterial cell wall skeleton and MPL on a melanoma vaccine of murine B16 cells. Unfortunately, MPL was not found to potentiate tumor-protective immunity in these studies (Johnston & Bystryn, 1991).

Livingston et al. (1987a) have tested the usefulness of MPL in augmenting anti-ganglioside antibodies, using purified gangliosides and ganglioside-liposomes. However, the Livingston et al. group prefer to use whole Salmonella as an adjuvant, as shown in their subsequent studies in U.S. Pat. No. 5,102,663. In U.S. Pat. No. 5,312,620, a complex system of polymeric adjuvants incorporated into lipid layers is described. The adjuvants are first conjugated to a polymerizable group and then co-polymerized with a water-soluble and/or amphiphilic polymerizable monomer or combined with a polymerized amphiphile.

Despite the continuing efforts in this field, it is apparent that improved methods and novel strategies for generating immune responses are still needed. Simple methods that are appropriate for use with a wide variety of antigens are particularly desirable. The development of a method by which to improve the immune response against immunologically cryptic antigens would represent a significant advance, particularly if such a method was adaptable for use against clinically relevant antigens.

SUMMARY OF THE INVENTION

The present invention seeks to overcome these and other drawbacks inherent in the prior art by providing improved immunogenic compositions in which an adjuvant is incorporated into an intracellular compartment of, or incorporated onto or conjugated to, the outer membrane of an intact cell. Using such compositions, significantly improved immune responses are evoked. The invention may be employed to stimulate or increase the antibody or T cell responses against intracellular or membrane-bound antigens, even those that are otherwise poor immunogens. The invention also provides for the orchestration of cytokines in order to stimulate and activate cellular elements of the immune system.

Antibodies and T cells generated using the invention may be isolated from an animal and used in other methods, such as, particularly, using antibodies in a variety of diagnostic tests. Equally, the antibodies and T cells may continue to circulate in the animal in order to provide beneficial therapeutic effects.

In certain embodiments the invention concerns compositions, including pharmacologically acceptable formulations, that comprise one or more cells, or a population of cells, where the cells include one or more adjuvants associated with the cell surface or with an intracellular compartment. These compositions are referred to herein as adjuvant-conjugated cells or cellular complexes, adjuvant-incorporated cells or complexes, adjuvant-associated cells or complexes, or simply, "adjuvant-cell compositions".

Cells including one or more adjuvants "associated" with the cell surface, as used herein, means that the adjuvants are incorporated into or onto the membrane, conjugated to a membrane component, or otherwise physically and functionally associated with the intact membrane of a cell. The "physical and functional" association of the adjuvant with the membrane will be such that the adjuvant remains in contact with the membrane under physiological conditions in an amount effective to increase the immune response against cellular antigens present in the same membranous environment.

Cells including one or more adjuvants associated with "an intracellular compartment" means that the adjuvants are incorporated intracellularly, so that they are physically and functionally associated with an intracellular compartment of an intact cell. The adjuvants may be in contact with or located within any of the intracellular areas, including the cytoplasm, nucleus, golgi, endocytoplasmic reticulum, endocytotic vesicles and intracellular membrane surfaces, and also the mitochondria, ribosomes and other intracellular structures. The adjuvants will be present in amounts effective to increase the immune response against intracellular antigens of the cell, probably via processing and co-presentation of the adjuvant and intracellular antigen at the cell membrane.

The use of whole cells is an important feature of the invention that imparts many particular advantages. For example, tumor-associated antigens (TAAs) no longer have to be first identified or purified. omitting the purification step is a marked improvement in terms of time, difficulty and costs and, even more importantly, ensures that the antigens are presented in their natural environment. Isolation of TAAs has previously involved harsh conditions, such as extraction in 3 M KCl, which may destroy or modify certain of the epitopes. However, any extraction method that removes the TAA from the membrane environment is likely to alter its immunogenic properties, and it is an advantage of the present invention that this is no longer necessary.

The use of adjuvant-incorporated whole cells has the further advantages that the adjuvants are functionally associated with the antigens in the same membranous environment. This represents a more physiological-like situation over the general antigen-adjuvant admixtures used previously. As the immune system typically "sees" antigens presented at the surface of cells, incorporating the adjuvants into intact antigen-expressing cells more closely mimics host antigen presentation and will provide enhanced benefit to the animal.

The adjuvant-incorporated cell methodology of the invention has the further advantages that it is easier to generate immune responses against immunologically cryptic antigens. It is also simple, cost-effective, reproducible, and readily adaptable for use with any cell type. When administered to a human subject, it is also expected that the adjuvant-incorporated whole cells will prove effective at considerably lower doses with respect to the adjuvant itself. For example, in terms of MPL, it is contemplated that an effective response will result using MPL in the nanogram range, rather than the microgram range, such as the 10–500 $\mu$gs proposed in U.S. Pat. No. 4,877,611.

As the present invention allows for the intracellular incorporation of adjuvants, it is also useful for generating or increasing immune responses against intracellular antigens. This is particularly advantageous as various tumor-associated antigens are intracellular. Numerous other antigens have intracellular locations, including various nuclear proteins, and even DNA, that are, for example, associated with certain autoimmune diseases.

The present invention provides a simple, but surprisingly effective method of preparing an adjuvant-incorporated cell complex, which method comprises incubating cells in an adjuvant-suspended culture media at an appropriate temperature and for a sufficient period of time, for example, as described herein in Example 5 and Example 8. The adjuvant-cell compositions of the invention, as exemplified by MPL-melanoma cell compositions, generally include between about 0.4 ng adjuvant, e.g., MPL, and about 3.1 ng adjuvant per $10^6$ cells; with levels of between about 1.6 ng adjuvant, e.g., MPL, and about 2.4 ng adjuvant per $10^6$ cells being routinely achieved.

The cell surface-associated adjuvants may be conjugated to any available membrane component, as exemplified by proteins, glycolipids and phospholipids in the membrane bilayer. Data is presented herein to show that the adjuvant-incorporated cells of the invention have adjuvants incorporated into the bilayer, and are not simply cells coated with, or loosely associated with, adjuvants. The adjuvant-incorporated cells of the invention are associated with effective amounts of adjuvants and yet the integrity of the cell is maintained.

Those working in the field of adjuvant compositions and their uses have previously experienced several difficulties due to the chemical properties of the adjuvants. For example, as certain adjuvants, such as MPL, are amphipathic they are difficult to solubilize in aqueous media. Furthermore, where adjuvants are intended for use in humans, which is usually the case, the use of many typical laboratory solvents, such as triethylamine or triethanolamine, and other liquids is not appropriate. The present inventors have discovered that such difficulties can be overcome by incubating the cells in an adjuvant-suspended culture media.

The "adjuvant-suspended culture media" of the invention are media, preferably, pharmacologically-acceptable media, that have been manipulated to contain higher amounts of one or more available adjuvants than normal. Particularly, the adjuvant-suspended culture media are capable of containing amphipathic adjuvants at levels higher than their normal solubility in aqueous media would suggest, and in a form so that they are "available" for conjugation to or association with the membrane of a cell, or for incorporation into an intracellular compartment. One advantageous manner of achieving this is to use one or more sonication cycles, as disclosed herein in Example 5.

The cellular components may be animal or human cells of virtually any type. Certain examples are cells infected with a virus that expresses a viral antigen at the cell surface and, also, tumor cells. Cells that secrete cytokines, or that are capable of secreting cytokines in response to certain stimuli, or cells that have been rendered capable of secreting cytokines due to genetic manipulation, i.e., altered by the hand of man, are also contemplated for use herewith. The use of cells that are capable of secreting cytokines and that also include one or more tumor-associated antigens in their membrane is also contemplated.

The use of tumor cells is preferred in certain cases. If desired, irradiated tumor cells may be employed to avoid significant adverse effects on the animal receiving the cells. Of course, irradiated tumor cells should always be employed in connection with human administration. The tumor cells may be irradiated prior to adjuvant conjugation, however, it is currently preferred that they be irradiated subsequent to the adjuvant conjugation process. Of course, irradiation could take place at any point of the preparative methods, or at several points.

A list of exemplary tumor cell lines is included herein, along with the corresponding ATCC designation numbers (Table 2 and Table 3). The cells in Table 3 will be preferred in certain embodiments. Tumor cells that have previously been used in animal studies or clinical trials will also be preferred, and any cell lines approved for human administration by the FDA will be particularly preferred.

Of course, other cells that have a particular antigen inserted into the membrane may also be used. This includes antigens physically mixed into or conjugated to the membrane, those incorporated following phagocytosis, and those expressed by the cell following insertion of a coding DNA segment into the cell ("recombinant cells"). In such ways, any antigen, such as a tumor antigen, may be expressed as the predominant antigen in a cell type that it is not normally associated with.

Cells that have been manipulated to incorporate other molecules in the membrane, such as additional targets or immunologically relevant molecules, may also be used. These include additional non-adjuvant protein components mixed into the membrane and molecules expressed by a cell following introduction of a coding DNA segment into the cell. Additional or different MHC class I or MHC class II antigens may thus be expressed in cells. It is particularly contemplated that a target molecule be included in the cell membrane to increase subsequent adjuvant-cell mediated or other host reactions against diseased cells of the animal. A currently preferred example is the addition of fibronectin in combination with an adjuvant to irradiated bladder cancer cells for use in bladder cancer treatment.

Tumor cells that express ganglioside antigens are a particular example of cells currently preferred for use in the present invention. Melanoma cells, including both mouse and human melanoma cells, are exemplary cells that have ganglioside antigens. The mouse melanoma cells termed B16, and the human melanoma cells termed M27, M18, M14, M111, M22, M7, M102, M108, M16, M104, M109, M14, M7, M25, M24, M10 and M101 are exemplary cell types for use in this invention; with M14, M7, M24, M25, M10 and M101 being preferred in certain cases; and M25, M10 and M101 currently being most preferred.

Tumor cells that include an antigen associated with an intracellular compartment are also contemplated for use in the present invention. Examples of important tumor-associated intracellular adjuvants are described in Example 8.

Although an understanding of the physical and chemical processes that operate during the conjugation method is not necessary to practice the invention, it is currently proposed that adjuvants such as MPL may preferentially bind to certain membrane proteins, such as proteins that are capable of binding to fatty acids. As such, it is contemplated that cells exhibiting higher levels of fatty acid binding proteins may be identified, or even developed, for advantageous use with the present invention.

Erythrocytes are a further example of cells also preferred for use in the present invention. It is contemplated that autologous erythrocytes would be obtained, e.g., from a cancer patient, and manipulated to form an adjuvant-incorporated cell, as disclosed herein. Erythrocytes obtained from cancer patients are known to be coated with tumor-associated antigens and can thus be used to promote an anti-tumor response. The use of erythrocytes has several advantages in that they are plentiful, easily obtained, do not require culturing and are a nuclear.

Compositions in accordance with the invention may include various cell types, one or more of which may include one or more adjuvants associated with the cell surface or an intracellular compartment, whilst other cells of the same type or other distinct cell types present may have no additional adjuvant. Particularly, multiple different adjuvants may be incorporated into a single cell or into multiple different cells. All such variations are within the scope of the invention. The use of multiple non-cell-associated adjuvants is well established in the art and such multiplicity is presently contemplated for use with the adjuvant-incorporated cells of the invention.

Virtually any adjuvant may also be employed in this invention, so long as the adjuvant may be incorporated into an intracellular compartment, or incorporated onto, physically associated with, or conjugated to the cell membrane of the cell in question, as described above. The adjuvants may be provided as purified components, in a partially purified state, or even as a membrane preparation or cellular extract, so long as the active components of such compositions can be incorporated into the cell itself or associated with, integrated into, or conjugated to the membrane of the target cell. Using membrane preparations and cellular extracts is not considered to be a particular problem due to the physical properties of the adjuvants and the mechanisms of membrane integration.

Adjuvants may also be chosen according to their documented properties. For example, adjuvants that are known to have both antibody- and T cell-enhancing capabilities will be preferred in certain cases. Adjuvants that stimulate the production of one, or preferably, of more than one, cytokine will also be preferred, particularly those that activate cytokines that stimulate further anti-tumor processes, such as by activating cytotoxic T cells (CTLs), NK cells, and the like. Adjuvants that particularly assist in inducing IgM antibodies are also preferred for use in certain embodiments.

A list of exemplary adjuvants for use in the present invention can be found herein in Table 1. Technic acids from Gram -ve cells, such as LTA, RTA, GTA, and their synthetic counterparts, are one preferred group of adjuvants. Hemocyanins and hemoerythrins, such as KLH, are also preferred, as are chitin and chitosan.

Another preferred group of adjuvants are the muramyl dipeptide (MDP) and tripeptide peptidoglycans and their derivatives, such as threonyl-NDP, fatty acid derivatives, such as MTPPE, and the derivatives described in U.S. Pat. No. 4,950,645, incorporated herein by reference. BCG, BCG-cell wall skeleton (CWS) and trehalose monomycolate and dimycolate (U.S. Pat. Nos. 4,579,945 and 4,520,019, each incorporated herein by reference) may also be used as adjuvants in the invention, either singly or in combinations of two or three agents, or in combination with MPL.

Amphipathic and surface active agents, such as QS21, and nonionic block copolymer surfactant form yet another group of preferred adjuvants. Quil A and lentinen are also preferred. Each of the above are generally non-toxic adjuvants or adjuvants with reduced toxicity and are preferred for human administration.

A particularly preferred adjuvants are currently the lipopolysaccharide (endotoxin) group of adjuvants. This is exemplified by lipid A, which may be used in animals, and detoxified endotoxins, which may be used in animals and humans. Detoxified and refined endotoxins, and combinations thereof, are described in U.S. Pat. Nos. 4,866,034; 4,435,386; 4,505,899; 4,436,727; 4,436,728; 4,505,900.

Further preferred adjuvants are the bacterial superantigens. Although useful in all aspects of the invention, these adjuvants are particularly contemplated for use in generating or enhancing the immune response against intracellular antigens, including intracellular tumor antigens. Examples of bacterial superantigens include Staphylococcal enterotoxins, e.g., as produced by *S. aureus* and *S. epidermidis*; *E. coli* exotoxins, and other membrane proteins and toxins from bacteria such as *Clostridium perfringens* and *Streptococcus pyogenes*.

The non-toxic derivative monophosphoryl lipid A (MPL) is currently the most preferred adjuvant, as it has both antibody- and T cell-enhancing capabilities and because it induces IgM antibodies. MPL derivatives and synthetic MPLs, as described by Johnson et al. (1990), Grabarek et al. (1990), Baker et al. (1992; 1994); Tanamoto et al. (1994a;b; 1995); Brade et al. (1993) and U.S. Pat. No. 4,987,237, each incorporated herein by reference, form a particularly preferred group of adjuvants for incorporation into cells.

Adjuvants that do have certain toxic side effects may still be used in this invention, however, so long as their toxicity is monitored and kept within the limits generally known to acceptable as side effects. In experimental animals, these limits will be higher than in humans. Indeed, toxicity and other adverse effects are less problematic where animals are used, e.g., for the purposes of raising antibodies or T cells specific for a cellular antigen.

To prepare an adjuvant-incorporated cell composition in accordance with the present invention, one will generally first prepare an adjuvant-suspended composition, preferably by sonication, and then admix a composition of the cells with the adjuvant suspension. The admixture is then incubated at a suitable temperature and for a period of time to effect intracellularly incorporation or membrane conjugation. Exemplary suitable conditions are described herein in Example 5 and Example 8.

Although a wide variety of other conjugation methods are possible, using a sonication cycle to suspend an amphipathic adjuvant in an aqueous medium is most preferred as this is believed to result in amounts of adjuvant conjugated per cell that could not previously be achieved. Increasing the conjugation temperature above 4° C. is also preferred as this results in an increase of intracellular transport of the adjuvant, as shown in Example 8. Temperatures between about 10° C. and about 40° C. are preferred, with the physiological temperature of about 37° C. being most preferred for use with human cells.

The amount of adjuvant conjugated to a cell may generally be increased or maximized in order to optimize the immunopotential of the composition. As disclosed herein in Example 5 and Example 8, by way of example only, incubating cells with a sonicated MPL suspension at a level of about 75 $\mu$g of MPL per million cells results in levels of between about 0.4 ng and about 3.1 ng of cell surface-associated MPL per million cells.

The methods associated with the invention include methods for generating an antibody or a T cell response, which methods generally comprise administering to an animal an immunologically effective amount of an adjuvant-incorporated cell composition that includes at least one cell type that includes at least one adjuvant associated with the cell surface or with an intracellular compartment. Immunologically effective amounts are those amounts effective to stimulate cytokine production, or preferably, to stimulate an antibody or antigen-specific T cell response in the animal, as exemplified herein.

A sample or samples may subsequently be obtained from the animal to provide the desired antibodies or T cells. Blood samples are appropriate for obtaining polyclonal antibodies and less-purified T cells compositions, whereas spleen cells may be obtained to provide monoclonal antibodies and more purified T cell compositions. The methods for generating purified antibodies and T cells from such samples are well known to those of skill in the art, and are further described in the present disclosure.

The compositions administered to animals or humans in these methods may include additional components in combination with the adjuvant-incorporated cell compositions, such as immunologically effective amounts of purified antibodies, activated lymphocytes and/or other cells of a different or the same type. The cells may be obtained from the animal or human in question, e.g., allogenic tumor cells or erythrocytes. The lymphocytes may also be obtained from the animal or human in question and activated in vitro using known techniques.

The methods of the invention may be used, in certain circumstances, as therapy for diseases, such as cancer, where the stimulation of the immune system enhances the anti-tumor activity of the animal. As such, the invention also provides methods for stimulating therapeutic or otherwise beneficial immune responses in an animal with a disease, such as methods for stimulating an anti-tumor cell immunological response in an animal having any one of a variety of cancers. The MPL-incorporated cells of the invention may also be used to inhibit the onset of septicemia and endotoxemia, as described in U.S. Pat. No. 4,844,894.

These methods comprise, generally, administering to such an animal a pharmacologically-acceptable adjuvant-incorporated cell composition comprising cells that include a tumor antigen and that are manipulated to have one or more adjuvants associated with the cell surface or with an intracellular compartment. The cells are administered in an amount effective to stimulate an antibody or T cell response against the diseased cells of the animal. The tumor antigen-containing adjuvant-incorporated cell compositions may include irradiated tumor cells or erythrocytes, preferably those obtained from the animal to be treated. Currently, about 24 million adjuvant-incorporated melanoma cells are contemplated for use in melanoma therapy, with each cell containing at least about 1 ng of adjuvant or more. Any pharmacologically-acceptable medium may be used, as are widely available commercially.

Where tumor cells are used, they may be autologous tumor cells, i.e., obtained from the same animal or human patient that is to be treated and then inactivated outside the body. Alternatively, the tumor cells may be allogenic cells, in which case they will generally include an intracellular or membrane-bound tumor antigen that stimulates an antibody or T cell response against a tumor antigen of the tumor cells of the animal to be treated, i.e., they will be generally of the same tumor type and will stimulate a "cross-reactive" immune response.

The tumor antigen-containing adjuvant-incorporated cell compositions may be administered to an animal or patient by any acceptable method, including injection into the general circulation or injection into the tumor site. The administration of such cells, whether of human or animal origin, having adjuvants in their outer membranes may be used to achieve effective cancer therapy in human patients, as disclosed herein. Treatment methods of the invention may be used after, prior to, or in combination with other methods, such as, radiotherapy and chemotherapy. Pre-treatment with BCG (Bast et al., 1974; Bennet et al., 1988; Minden et al., 1976; Yamamoto et al., 1988) is contemplated to be particularly useful.

BRIEF DESCRIPTION OF THE DRAWINGS

FIG. 1A shoews anti-$GM_3$ antibodies; FIG. 1B shows anti-$GM_2$ antibodies; FIG. 1C shows anti-$GD_3$ antibodies; and FIG. 1D shows anti-$GD_2$ antibodies. Groups of three mice were injected with saline on day 0 and then treated with saline (Saline) or immunized with M25 tumor cells, with or without additional components. As shown, the treatment compositions were M25 tumor cells without any adjuvants (■); M25 tumor cells with lipopolysaccharide (LPS) attached (●); M25 tumor cells with Lipid A attached (▼); and M25 tumor cells with monophosphoryl lipid A (MPL) attached (♦) Saline control is also shown (○). Tumor cells were given on day 16 and day 35, as described in Example 2, first study. Both IgM and IgG antibodies were measured in the ELISA system. All ELISA absorbencies were corrected for background noise (O.D. of diluted sera from wells without antigen). The ELISA absorbencies of individual immunized mice were further corrected for the absorbency values obtained for the saline treated (sham control) mice injected with saline on days 0 and 14. Duplicate ELISA assays were performed for each sera. FIG. 1E shows the IgG response after the second immunization, which pattern was identical for all tested gangliosides. The ELISA absorbance is shown (y axis) versus the IgG antibody at a dilution of $1 \times 10^3$ (x axis). The IgM antibody titers of M25-MPL cells at 1:1000 or 1:2000 dilutions is significantly higher (p=0.001) than the titers obtained with adjuvant-free M25 cells at the corresponding dilutions.

FIG. 2A shows anti-phosphatidyl-serine antibodies; FIG. 2B shows anti-phosphatidyl ethanolamine; and FIG. 2C shows anti-phosphatidyl-choline. As shown, the treatment compositions were M25 tumor cells without any adjuvants (■); M25 tumor cells withlipopolysaccharide (LPS) attached (●); M25 tumor cells with Lipid A attached (▼); and M25 tumor cells with monophosphoryl lipid A (MPL) attached (♦). Saline cintrol is also shown (○). In contrast to anti-ganglioside antibodies, the IgM titer is <0.1. Non-parametric analyses between adjuvant (LPS/LA/MPL) coupled M25 cells and adjuvant free M25 cells at 1:1000 and 1:2000 dilution showed that the difference in the mean titers of different phospholipid antibodies between adjuvant attached and free groups at a dilution (1:1000 or 1:2000) were significant at p=0.05.

FIG. 7 also shows that better resolution of absorbencies was obtained at a concentration of 0.8 ng of MPL, showing that this concentration is suitable as a standard for routine ELISA by single-point quantitation assay. The ratios of antibody:MPL concentration shown in FIG. 7 are 1:1000 (□), 1:2000 (–), 1:4000 (♦) 1:8000 (●), 1:16000 (■), 1:32000 (○) and 1:64000 (◊).

FIG. 15A, Blank: cells without MPL, MAb 8A1 but stained with antibody coupled to the fluorescent dye fluorescein-isothiocyanate (FITC); the number of cells taking up the fluorescence are <20. FIG. 15B, Control: Cells without MPL but with MAb 8A1 and 2nd antibody coupled to FITC; the number of cells taking up the fluorescence are <70. FIG. 15C, Study: Cells incorporated with MPL and stained with MAb 8A1 and 2nd antibody coupled to FITC. The number of cells showing fluorescence are twelve fold greater than the control (n=<800). This provides direct evidence for the incorporation of MPL onto the tumor cell surface.

DETAILED DESCRIPTION OF THE PREFERRED EMBODIMENTS

I. Ganglioside Immunoreactivity

Figure 1A:
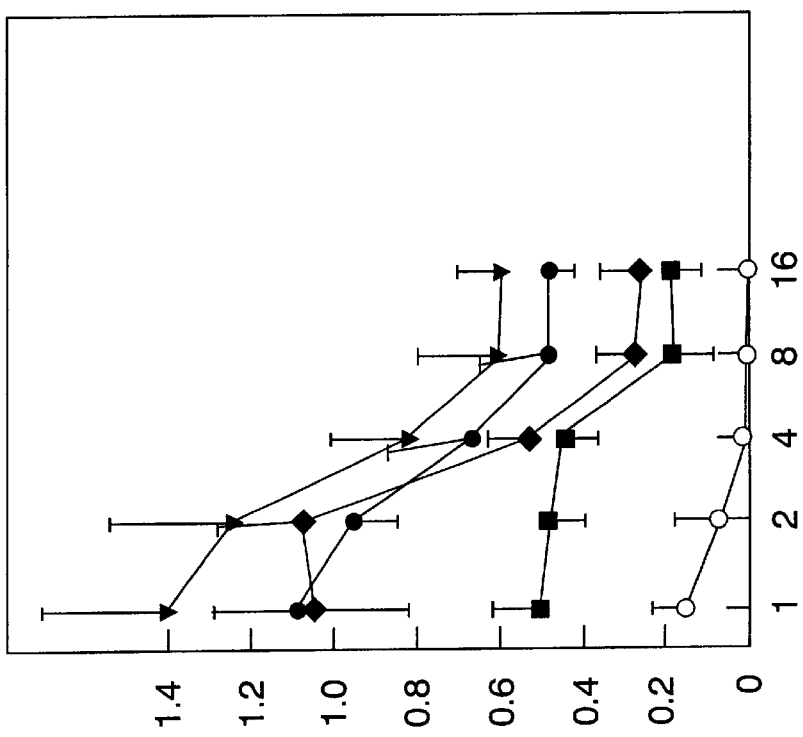
FIG. 1A, FIG. 1B, FIG. 1C, FIG. 1D and FIG 1E. Mean (±SD) ELISA absorbency (y axis) of anti-ganglioside antibodies after second immunization of M25 cells in BALB/c mice.
Figure 1B:
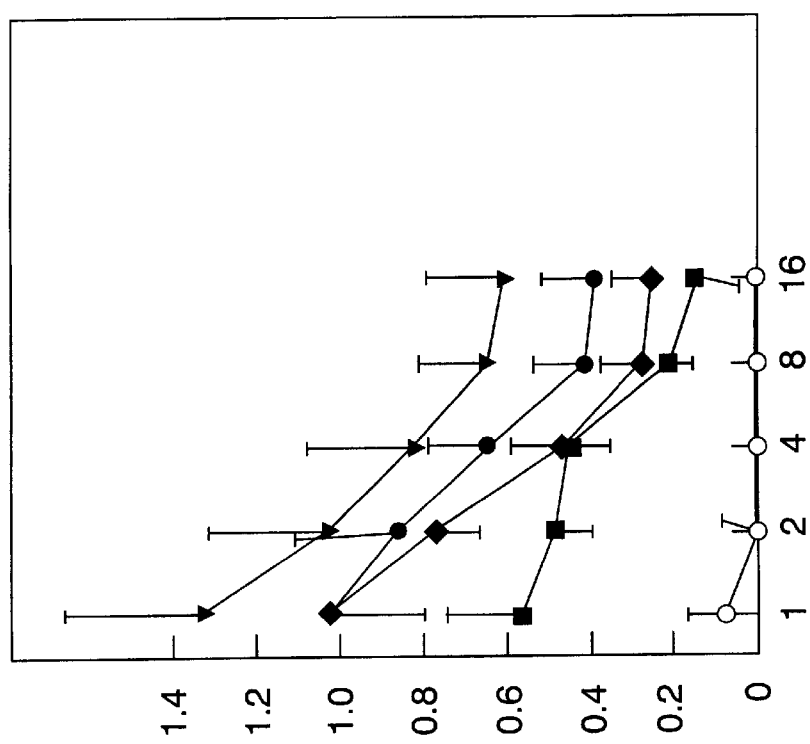
Figure 1C:
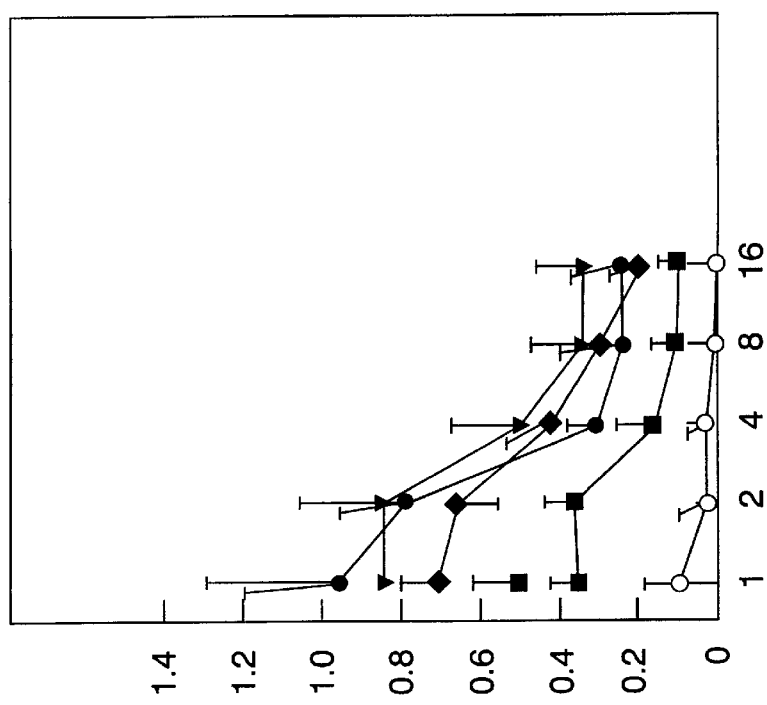
Figure 1D:
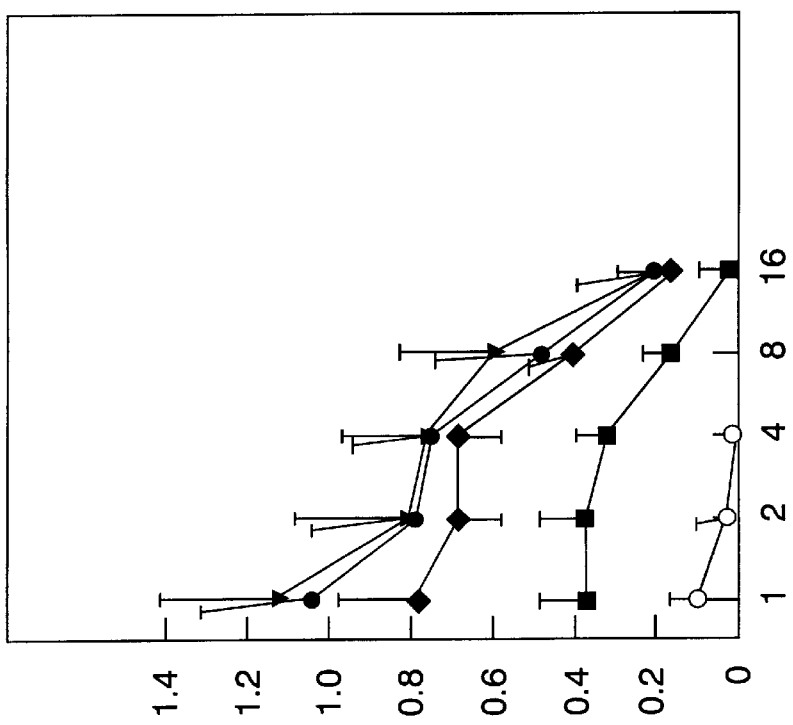
Figure 1E:
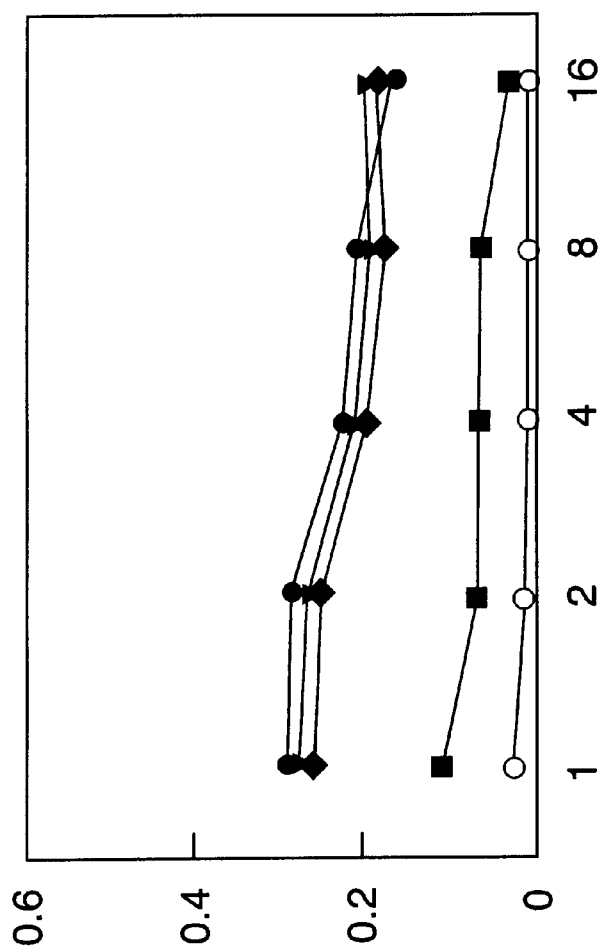

Tumor-associated gangliosides are expressed self-antigens in both animals and humans. GM$_3$ is expressed in murine melanoma (Hirabayashi et al., 1985), and GD$_3$, or GM$_2$, is expressed in human melanoma. Absent other phenomena, this selective expression would make melanoma-related gangliosides potential target antigens for immunotherapy (Ravindranath & Morton, 1991; Morton et al., 1994). Unfortunately, such gangliosides are known to be immunologically cryptic (Hirabayashi et al., 1985; Ravindranath & Morton, 1991; Ravindranath & Irie, 1988). Prior to the present invention, this property generally prevented the exploitation of gangliosides as target antigens.

Gangliosides are also known to suppress cellular immune functions (Kawaguchi et al., 1989; Morrison et al., 1989;

Miller & Esselman, 1975; Lengle et al., 1979; Whisler & Yates, 1980; Prokazova et al., 1988; Portoukalian, 1989; Hoon et al., 1988; Chu & Sharom, 1993). It has therefore been suggested that the increased level of circulating gangliosides in cancer patients might impair their antitumor immune response (Kloppel et al., 1977; Horgan, 1982; Katopodis et al., 1982; Munjal et al., 1984; Dwivedi et al., 1990; Tautu et al., 1988).

The inventors reasoned that immunocompetence may be restored in cancer patients, amongst others, by using anti-ganglioside antibodies to remove shed gangliosides from the circulation. However, the weak immunogenic nature of gangliosides (Bogoch, 1960; Rapport & Graf, 1969), again suggested that the generation of anti-ganglioside antibodies would not prove to be a clinically viable method. A novel means by which to increase the immunogenicity of gangliosides, making anti-cancer strategies feasible, was therefore developed by the inventors.

This invention is based upon the inclusion of an adjuvant into the same natural membranous environment as the antigen to which one desires to raise an antibody. This is particularly exemplified by including an adjuvant, or immunopotentiating agent, on the cell surface of a cancer cell to augment the immune response against cancer cell antigens. This method was found to be particularly successful in increasing the antibody response to ganglioside antigens and to have increased efficacy when compared to immunization with adjuvant-purified ganglioside preparations.

In particular, it was found that incorporating the adjuvant monophosphoryl lipid A (MPL) onto tumor cell membranes significantly augmented immune responses, as evidenced by the anti-ganglioside antibody response. Adding MPL to the membrane of both murine (B16) and human (M25) melanoma cells resulted in anti-ganglioside antibody responses of 1000-fold higher than previously reported to be possible using a wide range of ganglioside compositions. The MPL-tumor cell compositions were thus dramatically more effective than multiple large doses of gangliosides (Bogoch, 1960; Shy et al., 1989); gangliosides linked to whole bacteria Salmonella and Mycobacteria (Livingston et al., 1987a; 1987b; U.S. Pat. No. 5,102,663); gangliosides mixed with complete Freund's adjuvant (Naiki et al., 1974); gangliosides mixed with Freund's adjuvant together with pertussis vaccine (Yokoyama et al., 1963); and gangliosides with keyhole limpet hemocyanin (KLH) (Helling et al., 1993).

Furthermore, using this novel method, high anti-ganglioside antibody responses was obtained using a minimal immunization schedule (2 times) in contrast to 4 to 24 immunizations (Bogoch, 1960; Sherwin et al., 1964; Pascal et al., 1966; Koscielak et al., 1968; Naiki et al., 1974; Yokoyama et al., 1963; Helling et al., 1993; Portoukalian et al., 1991). Free gangliosides, or gangliosides coupled to MPL in micellar form, did not have this effect, even when the amount of free gangliosides (expressed as lipid-bound sialic acids) was more than 2.5 to 10 fold greater than that found on cell membranes. Previously, Bogoch (1960) used a 3000 fold higher dose of gangliosides to obtain an anti-ganglioside antibody response.

An important finding was that a high level of anti-ganglioside antibody was induced by two low doses of MPL-coupled B16 cells, containing only 600 nanograms of ganglioside, in contrast to MPL-liposomes, in which there is 16 $\mu$g of ganglioside. The antibody response obtained with MPL-attached cells is thus far superior than that observed after attaching MPL to the ganglioside containing liposomes, considering the 27-fold higher level of gangliosides in the liposomes (16 $\mu$g vs. 600 ng).

The inventors also show herein that the generation of antibodies in response to tumor-cell:adjuvant compositions correlates with increased anti-tumor effects in an established animal model of cancer. Studying the effects of treatment protocols on tumor cells, tumor size and overall survival in experimental animals in vivo is an effective means by which to assess new treatment compositions and methods. Such systems are widely employed and are known to be predictive of success in human treatment regimens. This is different to the problems encountered in other animal models, such as, for example models of AIDS.

The model used herein was particularly chosen because B16 melanoma expresses the ganglioside $GM_3$ as a melanoma-associated antigen. $GM_3$ is known to be immunosuppressive and to promote tumor growth, making it an important target and $GM_3$ is also found in human melanoma, making it even more useful as a model.

Figure 8:
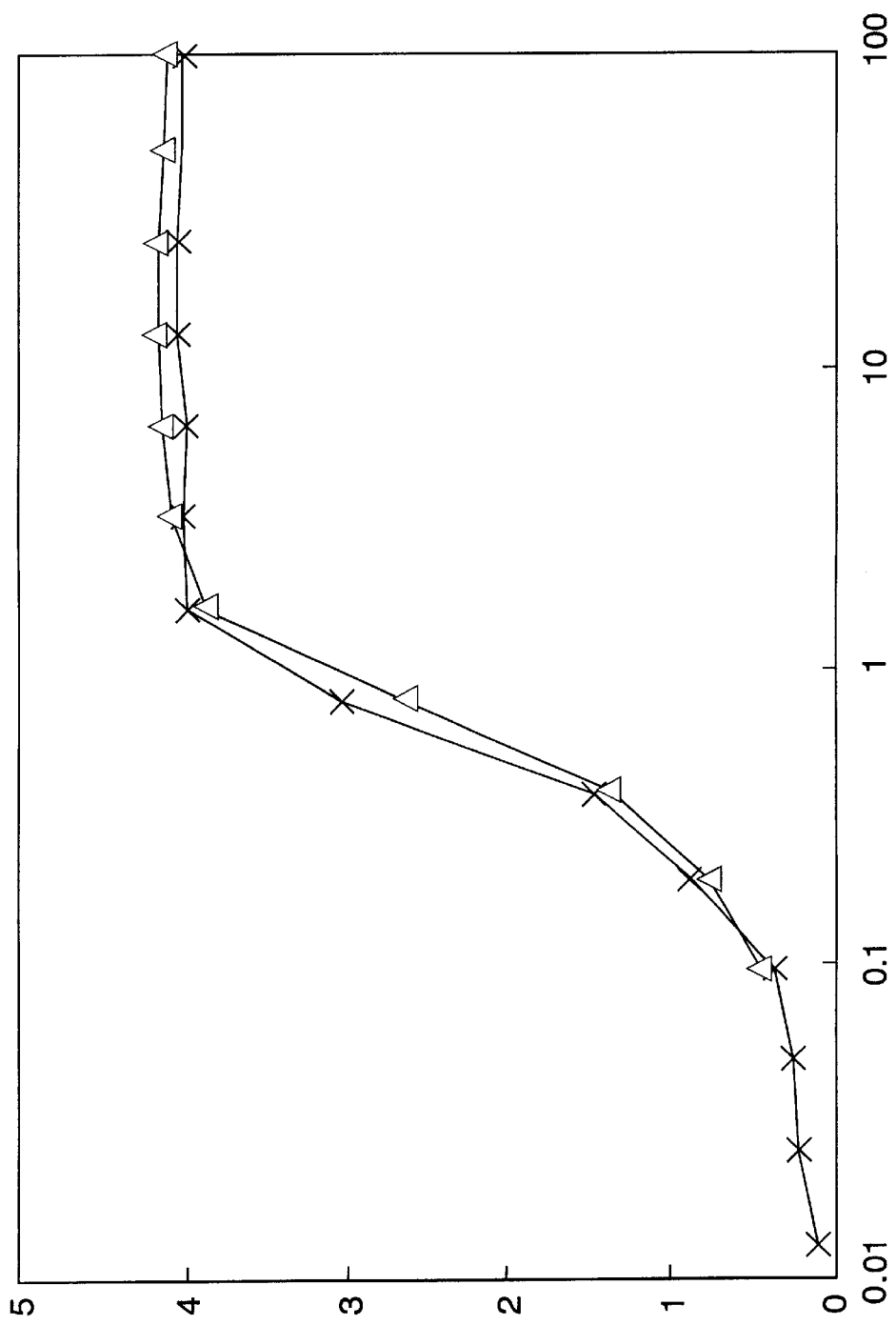
FIG. 8. ELISA profile of MAb 8A1 at 1:1000 with or without washing with Tween-20. The profile did not differ after washing with or without Tween-20. X indicates without Tween-20; Δ indicates with 0.1% Tween-20. The absorbance at 490 nm is shown on the y axis against the ng quantities of MPL/well on the x axis.

In the present studies, mice previously immunized with irradiated syngeneic melanoma cells that had MPL in their membranes and then subsequently challenged with live tumor cells survived better, whereas those immunized with either irradiated melanoma cells alone, or MPL alone, all died (Table 6, Table 7 and FIG. 8). In further analyses of tumor growth, better survival and retarded growth of challenged tumor cells was found to result in the mice immunized with adjuvant-coupled cells, in contrast to that in mice immunized with adjuvant or cells alone (Table 7). The anti-tumor effects were also observed to be dose-dependent (Table 8). The days of survival decreased, and the tumor growth increased, with decreasing dose of vaccine.

The results of the present inventors' were particularly interesting in light of the studies of Johnston & Bystryn (1991). These authors tested the effectiveness of MPL, in combination with mycobacterial cell wall skeleton, on a melanoma vaccine of murine B16 cells. Although humoral responses were observed in theses studies, the MPL adjuvant combination did not potentiate tumor-protective immunity (Johnston & Bystryn, 1991). This is in contrast to the marked anti-tumor effectiveness of the adjuvant-incorporated cells of this invention.

Using this invention, the antibodies elicited against membrane-bound gangliosides may or may not be specific for a particular species of ganglioside, but will nevertheless still be useful. Two kinds of cells were used for immunization, each cell type differed in their ganglioside profile. From the results presented herein, it is likely that immunization with MPL-attached cells containing gangliosides will elicit a response against all the gangliosides found on the cell surface.

The present invention is elegantly simple and provides a single effective method for increasing immune responses and anti-cancer responses that could not be predicted from the complex and contradictory teachings of the prior art. The methodology of the invention is straightforward and may be used in the context of any cell expressing any antigen, and may be used with a wide variety of adjuvants. This is in contrast with the restricted and more complex previous methods, such as those described in U.S. Pat. No. 5,312,620. The present invention also represents a conceptual departure that was not suggested in the prior art.

The ganglioside profile of M-25 cells includes $GM_3$ (30%), $GM_2$ (<5%) and $GD_3$ (58%) and $O-AcGD_3$ (7%) (Ravindranath et al., 1988). However, during column chromatographic purification of these gangliosides from a large quantity of ganglioside extracts of the M25 cell line, it was noted that the cell line also contained $GD_2$, which could not be detected in routine thin layer chromatographic analysis of the ganglioside extracts. The heterogeneity of the ganglioside profile of M25 cells most likely explains why M25 cells elicited antibody responses against a variety of gangliosides. MPL augmented the IgM response against all such membrane gangliosides.

In contrast to human cells, the murine melanoma B16 cells contain predominantly $GM_3$ (Hirabayashi et al., 1985). The sialic acid of $GM_3$ derived from B16 is NeuAc (Hirabayashi et al., 1985). The total lipid bound sialic acid extracted from B16 (F10 (metastasizes to lung)) ranged from 82 to 115 µg/gm wet weight of cells (approximately $1\times10^7$ cells).

In testing the sera immunized with MPL-attached B16 cells, an IgM antibody response to $GD_3$, a ganglioside not commonly detected in B16 cells, was observed. Considering the structural similarities between $GM_3$ and $GD_3$, a cross reaction between the two gangliosides is not surprising. Anti-ganglioside monoclonal antibodies (MAbs) with dual or multispecificity are also common in the literature (Ravindranath et al., 1989; Irie & Ravindranath, 1990). A $GM_3$-binding human monoclonal IgM antibody, developed from lymphocytes of a cancer patient, has also been found to react with $GD_3$ equally in ELISA, suggesting that the antibodies may recognize an epitope common to $GM_3$ and $GD_3$.

Gangliosides are known to elicit IgM but not IgG antibodies. This is not unusual because gangliosides, like other carbohydrate antigens, are incapable of T-cell recognition due to a failure to interact with MHC restriction elements (Hardings et al., 1991; Ishioka et al., 1992). Gangliosides are thus classified as T-cell independent antigens. In using anti-ganglioside antibodies to reduce or eliminate gangliosides shed from tumor tissues, the pentameric IgM is actually a better candidate that the monomeric IgG.

Anti-ganglioside IgM antibodies are also found in sham controls at low levels. Considering the fact that the anti-ganglioside antibodies could be naturally occurring autoantibodies, it is reasonable to expect that they may have low affinity (intrinsic affinity) and high avidity (Avrameas, 1993). Although an understanding of the mechanism of action is not relevant to practicing the present invention, an explanation of the ability of MPL to unmask tumor cell-associated gangliosides may be found in the precursors of MPL. Lipid A and lipopolysaccharides are potent B-cell adjuvants (Dresser & Phillips, 1973) that perform similar functions when bound to artificial liposome membranes (Schuster et al., 1979; Banerji et al., 1982; Tamauchi et al., 1983). However, unlike its precursors, MPL is nontoxic in cancer patients (Vosika et al., 1984; Harel et al., 1990). The results presented herein support the hypothesis that MPL's immunobiologic activity reflects its mode of presentation.

MPL was found to be surprisingly effective when conjugated to the surface of tumor cells, but to have no significant immunopotentiating activity in aqueous preparations (micellar form). Livingston et al. (1987a) previously examined anti-GM2 antibody responses after immunizing mice with an MPL-liposome vaccine incorporating both MPL and $GM_2$ in a liposome. However, these results did not compare in effectiveness with the MPL-tumor cell composition of this invention.

This invention emphasizes the importance of incorporating an immunopotentiating agent in a tumor cell vaccine (here "vaccine" means immunotherapeutic). Currently, vaccine therapy is administered in conjunction with adjuvants, such as muraminyl peptide, Freund's adjuvant, BCG, BCG-cell wall skeleton with or without trehalose dimycolate, and *Cornybacterium parvum* (Morton & Ravindranath, 1993).

The present findings show that adjuvants would be more effective if incorporated in the membranes of tumor cells in the vaccine. This is a significant advance over using tumor cells mixed with BCG (Bartlett & Zbar, 1972; Bast et al., 1974; Ravindranath et al., 1988; Morton & Ravindranath, 1993; Morton et al., 1993).

II. Adjuvants

Immunization protocols have used adjuvants to stimulate responses for many years. Some adjuvants affect the way in which antigens are presented. For example, the immune response is increased when protein antigens are precipitated by alum. Emulsification of antigens also prolongs the duration of antigen presentation. Other adjuvants, for example, certain organic molecules obtained from bacteria, act on the host rather than on the antigen. An example is muramyl dipeptide (N-acetylmuramyl-L-alanyl-D-isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen-specific. If they are administered together with a purified antigen, however, they can be used to selectively promote the response to the antigen.

Adjuvants have been used experimentally to promote a generalized increase in immunity against unknown antigens (e.g., U.S. Pat. No. 4,877,611). This has been attempted particularly in the treatment of cancer. For many cancers, there is compelling evidence that the immune system participates in host defense against the tumor cells, but only a fraction of the likely total number of tumor-specific antigens are believed to have been identified to date. However, using the present invention, the inclusion of a suitable adjuvant into the membrane of an irradiated tumor cell will likely increase the anti-tumor response irrespective of the molecular identification of the prominent antigens. This is a particularly important and time-saving feature of the invention.

The present invention contemplates that a variety of adjuvants may be employed in the membranes of cells, such as tumor cells, resulting in an improved immunogenic composition. The only requirement is, generally, that the adjuvant be capable of incorporation into, physical association with, or conjugation to, the cell membrane of the cell in question.

Certain useful adjuvants are listed in Table 1. This list is not intended to be exhaustive, merely exemplary of the different kinds of adjuvants that can be conjugated to cellular vaccines in accordance with this invention.

TABLE 1

Exemplary Adjuvants for Conjugation to Cells.

| | |
|---|---|
| Alhydrogel | |
| Alkyl lysophosphilipids (ALP) | |
| BCG | |
| Bestatin | |
| Biliverdin | including derivatives and glycoconjugates |
| Bilirubin | including derivatives and glycoconjugates, such as monoglycouranoglycans and diglycouranoglycans |
| Biotin | including biotinylated derivatives |
| Carnosine | including derivatives |
| Chitin | |
| Citosan | deacetylated chitin |
| Cholesteryl succinate | |
| *Cornyebacteriuin parvum* | whole or part of cell including oligosaccharides and glycolipids |

TABLE 1-continued

Exemplary Adjuvants for Conjugation to Cells.

| | |
|---|---|
| C. granulosum | whole or part of cell including P40 a peptidoglycan with a glycoprotein deacetylated synthetic |
| monophoshoryl lipid A | |
| monophosphoryl lipid A isoprinosine | |
| lithosperman | lithosperman A, lithosperman B or lithosperman C |
| Trehalose monomycolate | |
| Trehalose dimycolate | |
| Mycobacterial species | whole or part of cell including glycolipids, phenolic glycolipids, peptides such as 45/47 kda and BCG |
| Muramyl dipeptide | N-acetyl muramyl-L-alanyl-D-isoglutamine |
| Muramyl tripeptide | MF75.2 |
| threonyl-muramyl dipeptide | |
| murametide | |
| murabutide | |
| lipoteichoic acid | LTA |
| ribitol teichoic acid | RTA |
| glycerol teichoic acid | GTA |
| Superantigens | S. aureus enterotoxins S. epidermidis enterotoxins S. pyogenes enterotoxins E. coli exotoxins |
| Staphylococcus species | whole or part of cell including peptidoglycans and enterotoxins |
| Viruses | whole or part of particle including Vaccinia, Newcastle disease visurs, vesicular stomatitis virus, papilloma virus and rhinovirus |
| synthetic peptides | pentamers, hexamers, heptamers, octamers, nonamers, decamers, etc.; such as polylysine and threonine-alanine peptides |
| Recombinant Prolactin | |
| Glycosaminoglycans | and lipid and peptide derivatives |
| glycosaminoglycouranoglycans | |
| glycosaminoglycolipids | |
| glycosaminoglycouranoglycolipids | |
| glycosaminoglycopeptides | |
| glycosaminoglycouranoglycopeptides | |
| phosphorylated glycosaminoglycans | |
| sulphanted glycosaminoglycan | |
| QS-21 | |
| Quil-A | |
| Polymethylmethyl acrylate (PMMA) | |
| Retinoic acid | |
| Lentinan | |
| Levan | |
| Malic anhydride-divinyl ether (MVE-2) | |
| hemocyanin | from keyhole limpet (KLH) |
| hemoerythrin | molluscan, arthropod hemoerythrin from annelids and lower invertebrates |
| pteridines | |
| nucleic acids | preferably poly A, poly T, poly AT, poly GC and poly IC-LC |
| oligonucleotides | varying kilobases |
| lentinen | |
| lectins | part or whole; from plants and animals |

Certain adjuvants particularly contemplated for use are the technic acids from Gram -ve cells. These include the lipoteichoic acids (LTA), ribitol technic acids (RTA) and glycerol technic acid (GTA). Active forms of their synthetic counterparts may also be employed in connection with the invention (Takada et al., 1995).

Hemocyanins and hemoerythrins may also be used in the invention. The use of hemocyanin from keyhole limpet (KLH) is particularly preferred, although other molluscan and arthropod hemocyanins and hemoerythrins may be employed.

Various polysaccharide adjuvants may also be used. For example, Yin et al. (1989) describe the use of various pneumococcal polysaccharide adjuvants on the antibody responses of mice. The doses that produce optimal responses, or that otherwise do not produce suppression, as indicated in Yin et al. (1989) should be employed. Polyamine varieties of polysaccharides are particularly preferred, such as chitin and chitosan, including deacetylated chitin.

A further preferred group of adjuvants are the muramyl dipeptide (MDP, N-acetylmuramyl-L-alanyl-D-isoglutamine) group of bacterial peptidoglycans. Derivatives of muramyl dipeptide, such as the amino acid derivative threonyl-MDP, and the fatty acid derivative MTPPE, are also contemplated.

U.S. Pat. No. 4,950,645 describes a lipophilic disaccharide-tripeptide derivative of muramyl dipeptide which is proposed for use in artificial liposomes formed from phosphatidyl choline and phosphatidyl glycerol. It is said to be effective in activating human monocytes and destroying tumor cells, but is non-toxic in generally high doses. The compounds of U.S. Pat. No. 4,950,645 and PCT Patent Application WO 91/16347, which have not previously been suggested for use with cellular carriers, are now proposed for use in the present invention.

BCG and BCG-cell wall skeleton (CWS) may also be used as adjuvants in the invention, with or without trehalose dimycolate. Trehalose dimycolate may be used itself. Azuma et al. (1988) show that trehalose dimycolate administration correlates with augmented resistance to influenza virus infection in mice. Trehalose dimycolate may be prepared as described in U.S. Pat. No. 4,579,945.

Amphipathic and surface active agents, e.g., saponin and derivatives such as QS21 (Cambridge Biotech), form yet another group of preferred adjuvants for use with the immunogens of the present invention. Nonionic block copolymer surfactants (Rabinovich et al., 1994; Hunter et al., 1991) may also be employed. Oligonucleotides, as described by Yamamoto et al. (1988) are another useful group of adjuvants. Quil A and lentinen complete the currently preferred list of adjuvants. Although each of the agents, and the endotoxins described below, are well-known as adjuvants, these compounds have not been previously incorporated into the membrane of a target cell, as shown herein.

Superantigens are also contemplated for use as adjuvants in the present invention. "Superantigens" are generally bacterial products that stimulate a greater proportion of T lymphocytes than peptide antigens without a requirement for antigen processing (Mooney et. al., 1994). Superantigens include Staphylococcus exoproteins, such as the alpha, beta, gamma and delta enterotoxins from S. aureus and S. epidermidis, and the alpha, beta, gamma and delta E. coli exotoxins.

Common Staphylococcus enterotoxins are known as staphylococcal enterotoxin A (SEA) and staphylococcal enterotoxin B (SEB), with enterotoxins through E (SEE) being described (Rott et. al., 1992). Streptococcus pyogenes B (SEB), Clostridium perfringens enterotoxin (Bowness et. al., 1992), cytoplasmic membrane-associated protein (CAP) from S. pyogenes (Sato et. al., 1994) and toxic shock syndrome toxin-1 (TSST-1) from S. aureus (Schwab et. al., 1993) are further useful superantigens.

One group of adjuvants particularly preferred for use in the invention are the detoxified endotoxins, such as the refined detoxified endotoxin of U.S. Pat. No. 4,866,034. These refined detoxified endotoxins are effective in producing adjuvant responses in mammals.

The detoxified endotoxins may be combined with other adjuvants to prepare multi-adjuvant-incorporated cells. Combination of detoxified endotoxins with trehalose dimycolate is contemplated, as described in U.S. Pat. No. 4,435,386. Combinations of detoxified endotoxins with trehalose dimycolate and endotoxic glycolipids is also contemplated (U.S. Pat. No. 4,505,899), as is combination of detoxified endotoxins with cell wall skeleton (CWS) or CWS and trehalose dimycolate, as described in U.S. Pat. Nos. 4,436,727, 4,436,728 and 4,505,900. Combinations of just CWS and trehalose dimycolate, without detoxified endotoxins, is also envisioned to be useful, as described in U.S. Pat. No. 4,520,019.

MPL is currently one preferred immunopotentiating agent for use in improved adjuvant-incorporated tumor cell compositions and vaccines. Many scientific articles have described various classical uses of MPL, however, none appear to have suggested that MPL may be combined into the membrane of a cell, along with the antigens in question, in the manner described by the present inventors. Furthermore, certain scientific articles address potential drawbacks of MPL as previously used in the art, such as, for example, its relatively small size, which results in clearance from the circulation within a short time period (Baker et al. (1988b). Indeed, this drawback applies to any small-sized adjuvant, and is yet another problem solved by the present invention.

References that concern the uses of MPL include Tomai et al. (1987), Chen et al. (1991) and Garg & Subbarao (1992), that each concern certain roles of MPL in the reactions of aging mice; Elliott et al. (1991), that concerns the D-galactosamine loaded mouse and its enhanced sensitivity to lipopolysaccharide and MPL; Chase et al. (1986), that relates to bacterial infections; and Masihi et al. (1988), that describes the effects of MPL and endotoxin on resistance of mice to *Toxoplasma gondii*. Fitzgerald (1991) also reported on the use of MPL to up-regulate the immunogenicty of a syphilis vaccine and to confer significant protection against challenge infection in rabbits.

Thus MPL is known to be safe for use, as shown in the above model systems. Phase I clinical trials have also shown MPL to be safe for use (Vosika et al., 1984). Indeed, 100 $\mu g/m^2$ is known to be safe for human use, even on an outpatient basis (Vosika et al., 1984).

MPL generally induces polyclonal B cell activation (Baker et al., 1994), and has been shown to augment antibody production in many systems, for example, in immunologically immature mice (Baker et al., 1988); in aging mice (Tomai & Johnson, 1989); and in nude and Xid mice (Madonna & Vogel, 1986; Myers et al., 1995). Antibody production has been shown against erythrocytes (Hraba et al., 1993); T cell dependent and independent antigens; Pnu-immune vaccine (Garg & Subbarao, 1992); isolated tumor-associated antigens (U.S. Pat. No. 4,877,611); against syngeneic tumor cells (Livingston et al., 1985; Examples 1–5; Ravindranath et al., 1994a;b); and against tumor-associated gangliosides (Examples 1–5; Ravindranath et al., 1994a;b).

Another useful attribute of MPL is that is augments IgM responses, as shown by Baker et al. (1988a), who describe the ability of MPL to increase antibody responses in young mice. This is a particularly useful feature of an adjuvant for use in certain embodiments of the present invention. Myers et al. (1995) recently reported on the ability of MPL to induce IgM antibodies, by virtue T-cell-independent antibody production.

In the Myers et al. (1995) studies, MPL was conjugated to the hapten, TNP. MPL was proposed for use as a carrier for other haptens, such as peptides. This proposal suggesting MPL as a carrier for a given antigen (Myers et al., 1995), is generally in contrast to the present invention, in which whole cells are used as a carrier for both the antigens and the inserted adjuvants.

MPL also activates and recruits macrophages (Verma et al., 1992). Tomai and Johnson (1989) showed that MPL-stimulated T cells enhance IL-1 secretion by macrophages. MPL is also known to activate superoxide production, lysozyme activity, phagocytosis, and killing of Candida in murine peritoneal macrophages (Chen et al., 1991).

The effects of MPL on T cells include the endogenous production of cytotoxic factors, such as TNF, in serum of BCG-primed mice by MPL (Bennett et al., 1988). Kovach et al. (1990) and Elliot et al. (1991) also show that MPL induces TNF activity. MPL is known to act with TNF-$\alpha$ to induce release of IFN-$\gamma$ by NK cells. IFN-$\gamma$ production by T cells in response to MPL was also documented by Tomai & Johnson (1989) and Odean et al. (1990).

MPL is also known to be a potent T cell adjuvant. For example, MPL stimulates proliferation of melanoma-antigen specific CTLs (Mitchell et al., 1988, 1993). Further, Baker et al. (1988b) showed that nontoxic MPL inactivated suppressor T cell activity. Naturally, in the physiological environment, the inactivation of T suppressor cells allows for increased benefit for the animal, as realized by, e.g., increased antibody production. Johnson & Tomai (1988) have reported on the possible cellular and molecular mediators of the adjuvant action of MPL.

MPL is also known to induce aggregation of platelets and to phosphorylate a platelet protein prior to induction of serotonin secretion (Grabarek et al., 1990). This study shows that MPL is involved in protein kinase C activation and signal transduction.

Many articles concern the structure and function of MPL include. These include Johnson et al. (1990), that describes the structural characterization of MPL homologs obtained from *Salmonella Minnesota* Re595 lipopolysaccharide. The work of Johnson et al. (1990), in common with Grabarek et al. (1990), shows that the fatty acid moieties of MPL can vary, even in commercial species. In separating MPL into eight fractions by thin layer chromatography, Johnson et al. (1990) found that three were particularly active, as assessed using human platelet responses. The chemical components of the various MPL species were characterized by Johnson et al. (1990). MPL with a structure in accordance with that found in Fraction 8 was used in the studies relating to the present invention, and is currently preferred for use in adjuvant-incorporated cells.

Baker et al. (1992) further analyzed the structural features that influence the ability of lipid A and its analogs to abolish expression of suppressor T cell activity. They reported that decreasing the number of phosphate groups in lipid A from two to one (i.e., creating monophosphoryl lipid A, MPL) as well as decreasing the fatty acyl content, primarily by removing the residue at the 3 position, resulted in a progressive reduction in toxicity; however, these structural modifications did not influence its ability to abolish the expression of Ts function (Baker et al., 1992). These types of MPL are ideal for use in the present invention.

Baker et al. (1992) also showed that reducing the fatty acyl content from five to four (lipid A precursor $IV_A$ or $I_a$) eliminated the capacity to influence Ts function but not to induce polyclonal activation of B cells. These studies show that in order to be able to abolish the expression of Ts function, lipid A must be a glucosamine disaccharide; may have either one or two phosphate groups; and must have at least five fatty acyl groups. Also, the chain length of the nonhydroxylated fatty acid, as well as the location of acyloxyacyl groups (2' versus 3' position), may play an important role (Baker et al., 1992).

In examining the relationship between chain length and position of fatty acyl groups on the ability of lipid A to abolish the expression of suppressor T-cell (Ts) activity, Baker et al. (1994) found that fatty acyl chain lengths of $C_{12}$ to $C_{14}$ appeared to be optimal for bioactivity. Therefore, although their use is still possible, lipid A preparations with fatty acyl groups of relatively short chain length ($C_{10}$ to $C_{12}$ from *Pseudomonas aeruginosa* and *Chromobacterium violaceum*) or predominantly long chain length ($C_{18}$ from *Helicobacter pylori*) are less preferred for use in this invention.

Baker et al. (1994) also showed that the lipid A proximal inner core region oligosaccharides of some bacterial lipopolysaccharides increase the expression of Ts activity; due mainly to the capacity of such oligosaccharides, which are relatively conserved in structure among gram-negative bacterial, to enlarge or expand upon the population of $CD8^+$ Ts generated during the course of a normal antibody response to unrelated microbial antigens. The minimal structure required for the expression of the added immunosuppression observed was reported to be a hexasaccharide containing one 2-keto-3-deoxyoctonate residue, two glucose residues, and three heptose residues to which are attached two pyrophosphorylethanolamine groups (Baker et al., 1994). This information may be considered in utilizing or even designing further adjuvants for use in the invention.

In a generally related line of work, Tanamoto et al. (1994a;b; 1995) described the dissociation of endotoxic activities in a chemically synthesized Lipid A precursor after acetylation or succinylation. Thus, compounds such as "acetyl 406" and "succinyl 516" (Tanamoto et al., 1994a;b; 1995) are also contemplated for use in the invention.

Synthetic MPLs form a particularly preferred group of antigens. For example, Brade et al. (1993) described an artificial glycoconjugate containing the bisphosphorylated glucosamine disaccharide backbone of lipid A that binds to anti-Lipid A MAbs. This is one candidate for use in certain aspects of the invention.

The MPL derivatives described in U.S. Pat. No. 4,987,237 are particularly contemplated for use in the present invention. U.S. Pat. No. 4,987,237 describes MPL derivatives that contain one or more free groups, such as amines, on a side chain attached to the primary hydroxyl groups of the monophosphoryl lipid A nucleus through an ester group. The derivatives provide a convenient method for coupling the lipid A through coupling agents to various biologically active materials. The immunostimulant properties of lipid A are maintained. All MPL derivatives in accordance with U.S. Pat. No. 4,987,237 are envisioned for use in the MPL adjuvant-incorporated cells of this invention.

Various adjuvants, even those that are not commonly used in humans, may still be employed in animals, where, for example, one desires to raise antibodies or to subsequently obtain activated T cells. The toxicity or other adverse effects that may result from either the adjuvant or the cells, e.g., as may occur using non-irradiated tumor cells, is irrelevant in such circumstances.

III. Cellular Components

A wide variety of cells are also contemplated for use as the cellular components of adjuvant-incorporated cell constructs in accordance with the present invention. Any cell that has a membrane component against which one desires to generate an antibody may be used.

All cell types are thus included so long as, generally, the cell may be isolated in a form with a substantially intact membrane. This includes embryonic cells and non naturally-occurring cells in the context of, e.g., virally infected cells that express viral protein components on the surface.

A. Erythrocytes

One type of cells that is particularly suited for use in this invention is the erythrocyte. In terms of clinical treatment for various diseases, particularly in cancer treatment, patients' autologous erythrocytes are contemplated for use. There are many advantages to the uses of erythrocytes, as described in the following section.

A growing tumor sheds it antigens into the circulation. Often these circulating antigens are entrapped by erythrocytes, forming "coated erythrocytes". Portukalian et al. (1978) observed that the erythrocytes of melanoma patients obtained before surgical resection of tumor contain large amounts of tumor derived gangliosides. The level of these gangliosides on erythrocytes declined after surgery suggesting that the gangliosides on tumor cell surface reflect the tumor burden and shed gangliosides (Portukalian et al., 1978).

It is a concept of this invention that erythrocytes from cancer patients will likely accommodate many tumor associated antigens. In any event, the erythrocytes of cancer patients are different from that of normal individuals in that they have at least some tumor associated antigens on their surface. The use of "autologous erythrocytes" for adjuvant conjugation is presently envisioned. In this aspect of the invention, erythrocytes would be obtained from a cancer patient, incorporated with adjuvant as described herein, and then administered back into the same patient such that the adjuvant augments the immune response against the tumor associated antigens found on erythrocyte cell surface.

This aspect of the invention has many favorable features. For example, erythrocytes are very abundant cells and are readily obtained. Indeed, it is one of the simplest clinical procedures to obtain a sample of a patient's blood and to prepare the erythrocyte-containing fraction. In contrast, obtaining autologous tumor cells may be difficult due to tissue biopsy or extraction. Autologous tumor cells may also be in scant supply, and can be difficult to grow in sufficient quantities in culture conditions.

In the erythrocyte aspects of the invention there is no need to grow erythrocytes in culture conditions at all. This provides advantages of both time and cost over using autologous or allogenic tumor cell lines. Furthermore, the erythrocytes are not exposed to artificial culture conditions or to animal serum proteins, such as fetal calf serum, as are cultured tumor cells. This lessens the possibility that the tumor cells exhibit phenotypic changes during cell culture, which may render their antigenic profile one step removed from that of the tumor cells in the animal.

The fact that erythrocytes are anucleated cells provides further advantages. For example, they cannot further mutate when re-administered. Also, the life time of the erythrocyte is finite, which provides for ready control of the adjuvant-incorporated cells circulating in the patient at any given time. Furthermore, unwanted immune responses directed against the nucleus, nuclear proteins, nucleic acids (such as anti-DNA antibodies and anti-nuclear antibodies) can be avoided by using a nuclear cells as a therapeutic. As a sequel, the pressure on the immune system and functions will be minimized.

In the practice of the invention, if it was desired to increase the coating of autologous erythrocytes with tumor antigens, this could be readily achieved by adding a sufficient amount of the desired or selected tumor antigens in vitro, along with the adjuvant to facilitate immunopotentiation. Also, different antigens, or a combination of antigens, could be added, as desired.

To increase the induction of immune responses that are restricted to the specific tumor-associated antigen coating the erythrocytes, tolerance may be first induced to autologous erythrocytes using tumor-antigen-free erythrocytes. Subsequent exposure to adjuvant-incorporated erythrocytes with tumor antigens would then elicit a specific anti-tumor response. This would likely circumvent any autoimmunity to self-antigens or hemolysis that may possibly occur in this process.

B. Tumor Cells

A further particular group of cells that are suited for use in this invention are tumor cells. The range of animal and human tumor-derived or associated cells that may be used to stimulate an immune response against a cell component is virtually limitless.

By way of example only, several tumor cell lines and their sources are listed in Table 2 and Table 3, and are further disclosed in the ATCC Catalogues. Table 2 lists an extensive number of tumor cell lines that are categorized according to the source of the tumor. The designation originally applied to the tumor cell and the ATCC Accession Nos. are also given. Although a number of human cell lines are listed within Table 2, for convenience, Table 3 is also provided as a list specifically directed to human tumor cell lines that are available from the ATCC.

TABLE 2

Tumor Cell Lines

| SOURCE (SPECIES/SITE) OF TUMOR CELL | TUMOR CELL LINE | ATCC ® NO. |
|---|---|---|
| Abelson virus-induced | | |
| mouse | WEHI 274.1 | CRL 1679 |
| Adenocarcinoma, see carcinoma | | |
| Adenoma | | |
| mouse, lung | LA-4 | CCL 196 |
| rat, pituitary | RC-4B/C | CRL 1903 |
| Adrenal tumor | | |
| mouse | Y-1 | CCL 79 |
| Astrocytoma | | |
| human | CCF-STTG1 | CRL 1718 |
| | SW 1088 | HTB 12 |
| | SW 1783 | HTB 13 |
| | U-87 MG | HTB 14 |
| | U-373 MG | HTB 17 |
| Bladder tumor | | |
| rat | NBT-II | CRL 1655 |
| Brain tumor | | |
| mouse | BC₃H1 | CRL 1443 |
| Burkitt lymphoma | | |
| human | | |
| ascitic fluid | CA46 | CRL 1648 |
| | Jiyoye | CCL 87 |
| | P3HR-1 | HTB 62 |
| | ST486 | CRL 1647 |
| lymphoblast, B | Daudi | CCL 213 |
| lymphoblast-like cells | EB-3 | CCL 85 |
| lymphoblastoid | Namalwa | CRL 1432 |
| lymphocyte, B | Ramos | CRL 1596 |
| maxilla | EB1 | HTB 60 |
| | Raji | CCL 86 |
| ovary | EB2 | HTB 61 |
| Carcinoma | | |

TABLE 2-continued

Tumor Cell Lines

| SOURCE (SPECIES/SITE) OF TUMOR CELL | TUMOR CELL LINE | ATCC ® NO. |
|---|---|---|
| guinea pig | GPC-16 | CCL 242 |
| human | | |
| adrenal cortex | NCI-H295 | CRL 10296 |
| | SW-13 | CCL 105 |
| bladder | 5637 | HTB 9 |
| | HT-1197 | CRL 1473 |
| | HT-1376 | CRL 1472 |
| | J82 | HTB 1 |
| | RT4 | HTB 2 |
| | SCaBER | HTB 3 |
| | T24 | HTB 4 |
| | TCCSUP | HTB 5 |
| | UM-UC-3 | CRL 1749 |
| breast | BT-20 | HTB 19 |
| | BT-474 | HTB 20 |
| | BT-483 | HTB 121 |
| | BT-549 | HTB 122 |
| | DU 4475 | HTB 123 |
| | Hs 578T | HTB 126 |
| | MCF7 | HTB 22 |
| | MDA-MB-134-VI | HTB 23 |
| | MDA-MB-157 | HTB 24 |
| | MDA-MB-175-VII | HTB 25 |
| | MDA-MB-231 | HTB 26 |
| | MDA-MB-330 | HTB 127 |
| | MDA-MB-361 | HTB 27 |
| | MDA-MB-415 | HTB 128 |
| | MDA-MB-435S | HTB 129 |
| | MDA-MB-436 | HTB 130 |
| | MDA-MB-453 | HTB 131 |
| | MDA-MB-468 | HTB 132 |
| | SK-BR-3 | HTB 30 |
| | T-47D | HTB 133 |
| | UACC-812 | CRL 1897 |
| | UACC-893 | CRL 1902 |
| | ZR-75-1 | CRL 1500 |
| | ZR-75-30 | CRL 1504 |
| bronchus | ChaGo K-1 | HTB 168 |
| cecum | NCI-H498 | CCL 254 |
| | NCI-H508 | CCL 253 |
| | NCI-H716 | CCL 251 |
| | NCI-H747 | CCL 252 |
| | SNU-C2A | CCL 250.1 |
| | SNU-C2B | CCL 250 |
| cervix | CaSki | CRL 1550 |
| | C-4 I | CRL 1594 |
| | C-4 II | CRL 1595 |
| | C-33A | HTB 31 |
| | HeLa | CCL 2 |
| | HeLa S3 | CCL 2.2 |
| | HeLa 229 | CCL 2.1 |
| | HT-3 | HTB 32 |
| | ME-180 | HTB 33 |
| | MS 751 | HTB 34 |
| | SiHa | HTB 35 |
| colon | Caco-2 | HTB 37 |
| | COLO 201 | CCL 224 |
| | COLO 205 | CCL 222 |
| | COLO 320 DM | CCL 220 |
| | COLO 320 HSR | CCL 220.1 |
| | DLD-1 | CCL 221 |
| | HCT-15 | CCL 225 |
| | HCT-116 | CCL 247 |
| | HT-29 | HTB 38 |
| | LoVo | CCL 229 |
| | LS 123 | CCL 255 |
| | LS 174T | CL 188 |
| | LS 180 | CL 187 |
| | NCI-H548 | CCL 249 |
| | SK-CO-1 | HTB 39 |
| | SW48 | CCL 231 |
| | SW403 | CCL 230 |
| | SW480 | CCL 228 |

TABLE 2-continued

Tumor Cell Lines

| SOURCE (SPECIES/SITE) OF TUMOR CELL | TUMOR CELL LINE | ATCC ® NO. |
|---|---|---|
| | SW620 | CCL 227 |
| | SW948 | CCL 237 |
| | SW 1116 | CCL 233 |
| | SW 1417 | CCL 238 |
| | T84 | CCL 248 |
| | WiDr | CCL 218 |
| duodenum | HuTu 80 | HTB 40 |
| endometrium | AN3 CA | HTB 111 |
| | HEC-1-A | HTB 112 |
| | HEC-1-B | HTB 113 |
| | KLE | CRL 1622 |
| | RL95-2 | CRL 1671 |
| gastric: See stomach | | |
| intestine, small | HCT-8 | CCL 244 |
| intestine (?) | Hs 700T | HTB 147 |
| kidney | 769-P | CRL 1933 |
| | 786-O | CRL 1932 |
| | A-498 | HTB 44 |
| | A-704 | HTB 45 |
| | ACHN | CRL 1611 |
| | Caki-1 | HTB 46 |
| | Caki-2 | HTB 47 |
| | SW 839 | HTB 49 |
| larynx | HEp-2 | CCL 23 |
| liver | Capan-1 | HTB 79 |
| | Hep 3B | HB 8064 |
| | Hep G2 | HB 8065 |
| | SK-HEP-1 | HTB 52 |
| lung | A-427 | HTB 53 |
| | A549 | CCL 185 |
| | Calu-1 | HTB 54 |
| | Calu-3 | HTB 55 |
| | Calu-6 | HTB 56 |
| | NCI-H69 | HTB 119 |
| | NCI-H82 | HTB 175 |
| | NCI-H128 | HTB 120 |
| | NCI-H146 | HTB 173 |
| | NCI-H207 | HTB 172 |
| | NCI-H292 | CRL 1848 |
| | NCI-H345 | HTB 180 |
| | NCI-H441 | HTB 174 |
| | NCI-H446 | HTB 171 |
| | NCI-H460 | HTB 177 |
| | NCI-H510A | HTB 184 |
| | NCI-H520 | HTB 182 |
| | NCI-H596 | HTB 178 |
| | NCI-H661 | HTB 183 |
| | NCI-H676B | HTB 179 |
| | NCI-H820 | HTB 181 |
| | SK-LU-1 | HTB 57 |
| | SK-MES-1 | HTB 58 |
| | SW900 | HTB 59 |
| mouth | KB | CCL 17 |
| nasal septum | RPMI 2650 | CCL 30 |
| ovary | Caov-3 | HTB 75 |
| | Caov-4 | HTB 76 |
| | NIH: OVCAR-3 | HTB 161 |
| | PA-1 | CRL 1572 |
| | SK-OV-3 | HTB 77 |
| | SW626 | HTB 78 |
| pancreas | ASPC-1 | CRL 1682 |
| | Bx PC-3 | CRL 1687 |
| | Capan-1 | HTB 79 |
| | Capan-2 | HTB 80 |
| | CFPAC-1 | CRL 1918 |
| | Hs 700T | HTB 147 |
| | Hs 766T | HTB 134 |
| | MIA PaCa-2 | CRL 1420 |
| | PANC-1 | CRL 1469 |
| | SU.86.86 | CRL 1837 |
| pharynx | Detroit 562 | CCL 138 |
| | FaDu | HTB 43 |
| placenta | BeWo | CCL 98 |
| | JAR | HTB 144 |
| | JEG-3 | HTB 36 |
| prostate | DU145 | HTB 81 |
| | LNCaP.FGC | CRL 1740 |
| | PC-3 | CRL 1435 |
| rectum | SW 837 | CCL 235 |
| | SW 1463 | CCL 234 |
| skin | A-431 | CRL 1555 |
| stomach | AGS | CRL 1739 |
| | Hs 746T | HTB 135 |
| | KATO III | HTB 103 |
| | RF-1 | CRL 1864 |
| | RF-48 | CRL 1863 |
| submaxillary gland | A-253 | HTB 41 |
| testis | Cates 1B | HTB 104 |
| | Tera-1 | HTB 105 |
| | Tera-2 | HTB 106 |
| thyroid | Sw 579 | HTB 107 |
| | TT | CRL 1803 |
| tongue | SCC-4 | CRL 1624 |
| | SCC-9 | CRL 1629 |
| | SCC-15 | CRL 1623 |
| | SCC-25 | CRL 1628 |
| unknown | Hs 696 | HTB 151 |
| vulva | Sw 954 | HTB 117 |
| | SW 962 | HTB 118 |
| mouse | | |
| ascites | E | CCL 77 |
| embryo | P19 | CRL 1825 |
| kidney | RAG | CCL 142 |
| lung | LL/2 | CRL 1642 |
| rectum | CMT-93 | CCL 223 |
| squamous cells | KLN 205 | CRL 1453 |
| stem cells | SCC-PSA1 | CRL 1535 |
| submandibular gland | SCA-9 clone 15 | CRL 1734 |
| testis | F9 | CRL 1720 |
| | NULLI-SCC1 | CRL 1566 |
| thyroid | MTC-M | CRL 1806 |
| rat | | |
| intestine, small | IA-XsSBR | CRL 1677 |
| liver | H4-II-E-C3 | CRL 1600 |
| | McA-RH7777 | CRL 1601 |
| | McA-RH8994 | CRL 1602 |
| | $MH_1C_1$ | CCL 144 |
| mammary | 13762 MAT BIII | CRL 1666 |
| | NMU | CRL 1743 |
| | RBA | CRL 1747 |
| thyroid | 6-23 | CRL 1607 |
| unspecified | LLC-WRC 256 | CCL 38 |
| Chondrosarcoma | | |
| human | SW 1353 | HTB 94 |
| Choriocarcinoma | | |
| human | BeWo | CCL 98 |
| | JAR | HTB 144 |
| | JEG-3 | HTB 36 |
| Desmoid tumor | | |
| human | D422T | CRL 1659 |
| Fibroma | | |
| gerbil, paw | IMR-33 | CCL 146 |
| Fibrosarcoma | | |
| human | Hs 913T | HTB 152 |
| | HT-1080 | CCL 121 |
| | SW684 | HTB 91 |
| mouse | $HSDM_1C_1$ | CCL 148 |
| Glial tumor | | |
| rat | $C_6$ | CCL 107 |

TABLE 2-continued

Tumor Cell Lines

| SOURCE (SPECIES/SITE) OF TUMOR CELL | TUMOR CELL LINE | ATCC ® NO. |
|---|---|---|
| Glioblastoma | | |
| human | U-118 MG | HTB 15 |
| human, brain | A-172 | CRL 1620 |
| | T98G | CRL 1690 |
| | U-87 MG | HTB 14 |
| | U-138 MG | HTB 16 |
| | U-373 MG | HTB 17 |
| Glioma | | |
| human, brain | Hs 683 | HTB 138 |
| Hepatoma | | |
| human | Hep 3B | HB 8064 |
| | Hep G2 | HB 8065 |
| | PLC/PRF/5 | CRL 8024 |
| mouse | Hepa 1-6 | CRL 1830 |
| rat | H4TG | CRL 1578 |
| | H-4-II-E | CRL 1548 |
| | H-4-II-E-C3 | CRL 1600 |
| | McA-RH7777 | CRL 1601 |
| | MvA-RH8994 | CRL 1602 |
| | NH$_1$C$_1$ | CCL 144 |
| | N1-S1 | CRL 1604 |
| | N1-S1 Fudr | CRL 1603 |
| trout | RTH-149 | CRL 1710 |
| Histiocytoma | | |
| human | GCT | TIB 223 |
| Leiomyoblastoma | | |
| human, kidney | G-402 | CRL 1440 |
| Leiomyosarcoma | | |
| hamster, Syrian | DDT$_1$MF-2 | CRL 1701 |
| human | SK-LMS-1 | HTB 88 |
| | SK-UT-1 | HTB 114 |
| | SK-UT-1B | HTB 115 |
| Leukemias & lymphomas | | |
| bovine | BL-3 | CRL 8037 |
| cat | FeLV-3281 | CRL 9116 |
| gibbon, lymphoma | MLA 144 | TIB 201 |
| human: See also Burkitt lymphoma | | |
| blood | 6T-CEM | CRL 8296 |
| | 6T-CEM 20 | CRL 8295 |
| | AGR-ON | CRL 8199 |
| | AML-193 | CRL 9589 |
| | CCRF-CEM | CCL 119 |
| | CCRF-CEM | CRL 8436 |
| | CCRF-HSB-2 | CCL 120.1 |
| | CCRF-SB | CCL 120 |
| | CEM-AG$^R$ | CRL 8081 |
| | CEM-CM3 | TIB 195 |
| | CESS | TIB 190 |
| | DAKIKI | TIB 206 |
| | H9 | HTB 176 |
| | H33HJ-JA1 | CRL 8163 |
| | HEL 92.1.7 | TIB 180 |
| | HL-60 | CCL 240 |
| | HUT 78 | TIB 161 |
| | HUT 102 | TIB 162 |
| | J.RT3-T3.5 | TIB 153 |
| | Jurkat, clone E6-1 | TIB 152 |
| | MJ | CRL 8294 |
| | Mo | CRL 8066 |
| | Mo-B | CCL 245 |
| | MOLT-3 | CRL 1552 |
| | MOLT-4 | CRL 1582 |
| | MV-4-11 | CRL 9591 |
| | Reh | CRL 8286 |
| | RPMI 8226 | CCL 155 |
| | SKW 6.4 | TIB 215 |
| | THP-1 | TIB 202 |
| bone marrow | IM-9 | CCL 159 |
| | KG-1 | CCL 246 |
| | KG-1 | CRL 8031 |
| | KG-1a | CCL 246.1 |
| | RS4; 11 | CRL 1873 |
| cervix | Hs 602 | HTB 142 |
| lymph node | Hs 445 | HTB 146 |
| plasma cells | ARH-77 | CRL 1621 |
| pleural effusion | K-562 | CCL 243 |
| | MC 116 | CRL 1649 |
| | U-937 | CRL 1593 |
| monkey, rhesus | LCL 8664 | CRL 1805 |
| mouse | | |
| bone marrow | M-NFS-60 | CRL 1838 |
| lymph nodes | BC3A | TIB 60 |
| | BC16A | TIB 59 |
| lymphoblast | LBRN-33-1A5 | CRL 8079 |
| | LBRN-33-5A4 | CRL 8080 |
| | LBRM TG6 | CRL 1778 |
| | NFS-1.0 C-1 | CRL 1705 |
| lymphoblast, pre-B | 70Z/3 | TIB 158 |
| | ABE-8.1/2 | TIB 205 |
| | NFS-5 C-1 | CRL 1693 |
| | NFS-25 C-3 | CRL 1695 |
| lymphoblast, pro-B | NFS-70 C-10 | CRL 1694 |
| lymphomas | BW5147.3 (Thy-1$^-$e).10 | TIB 234 |
| | BW5147 (T200$^-$a) 5.2 | TIB 233 |
| | L1210 | CCL 219 |
| | M1 | TIB 192 |
| | NCTC 3749 | CCL 46.1 |
| | P388D$_1$ | CCL 46 |
| | RAW309F.1.1 | TIB 51 |
| | S1A(Thy-1-b) | TIB 231 |
| | WEHI 22.1 | TIB 54 |
| | WR19L | TIB 52 |
| | YAC-1 | TIB 160 |
| lymphomas, B | 2PK-3 | TIB 203 |
| | A20 | TIB 208 |
| | CH1 | TIB 221 |
| | RAW 8.1 | TIB 50 |
| | WEHI-231 | CRL 1702 |
| | WEHI-279 | CRL 1704 |
| | X16C8.5 | TIB 209 |
| lymphomas, pre-B | ABE-8.1/2 | TIB 205 |
| lymphomas, T | BW5147.3 | TIB 47 |
| | BW5147.G.1.4 | TIB 48 |
| | BW5147.G.1.4 OUA$^R$.1 | CRL 1588 |
| | C1498 | TIB 49 |
| | EL4 | TIB 39 |
| | EL4.BU | TIB 40 |
| | EL4.BU.1. OUA$^r$.1.1 | TIB 41 |
| | EL 4.IL-2 | TIB 181 |
| | LBRM-33 clone 4A2 | TIB 155 |
| | R1.1 | TIB 42 |
| | R1E/TL8x.1 | TIB 43 |
| | R1E/TL8x.1. G1.OUA$^r$.1 | TIB 45 |
| | R1.G1 | TIB 44 |
| | S1A.TB.4.8.2 | TIB 27 |
| | S49 (Thy-1-a) | TIB 36 |
| | S49.1 | TIB 28 |
| | S49.1G.3 | TIB 34 |
| | S49.1G.3 PHA. 100/0 | TIB 35 |
| | S49.1H.1AG.6/2 | TIB 29 |
| | S49.1TB.2 | TIB 30 |

TABLE 2-continued

Tumor Cell Lines

| SOURCE (SPECIES/SITE) OF TUMOR CELL | TUMOR CELL LINE | ATCC ® NO. |
|---|---|---|
|  | S49.1TB.4 DEX R.63 | TIB 33 |
|  | TIMI.4 | TIB 37 |
|  | TIMI.4G.1.3 | TIB 38 |
|  | WEHI 7.1 | TIB 53 |
| macrophage-monocytes | J774A.1 | TIB 67 |
|  | P388D$_1$ (IL-1) | TIB 63 |
|  | PU5-1.8 | TIB 61 |
|  | RAW 264.7 | TIB 71 |
|  | RAW 309 Cr.1 | TIB 69 |
|  | WEHI 3 | TIB 68 |
|  | WEHI 265.1 | TIB 204 |
|  | WR19M.1 | TIB 70 |
| myeloblast | M1 | TIB 192 |
| spleen | BB88 | TIB 55 |
|  | BC3A | TIB 60 |
|  | BC16A | TIB 59 |
|  | BCL$_1$ clone 5B$_1$b | TIB 197 |
| subcutaneous | D1B | TIB 56 |
|  | D2N | TIB 58 |
| thymus | L5178Y-R | CRL 1722 |
|  | L5178Y-S | CRL 1723 |
|  | L5178Y TK+/− | CRL 9518 |
| unspecified | BCL$_1$ CW13.20-3B3 | CRL 1669 |
|  | L1210 | CCL 219 |
|  | T27A | TIB 57 |
| rat |  |  |
| basophil | RBL-1 | CRL 1378 |
| lymphoma | C58(NT)D.1.G.OU A$^R$.1 | TIB 236 |
| seal, harbor, lymphoblast | 11B7501 | CRL 1940 |
| Liposarcoma |  |  |
| human | SW872 | HTB 92 |
| Mammary tumor |  |  |
| mouse | C127I | CRL 1616 |
|  | C127:LT | CRL 1804 |
|  | CHM1a | CRL 8399 |
|  | CSMαβ1H | CRL 8401 |
|  | CSMαβ6C | CRL 8400 |
|  | Mm5MT | CRL 1637 |
|  | MMT 060562 | CCL 51 |
| Mastocytoma |  |  |
| mouse | P815 | TIB 64 |
| Medulloblastoma |  |  |
| human | D283 Med | HTB 185 |
|  | D341 Med | HTB 187 |
|  | Daoy | HTB 186 |
|  | TE671 subline 2 | CRL 8805 |
| Melanoma |  |  |
| hamster, Syrian | FF | CRL 1479 |
|  | RPMI 1846 | CCL 49 |
| human | A-375 | CRL 1619 |
|  | A375.S2 | CRL 1872 |
|  | C32 | CRL 1585 |
|  | C32TG | CRL 1579 |
|  | G-361 | CRL 1424 |
|  | HMCB | CRL 9607 |
|  | Hs 294T | HTB 140 |
|  | Hs 695T | HTB 137 |
|  | HT-144 | HTB 63 |
|  | Malme-3M | HTB 64 |
|  | RPMI-7951 | HTB 66 |
|  | SK-MEL-1 | HTB 67 |
|  | SK-MEL-2 | HTB 68 |
|  | SK-MEL-3 | HTB 69 |
|  | SK-MEL-5 | HTB 70 |
|  | SK-MEL-24 | HTB 71 |
|  | SK-MEL-28 | HTB 72 |
|  | SK-MEL-31 | HTB 73 |
|  | WM-115 | CRL 1675 |
|  | WM 266-4 | CRL 1676 |
| mouse | Clone M-3 | CCL 53.1 |
| Myeloma & Plasmacytoma |  |  |
| human | HS-Sultan | CRL 1484 |
|  | IM-9 | CCL 159 |
|  | MC/CAR | CRL 8083 |
|  | MC/CAR-Z2 | CRL 8147 |
|  | NCI-H929 | CRL 9068 |
|  | RPMI 8226 | CCL 155 |
|  | SHM-D33 | CRL 1668 |
|  | SKO-007 | CRL 8033-1 |
|  | SKO-007 clone J3 | CRL 8033-2 |
|  | U266B1 | TIB 196 |
| mouse | 45.6TG1.7 | CRL 1608 |
|  | C1.18.4 | TIB 11 |
|  | FO | CRL 1646 |
|  | FOX-NY | CRL 1732 |
|  | HAZ653-SF | CRL 8714 |
|  | HOPC 1F/12 | TIB 13 |
|  | J558 | TIB 6 |
|  | MOPC-31C | CCL 130 |
|  | MOPC 315 | TIB 23 |
|  | MPC-11 | CCL 167 |
|  | MPC 11 OUA$^r$ | TIB 15 |
|  | P1.17 | TIB 10 |
|  | P3.6.2.8.1 | TIB 8 |
|  | P3/NSI/1-Ag4-1 | TIB 18 |
|  | P3X63Ag8 | TIB 9 |
|  | P3X63-Ag8.653 | CRL 1580 |
|  | P3X63 Ag8U.1 | CRL 1597 |
|  | RPC 5.4 | TIB 12 |
|  | S194/5.XXO-1 | TIB 19 |
|  | S194/5.XXO.BU.1 | CRL 8837 |
|  | 5194/5.XXO.BU.1 | TIB 20 |
|  | SHM-D33 | CRL 1668 |
|  | Sp2/0-Ag14 | CRL 1581 |
|  | 5p2/0-Ag14 | CRL 8287 |
|  | XC 1.5/51 | TIB 16 |
|  | XS63 | TIB 17 |
| rat | YB2/0 | CRL 1662 |
|  | Y3-Ag.1.2.3 | CRL 1631 |
| Neuroblastoma |  |  |
| human | IMR-32 | CCL 127 |
|  | SK-N-MC | HTB 10 |
|  | SK-N-SH | HTB 11 |
| mouse | NB41A3 | CCL 147 |
|  | Neuro-2a | CCL 131 |
| Neuroglioma |  |  |
| human, brain | H4 | HTB 148 |
| Osteogenic sarcoma |  |  |
| cat | FC25T | CRL 6090 |
| dog | D-17 | CCL 183 |
|  | D17 | CRL 8468 |
| human | 143B | CRL 8303 |
|  | 143B PML BK TK | CRL 8304 |
|  | G-292, cl A141B1 | CRL 1423 |
|  | HOS | CRL 1543 |
|  | KHOS-240S | CRL 1545 |
|  | KHOS-312H | CRL 1546 |
|  | KHOS/NP | CRL 1544 |
|  | MG-63 | CRL 1427 |
|  | MNNG/HOS | CRL 1547 |
|  | Saos-2 | HTB 85 |
|  | SK-ES-1 | HTB 86 |
|  | U-2 OS | HTB 96 |
| rat | UMR-106 | CRL 1661 |

TABLE 2-continued

Tumor Cell Lines

| SOURCE (SPECIES/SITE) OF TUMOR CELL | TUMOR CELL LINE | ATCC ® NO. |
|---|---|---|
| | UMR-108 | CRL 1663 |
| Pancreatic tumor | | |
| rat | AR42J | CRL 1492 |
| | ARIP | CRL 1674 |
| Pheochromocytoma | | |
| rat | PC-12 | CRL 1721 |
| Pituitary tumor | | |
| mouse | AtT-2/D16v-F2 | CRL 1795 |
| | AtT-20 | CCL 89 |
| rat | $GH_1$ | CCL 82 |
| | $GH_3$ | CCL 82.1 |
| Plasmacytoma: See Myeloma | | |
| Retinoblastoma | | |
| human | WERI-Rb-1 | HTB 169 |
| | Y79 | HTB 18 |
| Rhabdomyosarcoma | | |
| human | A-204 | HTB 82 |
| | A-673 | CRL 1598 |
| | Hs729 | HTB 153 |
| | RD | CCL 136 |
| Sarcoma | | |
| bovine | BL-3 | CRL 8037 |
| dog | D-17 | CCL 183 |
| | D-17 | CRL 8468 |
| gibbon | UCD-MLA-144 | HB 8370 |
| hamster | $DDT_1$ MF-2 | CRL 1701 |
| human | 143B | CRL 8303 |
| | 143B PML BK TK | CRL 8304 |
| | A-204 | HTB 82 |
| | A673 | CRL 1598 |
| | G-292, clone A141B1 | CRL 1423 |
| | HOS | CRL 1543 |
| | Hs 729 | HTB 153 |
| | Hs 913T | HTB 152 |
| | HT-1080 | CCL 121 |
| | KHOS-240S | CRL 1545 |
| | KHOS-312H | CRL 1546 |
| | KHOS/NP | CRL 1544 |
| | MG-63 | CRL 1427 |
| | MNNG/HOS | CRL 1547 |
| | RD | CCL 136 |
| | RD-ES | HTB 166 |
| | Saos-2 | HTB 85 |
| | SK-ES-1 | HTB 86 |
| | SK-LMS-1 | HTB 88 |
| | SK-UT-1 | HTB 114 |
| | SK-UT-1B | HTB 115 |
| | SW684 | HTB 91 |
| | SW872 | HTB 92 |
| | SW982 | HTB 93 |
| | SW1353 | HTB 94 |
| | U-2 OS | HTB 96 |
| mouse | CCRF S-180 II | CCL 8 |
| | $HSDM_1C_1$ | CCL 148 |
| | MB III | CCL 32 |
| | Sarcoma 180 | T1B 66 |
| | WEHI 164 | CRL 1751 |
| quail | QT6 | CRL 1708 |
| rat | Jensen Sarcoma | CCL 45 |
| | RR1022 | CCL 47 |
| | UMR-106 | CRL 1661 |
| | UMR-108 | CRL 1663 |
| | XC | CCL 165 |
| Teratoma | | |
| mouse | XB-2 | CL 177 |
| | XBF | CRL 8808 |
| Testicular tumor, Leydig cell | | |
| mouse | I-10 | CCL 83 |
| rat | LC-540 | CCL 43 |
| | R2C | CCL 97 |
| Thymoma | | |
| mouse | AKR1.G.1.OUA$^R$.1.26 | TIB 232 |
| | R1.1 | TIB 42 |
| Wilms' tumor | | |
| human | G-401 | CRL 1441 |
| | SK-NEP-1 | HTB 48 |
| METASTATIC TUMORS | | |
| dog | | |
| to lung | D-17 | CCL 183 |
| human | | |
| to abdominal wall | NCI-H508 | CCL 253 |
| to adrenal gland | NCI-H510A | HTB 184 |
| to bone | Hs 696 | HTB 151 |
| to bone marrow | SK-N-SH | HTB 11 |
| to brain | DU 145 | HTB 81 |
| | MDA-MB-361 | HTB 27 |
| to Fallopian tube | Caov-4 | HTB 76 |
| to leg | Hs 746T | HTB 135 |
| to liver | Capan-1 | HTB 79 |
| | CFPAC-1 | CRL 1918 |
| | SU.86.86 | CRL 1837 |
| to lung | GCT | TIB 223 |
| | Hs 888Lu | CCL 211 |
| | Hs 913T | HTB 152 |
| | Malme-3M | HTB 64 |
| | T84 | CCL 248 |
| | Tera-1 | HTB 105 |
| | Tera-2 | HTB 106 |
| to lymph node | AN3 CA | HTB 111 |
| | BT-549 | HTB 122 |
| | Cates-1B | HTB 104 |
| | Hs 294T | HTB 140 |
| | Hs 695T | HTB 137 |
| | Hs 766T | HTB 134 |
| | HT-3 | HTB 32 |
| | KATO III | HTB 103 |
| | LNCaP.FGC | CRL 1740 |
| | MS 751 | HTB 34 |
| | NCI-H292 | CRL 1848 |
| | NCI-H747 | CCL 252 |
| | NCI-H820 | HTB 181 |
| | RPMI-7951 | HTB 66 |
| | SK-MEL-1 | HTB 67 |
| | SK-MEL-3 | HTB 69 |
| | SK-MEL-5 | HTB 70 |
| | SK-MEL-24 | HTB 71 |
| | SW620 | CCL 227 |
| | SW962 | HTB 118 |
| to mesentery | CaSki | CRL 1550 |
| to omentum | ME-180 | HTB 33 |
| to pelvis | Hs 700T | HTB 147 |
| to peritoneal fluid | RF-48 | CRL 1863 |
| to peritoneum | D283 Med | HTB 185 |
| | NCI-H498 | CCL 254 |
| to pleura | Calu-1 | HTB 54 |
| to skin | Caki-1 | HTB 46 |
| | DU 4475 | HTB 123 |
| | SK-MEL-2 | HTB 68 |
| to subcutaneous tissue | ChaGo K-1 | HTB 168 |
| | HT-144 | HTB 63 |
| to supraclavicular region | LoVo | CCL 229 |
| to supra-orbit | SK-N-MC | HTB 10 |

TABLE 2-continued

Tumor Cell Lines

NAVAL BIOSCIENCES LABORATORY (NBL) ANIMAL CANCER CELL LINES

| SOURCE (SPECIES/SITE) OF TUMOR CELL | TUMOR CELL LINE | ATCC ® NO. |
|---|---|---|
| Bladder | | |
| mouse | MM45T.B1 | CRL 6420 |
| Bone | | |
| dog | D17 | CRL 6248 |
| | D22 | CRL 6250 |
| | D39 | CRL 6251 |
| Bone marrow | | |
| bovine | LB9.Bm | CRL 6053 |
| | LB10.Bm | CRL 6060 |
| Carcinoma | | |
| rabbit, cottontail | Oc4T/cc | CRL 6501 |
| Connective tissue | | |
| arm/shoulder | | |
| cat | FC94.T | CRL 6113 |
| dog | CF21.T | CRL 6220 |
| mouse | MM36T(A) | CRL 6410 |
| parakeet | MU27 | CRL 6487 |
| head/face | | |
| dog | CF11.T | CRL 6217 |
| | CF15.T | CRL 6218 |
| leg/hip | | |
| cat | FC77.T | CRL 6105 |
| | FC81.T | CRL 6108 |
| dog | CF17.T | CRL 6219 |
| mouse | MM36T(C) | CRL 6411 |
| | MM47T | CRL 6424 |
| trunk | | |
| cat | FC100.T | CRL 6115 |
| dog | CF24.T | CRL 6221 |
| mouse | MM37T | CRL 6414 |
| parakeet | MU12.T | CRL 6483 |
| Connective and soft tissue | | |
| mouse | +/+ SCT | CRL 6469 |
| Fibrosarcoma | | |
| cat | FC65.T | CRL 6084 |
| | FC65.T | CRL 6100 |
| mouse | MM43T | CRL 6418 |
| | MM46T | CRL 6423 |
| | MM48T | CRL 6425 |
| | MM49T | CRL 6426 |
| Interscapular region | | |
| bat, mouse-eared | Mvi/It | CRL 6012 |
| Liver | | |
| mouse | MM45T.Li | CRL 6421 |
| Lung | | |
| mouse | Mad/C1 | CRL 6366 |
| | Mad/C3 | CRL 6367 |
| Lymph node | | |
| bovine | 2FLB.Ln | CRL 6045 |
| | 2LBLN | CRL 6047 |
| | 3LBLN | CRL 6048 |
| | 5LBLN | CRL 6049 |
| | 6LBLN | CRL 6050 |
| | 7LBLN | CRL 6051 |
| | LB9.Ln | CRL 6057 |
| | LB10.Ln | CRL 6062 |
| | LB11.Ln | CRL 6066 |
| | LBLN | CRL 6046 |
| | R2LBLN | CRL 6070 |
| cat | F8 | CRL 6074 |
| | LFC16.Ln | CRL 6173 |
| dog | CLN | CRL 6245 |
| Lymph node, head/neck | | |
| cat | F₁B | CRL 6168 |
| Lymphoma | | |
| cat | FC11.BM | CRL 6088 |
| | FC11th | CRL 6089 |
| Mammary gland | | |
| dog | CF29.Mg | CRL 6224 |
| | CF33.Mg | CRL 6227 |
| | CF34.Mg | CRL 6228 |
| | CF35.Mg | CRL 6229 |
| | CF41.Mg | CRL 6232 |
| | CF42.Mg | CRL 6233 |
| | CF45B.Mg | CRL 6237 |
| | CF51.Mg/L1 | CRL 6242 |
| | CF51.Mg/L3 | CRL 6243 |
| monkey, rhesus | CMMT | CRL 6299 |
| | CMMT 110/C1 | CRL 6300 |
| | Mel III | CRL 6308 |
| mouse | B-29 | CRL 6325 |
| | B-63 | CRL 6326 |
| | CCL-51 | CRL 6337 |
| | L-8A | CRL 6363 |
| | MM2MT | CRL 6373 |
| | MM2MTC | CRL 6374 |
| | MM2SCT | CRL 6375 |
| | MM5MT | CRL 6590 |
| | MM5MTC | CRL 6378 |
| | MM5MTM | CRL 6379 |
| | MM5/C1 | CRL 6444 |
| | MM5.1 | CRL 6380 |
| | MM36T(B) | CRL 6412 |
| | RIIIMT | CRL 6449 |
| | +/+ MGT | CRL 6468 |
| rat | MTW9A | CRL 6597 |
| | Rn1T | CRL 6598 |
| | Rn2Nod | CRL 6600 |
| | Rn2T | CRL 6599 |
| | SMT/2A LNM | CRL 6602 |
| Mastocytoma | | |
| mouse | P815 MB | CRL 6448 |
| Melanoma | | |
| mouse | B16-F0 | CRL 6322 |
| | B16-F1 | CRL 6323 |
| Papilloma | | |
| rabbit, domestic | CTPS | CRL 6496 |
| | OcT2(Vx7) | CRL 6594 |
| Pleural fluid | | |
| seal, harbor | PV1.P1 | CRL 6526 |
| Retroperitoneum | | |
| parakeet | MU13.T | CRL 6484 |
| Sarcoma | | |
| rat | XC | CRL 6603 |
| Spleen | | |
| bovine | LB9.Sp | CRL 6058 |
| | LB10.Sp | CRL 6063 |
| | LB11.Sp | CRL 6067 |
| cat | FC81.Sp | CRL 6107 |
| mouse | NM45T.Sp | CRL 6422 |

TABLE 2-continued

Tumor Cell Lines

| SOURCE (SPECIES/SITE) OF TUMOR CELL | TUMOR CELL LINE | ATCC ® NO. |
|---|---|---|
| Spleen/thymus/bone marrow pool | | |
| bovine | LB9.Sp/Thy/Bm | CRL 6052 |
| cat | FC83.Res | CRL 6567 |
| Thymus | | |
| bovine | LB9.Thy | CRL 6059 |
|  | LB10.Thy | CRL 6064 |
|  | LB11.Thy | CRL 6068 |
| cat | FC81.Thy | CRL 6109 |
|  | FC95.Thy | CRL 6114 |
| Thymus, erythroleukemia | | |
| cat | F25 | CRL 6566 |
| Unknown | | |
| mouse | MM14.OT | CRL 6384 |
|  | MM15.OT | CRL 6438 |
|  | MM52.T | CRL 6429 |
|  | MM53.T | CRL 6431 |
| parakeet | MU10 | CRL 6481 |
| rabbit, domestic | VX7 | CRL 6504 |
| rat | Rn6T | CRL 6601 |
| Unknown, DMDA-induced | | |
| rat | 1255/B7 | CRL 6604 |

TABLE 3

Human Tumor Cell Lines

| ATTC HTB NUMBER | CELL LINE | TUMOR TYPE |
|---|---|---|
| 1 | J82 | Transitional-cell carcinoma, bladder |
| 2 | RT4 | Transitional-cell papilloma, bladder |
| 3 | ScaBER | Squamous carcinoma, bladder |
| 4 | T24 | Transitional-cell carcinoma, bladder |
| 5 | TCCSUP | Transitional-cell carcinoma, bladder, primary grade IV |
| 9 | 5637 | Carcinoma, bladder, primary |
| 10 | SK-N-MC | Neuroblastoma, metastasis to supra-orbital area |
| 11 | SK-N-SH | Neuroblastoma, mietastasis to bone marrow |
| 12 | SW 1088 | Astrocytoma |
| 13 | SW 1783 | Astrocytoma |
| 14 | U-87 MG | Glioblastoma, astrocytoma, grade III |
| 15 | U-118 MG | Glioblastoma |
| 16 | U-138 MG | Glioblastoma |
| 17 | U-373 MG | Glioblastoma, astrocytoma, grade III |
| 18 | Y79 | Retinoblastoma |
| 19 | BT-20 | Carcinoma, breast |
| 20 | BT-474 | Ductal carcinoma, breast |
| 22 | MCF7 | Breast adenocarcinoma, pleural effusion |
| 23 | MDA-MB-134-VI | Breast, ductal carcinoma, pleural effusion |
| 24 | MDA-MD-157 | Breast medulla, carcinoma, pleural effusion |
| 25 | MDA-MB-175-VII | Breast, ductal carcinoma, pleural effusion |
| 27 | MDA-MB-361 | Adenocarcinoma, breast, metastasis to brain |
| 30 | SK-BR-3 | Adenocarcinoma, breast, malignant pleural effusion |
| 31 | C-33 A | Carcinoma, cervix |
| 32 | HT-3 | Carcinoma, cervix, metastasis to lymph node |
| 33 | ME-180 | Epidermoid carcinoma, cervix, metastasis to omentum |

TABLE 3-continued

Human Tumor Cell Lines

| ATTC HTB NUMBER | CELL LINE | TUMOR TYPE |
|---|---|---|
| 34 | MS751 | Epidermoid carcinoma, cervix, metastasis to lymph node |
| 35 | SiHa | Squamous carcinoma, cervix |
| 36 | JEG-3 | Choriocarcinoma |
| 37 | Caco-2 | Adenocarcinoma, colon |
| 38 | HT-29 | Adenocarcinoma, colon, moderately well-differentiated grade II |
| 39 | SK-CO-1 | Adenocarcinoma, colon, ascites |
| 40 | HuTu 80 | Adenocarcinoma, duodenum |
| 41 | A-253 | Epidermoid carcinoma, submaxillary gland |
| 43 | FaDu | Squamous cell carcinoma, pharynx |
| 44 | A-498 | Carcinoma, kidney |
| 45 | A-704 | Adenocarcinoma, kidney |
| 46 | Caki-1 | Clear cell carcinoma, consistent with renal primary, metastasis to skin |
| 47 | Caki-2 | Clear cell carcinoma, consistent with renal primary |
| 48 | SK-NEP-1 | Wilms' tumor, pleural effusion |
| 49 | SW 839 | Adenocarcinoma, kidney |
| 52 | SK-HEP-1 | Adenocarcinoma, liver, ascites |
| 53 | A-427 | Carcinoma, lung |
| 54 | Calu-1 | Epidermoid carcinoma grade III, lung, metastasis to pleura |
| 55 | Calu-3 | Adenocarcinoma, lung, pleural effusion |
| 56 | Calu-6 | Anaplastic carcinoma, probably lung |
| 57 | SK-LU-1 | Adenocarcinoma, lung consistent with poorly differentiated, grade III |
| 58 | SK-MES-1 | Squamous carcinoma, lung, pleural effusion |
| 59 | SW 900 | Squamous cell carcinoma, lung |
| 60 | EB1 | Burkitt lymphoma, upper maxilia |
| 61 | EB2 | Burkitt lymphoma, ovary |
| 62 | P3HR-1 | Burkitt lymphoma, ascites |
| 63 | HT-144 | Malignant melanoma, metastasis to subcutaneous tissue |
| 64 | Malme-3M | Malignant melanoma, metastasis to lung |
| 66 | RPMI-7951 | Malignant melanoma, metastasis to lymph node |
| 67 | SK-MEL-1 | Malignant melanoma, metastasis to lymphatic system |
| 68 | SK-MEL-2 | Malignant melanoma, metastasis to skin of thigh |
| 69 | SK-MEL-3 | Malignant melanoma, metastasis to lymph node |
| 70 | SK-MEL-5 | Malignant melanoma, metastasis to axillary node |
| 71 | SK-MEL-24 | Malignant melanoma, metastasis to node |
| 72 | SK-MEL-28 | Malignant melanoma |
| 73 | SK-MEL-31 | Malignant melanoma |
| 75 | Caov-3 | Adenocarcinoma, ovary, consistent with primary |
| 76 | Caov-4 | Adenocarcinoma, ovary, metastasis to subserosa of fallopian tube |
| 77 | SK-OV-3 | Adenocarcinoma, ovary, malignant ascites |
| 78 | SW 626 | Adenocarcinoma, ovary |
| 79 | Capan-1 | Adenocarcinoma, pancreas, metastasis to liver |
| 80 | Capan-2 | Adenocarcinoma, pancrease |
| 81 | DU 145 | Carcinoma, prostate, metastasis to brain |
| 82 | A-204 | Rhabdomyosarcoma |
| 85 | Saos-2 | Osteogenic sarcoma, primary |
| 86 | SK-ES-1 | Anaplastic osteosarcoma versus Ewing sarcoma, bone |
| 88 | SK-LNS-1 | Leiomyosarcoma, vulva, primary |
| 91 | SW 684 | Fibrosarcoma |
| 92 | SW 872 | Liposarcoma |
| 93 | SW 982 | Axilla synovial sarcoma |
| 94 | SW 1353 | Chondrosarcoma, humerus |
| 96 | U-2 OS | Osteogenic sarcoma, bone primary |
| 102 | Malme-3 | Skin fibroblast |
| 103 | KATO III | Gastric carcinoma |

TABLE 3-continued

Human Tumor Cell Lines

| ATTC HTB NUMBER | CELL LINE | TUMOR TYPE |
|---|---|---|
| 104 | Cate-1B | Embryonal carcinoma, testis, metastasis to lymph node |
| 105 | Tera-1 | Embryonal carcinoma, malignancy consistent with metastasis to lung |
| 106 | Tera-2 | Embryonal carcinoma, malignancy consistent with, metastasis to lung |
| 107 | SW579 | Thyroid carcinoma |
| 111 | AN3 CA | Endometrial adenocarcinoma, metastatic |
| 112 | HEC-1-A | Endometrial adenocarcinoma |
| 113 | HEC-1-B | Endometrial adenocarcinoma |
| 114 | SK-UT-1 | Uterine, mixed mesodermal tumor, consistent with leiomyosarcoma grade III |
| 115 | SK-UT-1B | Uterine, mixed mesodermal tumor, consistent with leiomyosarcoma grade III |
| 117 | SW 954 | Squamous cell carcinoma, vulva |
| 118 | SW 962 | Carcinoma, vulva, lymph node metastasis |
| 119 | NCI-H69 | Small cell carcinoma, lung |
| 120 | NCI-H128 | Small cell carcinoma, lung |
| 121 | BT-483 | Ductal carcinoma, breast |
| 122 | BT-549 | Ductal carcinoma, breast |
| 123 | DU4475 | Metastatic cutaneous nodule, breast carcinoma |
| 124 | HBL-100 | Breast |
| 125 | Hs 578Bst | Breast, normal |
| 126 | Hs 578T | Ductal carcinoma, breast |
| 127 | MDA-MB-330 | Carcinoma, breast |
| 128 | MDA-MB-415 | Adenocarcinoma, breast |
| 129 | MDA-MB-435S | Ductal carcinoma, breast |
| 130 | MDA-MB-436 | Adenocarcinoma, breast |
| 131 | MDA-MB-453 | Carcinoma, breast |
| 132 | MDA-MB-468 | Adenocarcinoma, breast |
| 133 | T-47D | Ductal carcinoma, breast, pleural effusion |
| 134 | Hs 766T | Carcinoma, pancreas, metastatic to lymph node |
| 135 | Hs 746T | Carcinoma, stomach, metastatic to left leg |
| 137 | Hs 695T | Amelanotic melanoma, metastatic to lymph node |
| 138 | Hs 683 | Glioma |
| 140 | Hs 294T | Melanoma, metastatic to lymph node |
| 142 | Hs 602 | Lymphoma, cervical |
| 144 | JAR | Choriocarcinoma, placenta |
| 146 | Hs 445 | Lymphoid, Hodgkin's disease |
| 147 | Hs 700T | Adenocarcinoma, metastatic to pelvis |
| 148 | H4 | Neuroglioma, brain |
| 151 | Hs 696 | Adenocarcinoma primary, unknown, metastatic to bone-sacrum |
| 152 | Hs 913T | Fibrosarcoma, metastatic to lung |
| 153 | Hs 729 | Rhabdomyosarcoma, left leg |
| 157 | FHs 738Lu | Lung, normal fetus |
| 158 | FHs 173We | Whole embryo, normal |
| 160 | FHs 738B1 | Bladder, normal fetus |
| 161 | NIH:OVCAR-3 | Ovary, adenocarcinoma |
| 163 | Hs 67 | Thymus, normal |
| 166 | RD-ES | Ewing's sarcoma |
| 168 | ChaGo K-1 | Bronchogenic carcinoma, subcutaneous metastasis, human |
| 169 | WERI-Rb-1 | Retinoblastoma |
| 171 | NCI-H446 | Small cell carcinoma, lung |
| 172 | NCI-H209 | Small cell carcinoma, lung |
| 173 | NCI-H146 | Small cell carcinoma, lung |
| 174 | NCI-H441 | Papillary adenocarcinoma, lung |
| 175 | NCI-H82 | Small cell carcinoma, lung |
| 176 | H9 | T-cell lymphoma |
| 177 | NCI-H460 | Large cell carcinoma, lung |
| 178 | NCI-H596 | Adenosquamous carcinoma, lung |
| 179 | NCI-H676B | Adenocarcinoma, lung |
| 180 | NCI-H345 | Small cell carcinoma, lung |
| 181 | NCI-H820 | Papillary adenocarcinoma, lung |
| 182 | NCI-H520 | Squamous cell carcinoma, lung |
| 183 | NCI-H661 | Large cell carcinoma, lung |
| 184 | NCI-H510A | Small cell carcinoma, extra-pulmonary origin, metastatic |
| 185 | D283 Med | Medulloblastoma |
| 186 | Daoy | Medulloblastoma |
| 187 | D341 Med | Medulloblastoiua |
| 188 | AML-193 | Acute monocyte leukemia |
| 189 | MV4-11 | Leukemia biphenotype |

In addition to Tables 2 and 3, if a particular cell type is desired, the means for obtaining such cells will be known to those of skill in the particular art. For example, regarding osteosarcoma cell lines, the rat osteosarcoma cell lines OSR-6, OSR4TR1, OSR3TR1, OSR-2 and OSR-8 are known to be available (ATCC Accession Nos. CRL 11069, 11067, 11066, 11065, 11070; U.S. Pat. Nos. 5,292,656; 5,288,628; 5,286,645; 5,286,644; 5,286,643). An analysis of the scientific literature will thus readily reveal an appropriate choice of cell for any general type desired to be used.

C. Intracellular Antigens

Studies are presented herein to show that the conjugation methods of the invention result in the intracellular incorporation of adjuvants (e.g., Example 8). Intracellular incorporation is expected to occur at all temperatures and to be increased at physiological temperatures. The intracellular uptake of adjuvants by cells, particularly tumor cells, is important from the point of view of antigen presentation to T cells and B cells.

During antigen presentation by macrophages or dendritic cells, antigens are degraded in endocytoplasmic reticulum and presented on the surface of the antigen presenting cells in conjunction with MHC class I or II. During presentation in other cells, antigens, such as tumor antigens and viral antigens, are processed and presented largely in conjunction with MHC class I. Antigen presentation generally needs co-stimulatory molecules which will promote effective antigen presentation to T and B cells, as well as stimulate T and B cells leading to their clonal proliferation. In cancer patients, the immune system is greatly suppressed under these conditions and likely needs further promotion or more effective co-stimulation.

An adjuvant incorporated onto the tumor cell surface is expected to act as a co-stimulatory molecule. Using the membrane-adjuvant cells of the invention this co-stimulation is evidently provided for tumor antigens in the membrane. However, this alone would not particularly clearly allow for enhanced immune responses against internal antigens.

Intracellularly incorporated adjuvants, as also provided by this invention, would be expected to act as effective immunostimulators to internal antigens. In this case, an adjuvant that has been internalized will act as a co-stimulatory molecule, most likely as a result of internal processing with the intracellular antigens. This is another advantage of the invention, as many relevant tumor antigens are intracellular. For example, it is known that in human melanoma, tumor associated antigens such as Mage I are cytosolic and may not be located on the cell surface. Further intracellular antigens are shown in Table 12.

D. Engineered Cells

Where an anti-tumor response is desired using the methods of the invention, there is no actual requirement for unmodified tumor cells themselves to be used. Rather, cells that have been modified or engineered to contain membrane accessible tumor antigens may be employed. Such cells may be of virtually any origin, so long as they have been manipulated to express one or more tumor antigens. Expression of tumor antigens can also be achieved by virtually any method, such as, e.g., by admixing the antigens or proteins into the membrane; by fusing tumor cell membrane preparations with the cells; by fusing liposomes containing tumor antigens with the cells; by expressing a recombinant DNA segment encoding a tumor antigen in a cell, and the like.

These techniques allow for one or more cells, or a cocktail of cells, to be prepared and their tumor antigen content generally controlled. Tumor antigens can thus be expressed, or over-expressed as predominant antigens, in cell types that do not normally contain such cells. Additional tumor antigens can also be added to an existing tumor cell, or a previously engineered cell, to provide a "multi-antigen cell".

Many tumor antigens are known in the art that can be utilized in this way. For example, the antigen termed TAG 72 and the HER-2 proto-oncogene protein are selectively found on the surfaces of many breast, lung and colorectal cancers (Thor et al., 1986; Colcher et al., 1987; Shepard et al., 1991). The milk mucin core protein and human milk fat globule, as recognized by the antibodies MOv18 and OV-TL3 (Miotti et al., 1985; Burchell et al., 1983); and the high $M_r$ melanoma antigens that bind to the antibody 9.2.27 (Reisfeld et al., 1982) are further examples.

Furthermore, the invention can also be used to insert additional useful molecules into the cells, including tumor cells. In particular, tumor cells may be modified or engineered to include other membrane proteins that are believed to increase specific or non-specific anti-tumor responses. Expression of additional molecules may be achieved by admixing proteins into the membrane, by fusion, or by recombinant expression. Immunologically relevant molecules, such as different MHC class I or MHC class II antigens, may be used in this context.

More particularly, a defined target molecule may be included in the membrane of the adjuvant-cell to increase subsequent adverse reactions against the target cells of an animal. A currently preferred example is the addition of fibronectin in combination with an adjuvant to irradiated bladder cancer cells for use in bladder cancer treatment.

The rationale for the bladder cancer treatment aspect of this invention is based on the following analyses. The common cancer 'vaccine' or therapeutic often contains two components: (1) irradiated tumor cells, allogenic or autologous; and (2) a bacterial stimulant, such as BCG or *Cornybacterium parvum* (Morton and Ravindranath, 1992). The observations of Ravindranath et al. (1994a and 1994b) indicates that the association between tumor cells and bacteria increases the immune response. When BCG is used as an immunostimulator, it is mixed with tumor cells and administered intradermally (Morton et al., 1992). There is no clear documentation of direct binding of the bacterium on to tumor cell surface. The bacterium may or may not bind.

BCG alone is useful in treating superficial bladder cancer patients (Lamm et. al., 1991). The prognosis is generally believed to better when bacteria adhere to the tumor (Akaza et. al., 1993). Further analysis has revealed that the bacteria bind in the tumors which contain more adhesive molecules, such as fibronectin (Cheng et. al., 1994; Fleischmann et. al., 1993) and ICAM-1 (Jackson et. al., 1994; Campbell et. al., 1994).

Based on the bladder cancer studies and the principles described in this application (see, e.g., Example 8), it is contemplated that adhesive molecules, such as fibronectin and ICAM-1, may be incorporated onto the cell surface to enable attachment of bacteria, such as BCG, on to tumor cell surfaces to improve the efficacy of the tumor cell vaccine.

IV. Melanoma Cells

The melanoma cell vaccine referred to as "MCV", developed by one of the present inventors, may be employed in the present invention. This vaccine consists of three allogeneic melanoma cell lines that are known to contain effective concentrations of six melanoma associated antigens (MAA). These MAAs have been demonstrated to be immunogenic in melanoma patients. The MAAs include three gangliosides, GD2, GM2 and O-acetyl GD3; and three protein antigens, the lipoprotein M-TAA, and the two glycoproteins M-fetal antigen and M-urinary antigen.

The three human melanoma cell lines used in MCV are M10, M24, and M101, which were selected from a series of melanoma cell lines after careful examination for the high expression of MAA immunogenic in melanoma patients. These MCV cells are grown and prepared for administration as described in Morton et al. (1993) and in U.S. patent application Ser. No. 07/961/786, filed Oct. 15, 1992, incorporated herein by reference.

Other melanoma cell lines that may be used include M27, M18, M14, M111, M22, M7, M102, M108, M16, M104, M109, M25, and even M112, M21 and M15 (Tsuchida et al., 1989). Still further melanoma cell lines, established and characterized at the John Wayne Cancer Institute (JWCI), include M12, Mke, Mst, Mmu, Mka, and Mkn. These may also be employed in the present invention. Preferred cell lines will generally be selected from those described herein and by Morton et al. (1992; 1993).

Furthermore, the qualitative and quantitative pattern of ganglioside antigen expressed by cell lines, may be modified, by adjusting the culture conditions. Tsuchida et al. (1987; 1989) studied the pattern of gangliosides in human melanoma tumor cells, directly obtained after surgery, after growing them in culture and after implanting them in immuno-deficient mice (called nude mice). The ganglioside pattern changed after growing the tumor cells in culture. Interestingly, the pattern reverts back to the original tumor condition after implanting and growing into nude mice. Reestablishment of the original ganglioside patterns after growing in nude mice demonstrates that in vivo expression of gangliosides on tumor cell surface is conserved and stable, whereas growing them in culture conditions may alter their synthesis and expression. This fact is important for developing cell lines for vaccine immunotherapy.

The MAA antigens of the MCV, developed by one of the present inventors, are located on the cell surface, and antibodies to them have been shown to bind with complement and kill melanoma cells in vitro (Sidell et al., 1979; Irie et al., 1989;). Immunization of patients with MCV containing these antigens induces specific immune responses to the MAA (Ravindranath et al., 1989; Euhus et al., 1989). The presence of antibodies to those MAA in melanoma patients who were not treated with the vaccine was found to correlate with survival, indicating that these MAAs are important in the natural history of melanoma and in modulating the host protective immune responses against this disease (Jones et al., 1981).

As the antigens in the MCV are present at the cell surface, and as antibodies to MAA both kill melanoma cells and correlate with survival, the MCV is an ideal vehicle for use in the present invention. Furthermore, as the MCV vaccine has been used in Phase II clinical trials, it has already been proven to be safe for human administration. Indeed, patients receiving this vaccine have survived significantly longer than patients previously treated with other regimens of immunotherapy or chemotherapy and, when compared to previous trials, MCV was found to be significantly more effective in eliciting specific humoral and cell-mediated immune responses.

As stated in section VII, MCV containing adjuvants in the cell membrane will also be useful for active immunotherapy in other types of human cancer, since five of the six tumor associated antigens found in the MCV compositions are also present in other types of human neoplasms. The lipoprotein antigen (180 kd) is the only one whose distribution is restricted to melanoma that has not, at the present time, been shown to induce antibodies that cross-react with other types of human neoplasms.

The sources of a variety of other melanoma cells that may be used in this invention are known. For example, U.S. Pat. Nos. 5,194,384 and 5,030,621, each incorporated herein by reference, concern methods for preparing cell-free vaccines that require the culture of human cancer cells. The same cells could be employed in this invention.

In the case of melanoma, it is believed that those patients who respond well to active immunotherapy have a high level of anti-ganglioside IgM that acts to clear the shed gangliosides. In contrast, in non- or poor-responders, the level of the tumor derived gangliosides is believed to be too high, or the level of anti-ganglioside antibodies too low, resulting in failure to reduce or eliminate the shed gangliosides.

In the treatment of melanoma, the adjuvant-incorporated cell tumor cell compositions disclosed herein would function to augment antibody production and then, as a sequel to the formation of antibodies, the shed gangliosides would be cleared from circulation and immunocompetence restored. The combined adjuvant-incorporated tumor cell formulation thus has a dual and perpetuating role, i.e., attacking tumor cells by way of antibody binding to their surface antigens, and removing shed antigens from the blood to prevent competition for antibody binding.

V. Immune System Stimulation and Antibody Generation

In addition to its use as a therapeutic agent, it should not be overlooked that cellular-adjuvant combinations, such as MPL linked to cells, will be of great use in augmenting T cell and antibody production against antigens, especially of antibodies against membrane antigens that are immunologically cryptic. This will be useful for the large-scale production of antigen-specific T cells, and human and mouse polyclonal and monoclonal antibodies, such as the anti-ganglioside antibodies described herein.

The standard methods for generating T cells and polyclonal and monoclonal antibodies (MAbs) can now be manipulated to promote an antibody response against an immunologically cryptic antigen (or antigens), or to increase the response against a less effective immunogen. The contribution of the invention lies in providing improved immunizing compositions in which an adjuvant, such as, for example, MPL, is incorporated into, or otherwise associated with, the outer membrane of a cell. Once such an immunogenic composition has been obtained, the standard methods for T cell and antibody generation can then be employed.

For example, to prepare a polyclonal antibody in accordance with the present invention, one uses an immunogenic cellular composition, e.g., a tumor cell having an outer membrane antigen against which one wishes to raise an antibody, which cell also includes, in the same membrane, an adjuvant. One then immunizes an animal with an effective amount of the immunogenic adjuvant-incorporated cell composition. The generation of MAbs following on from an initial immunization is also routine, is described in the scientific literature, and also detailed herein in Example 6.

Immunologically effective amounts are those amounts that result in antibody production, and preferably, those that result in an acceptable titre of antibodies. The data in Example 2, Example 3 and Example 4 clearly indicate the effectiveness of adjuvants when incorporated into cellular membranes containing the target immunogen. Immunologically effective amounts of gangliosides are described in the literature, such as in U.S. Pat. No. 5,102,663 that describes a vaccine for stimulating or enhancing the production of antibodies directed against 9-O-acetyl GD3 ganglioside. The amounts of purified ganglioside and ganglioside mixtures used effectively in U.S. Pat. No. 5,102,663 can be used in combination with the data given herein to assist in the determination of the most appropriate immunological dose.

Immunologically effective amounts that result in antibody production, or even that result in an anti-tumor effect, will be readily determinable. Although not believed to be necessary, the levels of the various antigens and adjuvants in the adjuvant-incorporated cells may also be calculated and used in determining proposed amounts for initial studies. Using MPL as an example, between about 0.4 ng and about 3.1 ng adjuvant may be incorporated per million cells; with levels of above about 1 ng per million being routinely achieved. A particular tumor-associated antigen, depending on the preponderance of expression, may vary widely, with between about 600 ng to about 1 $\mu$g per million cells believed to be common.

It is contemplated that an amount of adjuvant-incorporated cells between about $6 \times 10^4$ cells and about $1 \times 10^6$ cells per kg body weight of animal will prove useful for antibody or T cell generation. Preferably, amounts of between about $1 \times 10^5$ cells and about $5 \times 10^5$ cells per kg body weight will be used. As will be readily understood to those in the art, if a cell contains an amount of accessible antigen or adjuvant within the cell membrane that is towards the lower end of the contemplated useful range, one would choose to include more cells in the immunization composition. Conversely, if a cell contains higher amounts of accessible antigen or adjuvants, then less cells could be effectively used.

Optimizing the amount of the composition administered to an experimental animal to achieve the desired results is routine, as is known to those of skill in the art. The amount of the cellular-adjuvant composition used in the production of antibodies will naturally vary with the cell, antigen and adjuvant, as well as with the animal used for immunization. However, optimization simply involves sampling blood and assaying for the desired antibodies. It should also be noted that for antibody generation per se, toxicity is not generally a problem so long as certain of the animals used survive for a period of time sufficient to produce antibodies.

Although described in certain embodiments in terms of melanoma antigens, the present invention is, of course, suitable for use in enhancing the immune response to a wide variety of tumor cells and tumor antigens, in order to generate useful antibodies. There is practically no limit to the range of tumor cells and antigens that could be employed in this manner. Likewise, the range of adjuvants that can be used is also virtually limitless, so long as they can be incorporated into the membrane. Exemplary tumor cells, antigens and adjuvants were described in the earlier sections.

For antibody generation, the choice of agents for use in the immunizing composition is, of course, even less restricted than in clinical embodiments, as little emphasis is placed on the long term well-being of the immunized animal. The antibodies generated may be used in a variety of embodiments, some of the most evident of which are in the detection, purification or molecular cloning of the antigen. For example, where tumor cell antigens are concerned, antibodies may be used in the identification of antigen-positive cells within clinical samples, thereby allowing diagnosis of patients with cancer, as described below.

In somatic-cell hybridization, as described in Example 6, immunologists fuse normal B or T lymphocytes with tumor cells, obtaining a heterokaryon; after random loss of some chromosomes, a hybridoma is formed containing a single nucleus with chromosomes from each of the fused cells. Historically, cell fusion was promoted with Sendai virus, but now it is generally done with polyethylene glycol.

T-cell hybridomas can also be obtained by fusing T lymphocytes with cancerous T-cell lymphomas. Again, the resulting hybridoma continues to express the genes of the normal T cell but acquires the immortal-growth properties of the cancerous T lymphoma cell. Immunologists have generated a number of stable hybridoma cell lines representing T helper and T cytotoxic lineages. Such T cell hybridomas do not secrete antibody, but rather possess other immunological functions, such as secretion of cytokines and expression of T-cell receptors specific for a particular antigen-MHC molecule. As T-cell hybridomas grow as tumors, large cell numbers can be attained within a short period of time.

Primary lymphoid cell cultures can be obtained by isolating lymphocytes directly from blood or lymph or from various lymphoid organs by tissue dispersion. The lymphocytes can then be grown in a chemically defined basal medium (containing saline, sugars, amino acids, vitamins, trace elements, and other nutrients) to which various serum supplements are added, including interleukin 2 (IL-2), an essential component for the growth of T lymphocytes. Normal T lymphocytes may be cultured with adjuvant-incorporated cells in the presence or absence of IL-2, to produce clones of antigen-specific T lymphocytes. These individual clones may be propagated and studied in culture and even frozen for storage.

VI. Types and Uses of Antibodies and Cells

The usefulness of anti-ganglioside antibodies is evidenced in part through the extensive number of such antibodies described in the scientific literature. Many murine MAbs have been described, for example, anti-GD3 Mabs. Since GD3 is the major ganglioside of metastatic melanoma, a number of murine Mabs against GD3 have been generated. The first of its kind was produced by Pukel et al. (1982) and was designated as Mab:R-24 (R-24). A number of investigators have studied specificity of the R-24 antibody for GD3 (Dippold et al., 1985; Graus et al., 1984). This antibody belongs to the IgG3 subclass and has been used extensively to screen for the presence of GD3 in normal and biopsied human tissues (Dippold et al., 1985; Graus et al., 1984; Pukel et al., 1982).

Another similar MAb with almost identical specificity was developed by Yeh et al. (1982). In contrast to R-24, it is an IgM class antibody (Nudelman et al., 1982; Brodin et al., 1985). This antibody, designated Mab:4.2, reacts with GD3 but not with GM3, GM2, GD2a, GD1b, GT1a, GT1b, or GQ1b; it also reacts with a disialoparagloboside (Brodin et al., 1985). Three other IgG3 class antibodies are known, namely, Mabs:IFA, 2B2, and IC9 (Hellstrom et al., 1985). Recently, other investigators have developed two other Mabs reacting with GD3 (Cheresh et al., 1984, 1985).

In addition to anti-GD3 Mabs, murine Mabs against GD2 have been developed by two groups (Cheresh et al., 1984; Cheung et al., 1986). Cheung et al. (1986) have developed Mabs:3F8, 2F7, 3G6, and 3A7 and found all of them to react with purified GD2 but not with GM1, GD1a, GT1a, and GT1b. Cheresh et al. (1984) have produced two murine Mabs to GD2:126 (IgM) and Mab 14.18 (IgG).

O-acetyl GD3 in human melanoma has been identified using Mab D1.1, which was originally prepared against a rat brain tumor cell line and found to react with a ganglioside present in fetal rat brain (Cheresh et al., 1984). This ganglioside binds specifically to O-acetyl GD3 before but not after alkali treatment of the ganglioside. In contrast, Mab:R-24 recognizes the ganglioside after but not before alkali treatment. While it is clear that D1.1 recognizes 9-O-acetyl GD3, it is not clear whether the Mab can also recognize the O-acetyl sialic acids on glycoproteins. Thurin et al. (1985) produced a murine Mab 311 by immunizing with a human metastatic melanoma cell line (WM46). ME311 binding affinity was identical to that of D1.1 on TLC.

Natoli et al. (1987) purified a murine Mab 5.3 by immunizing mice with a murine melanoma cell line. The Mab reacted specifically to N-acetyl and N-glycolyl GM2, but not to GM3, GD3, GM1, or GD1a on TLC plates. Only GM2 significantly inhibited the antibody binding to a target cell (mouse melanoma JR-RH-16).

An example of stereospecificity of Mabs has been shown by Hirabayashi et al. (1986), who established a mouse Mab against a syngeneic melanoma B16 cell. This Mab reacted with chemically synthesized GM3, NeuAcα2-3GA1β1-4G1cβ1-1 ceramide (24:0/d18:1), but not with its stereoisomer, NeuAcβ2-3Ga1β1-4G1cβ1-1 ceramide (24:0/d18:1).

Human antibodies against gangliosides have also been produced. The principle involved in producing such MAbs is to obtained lymphocytes from patients with cancer or neuropathies, particularly from those showing autoantibodies against melanoma-associated gangliosides GD2 and GM2, from peripheral blood lymphocytes and to immortalize them in vitro using Epstein-Barr virus (Irie et al., 1982). This technique has produced two monospecific antibodies to antigens designated originally OFA-I-1 and OFA-I-2. OFA-I-2 binding to target cells was selectively inhibited by GD2 but not by GM3, GD3, GM2, GM1, GD1a, or GT1b (Cahan et al., 1982). Similarly, OFA-I-1 showed specificity for GM2 (Tai et al., 1983).

Further human MAbs against melanoma-associated gangliosides have been derived from lymph node lymphocytes (LNL) and peripheral blood lymphocytes (PBL) from melanoma patients (Yamaguchi et al., 1987). The Mabs reacting with the N-acetyl type of gangliosides were identified as Mab:HJM1; Mab:FCMI; Mab:32-27M; and Mab:2-39M. The techniques of the present invention can thus be adapted to prepare human antibodies in light of the above information and scientific references.

Several anti-ganglioside antibodies have been described in the U.S. patent literature, even further indicating their usefulness. For example, U.S. Pat. No. 5,270,202 concerns anti-idiotypic antibodies to human melanoma-associated antigens and their use diagnosis, disease monitoring and therapy. U.S. Pat. No. 5,141,864, incorporated herein by reference, concerns hybridomas and Mabs specific to gangliosides. This patent describes suitable methods for purifying gangliosides, methods for treating patients suffering from melanoma and methods for diagnosing sera.

U.S. Pat. No. 5,055,559 describes the antibody MG-21 that is directed against a tumor-associated glycolipid antigen. This antibody is capable of lysing tumor cells in vivo. U.S. Pat. No. 5,009,995 concerns Mabs that specifically bind to the gp130 glycoprotein cell surface antigen of human melanoma cells. U.S. Pat. No. 5,006,470 describes human Mab HJM1 that specifically binds to each of the ganglioside antigens GD2, GD3, GM3 and GD1b and human Mab FCM1 that binds to the ganglioside antigens GM3 and GD1a.

Further useful Mabs that bind to antigens associated with human melanomas are described in U.S. Pat. Nos. 5,134,075 and 5,126,262. U.S. Pat. No. 5,134,075 is incorporated herein by reference for the purposes of describing diagnostic methods, such as the detection of malignant cells associated with tumors, and therapeutic methods for treatment of humans with tumors. Other Mabs that bind ganglioside antigens are described in U.S. Pat. No. 4,849,509.

U.S. Pat. No. 5,104,652 describes useful Mabs directed against the disialoganglioside, GD3, that is expressed by certain fetal thymocytes, lymph node lymphocytes and a small subset of T cells in the peripheral blood. These Mabs stimulate proliferation of T cells, and can also be useful in treating melanoma in humans. Patents such as U.S. Pat. No. 5,104,652, incorporated herein by reference, describe the physiologically active amounts of antibodies that are required for effective treatment of melanoma in humans. This is another way in which the effective therapeutic amounts of the adjuvant-incorporated cell compositions of the present invention may be defined, i.e., as amounts effective to produce an amount of antibody described to be active against melanoma in U.S. Pat. No. 5,104,652.

Even the adjuvant-laden cells of the present invention have other uses themselves. For example, they may be employed to enrich a population of cells for T suppressor cells, as generally disclosed by Baker et al. (1990). These authors showed that MPL binds T suppressor cells, and that dishes coated with MPL can be used to purify $T_S$ cells. The studies by Baker et al. (1990) describe the binding and elution of spleen cells from plastic dishes coated with MPL that resulted in a >1,000-fold enrichment of antigen-specific suppressor T-cell ($T_S$) activity. Therefore, cells conjugated to MPL could also be used in this useful protocol.

VII. Diagnostic and Prognostic Uses of Antibodies

Anti-ganglioside antibodies prepared using the methods and compositions of the present invention may be employed in a variety of diagnostic and prognostic embodiments. The rationale behind these uses can be found in several earlier findings. For example, in examining the ganglioside patterns found in various melanoma tumor biopsies and cell lines, both diversity and uniformity have been observed (Ravindranath et al., 1989).

The diversity is pertaining the five major gangliosides, namely, $GM_3$, $GM_2$, $GD_3$, $GD_2$ and O-acetyl $GD_3$. The parent ganglioside appears to be $GM_3$; $GM_2$ and $GD_3$ arise directly from this ganglioside; and other gangliosides are the products of $GD_3$. It is believed that an enzyme cascade is involved in ganglioside biosynthesis and that genes responsible for these enzymes may be governing their diversity (Ravindranath et al., 1989). The diversity supports the proposal that all anti-ganglioside antibodies will be useful. Tumors found in some patients express more than 90% of $GD_3$. The uniformity in the preponderance of $GD_3$ in all tumors indicates that therapy targeting $GD_3$ is likely to be an effective treatment for human melanoma.

Melanoma-associated gangliosides have substantial clinical relevance in view of the property of shedding from tumor cells into the circulation. Observations made on the sera of neuroblastoma patients reveal that there is a significant correlation between tumor-associated ganglioside (GD2) level and clinical stages of the disease, indicating that tumor burden could be a factor involved in shedding of tumor-associated gangliosides (Ladisch et al., 1987). It is also believed that the level of circulating gangliosides correlates with the clinical stages of melanoma (Portoukalian, 1978), and that the serum levels of melanoma-associated gangliosides will be an effective diagnostic indicator of the different stages of melanoma.

Indeed, Ravindranath et al. (1991) evaluated the relevance of the ratio of melanoma associated ganglioside $GD_3$, and its precursor, $GM_3$ in predicting the probable survival and in designing therapeutic modalities. In examining tumor biopsy specimens from 42 patients for ganglioside pattern, it was found that $GM_3$ and $GD_3$ constitute 80% of the total gangliosides. The ratio of $GM_3:GD_3$ in normal melanocytes was 19:1, and in tumor specimens, it ranged from 15:1 to 1:5.

Ravindranath et al. (1991) categorized the patients into three groups based on their ganglioside ratio. Group I ratio ranged from 15:1 to 1.5:1 (10 patients); Group II ratio ranged from 1.4:1 to 1:1.4 (13 patients); Group III ratio ranged from 1:1.5 to 1:5 (19 patients). When the overall survival of patients from the onset of the stage II disease was evaluated among different groups, Group I patients survived significantly longer than other patient groups. A routine analysis of the ganglioside ratio of tumor excised after surgery is thus believed to be useful, particularly as melanoma expresses a simple pattern of gangliosides unlike other forms of cancer.

Melanoma-associated gangliosides have also been found in other malignant human tissues. This heightens the usefulness of both the diagnostic embodiments of the invention, and the aspects of the invention that concern generating an effective immune response against ganglioside antigens. The distribution of melanoma-associated gangliosides in malignant human tissues is detailed in Table 4.

TABLE 4

Melanoma Associated Gangliosides in Malignant Human Tissues

| Gangliosides[a] | Distribution in Malignant Tissues | Reference |
| --- | --- | --- |
| GM3-NeuAc | melanoma | Carubia et al., 1984 |
|  | glioblastoma | Liepkalns et al., 1981 |
|  | meningioma | Berra et al., 1983 |
|  | astrocytoma | Berra et al., 1985 |
|  | neurofibrosarcoma | Tsuchida et al., 1984 |
|  | leukemia | Westrick et al., 1983a, 1983b; Kyogashima et al., 1987 |
|  | thyroid cancer | Bouchon et al., 1985 |
| GM3 - NeuGl | melanoma | Hirabayashi et al., 1987 |

TABLE 4-continued

Melanoma Associated Gangliosides in Malignant Human Tissues

| Gangliosides[a] | Distribution in Malignant Tissues | Reference |
|---|---|---|
| GM2 - NeuAc | melanoma | Carubia et al., 1984 |
|  | astrocytoma | Berra et al., 1985 |
|  | glioblastoma | Fredman et al., 1986 |
|  | CLL | Siddiqui et al., 1984 |
|  | Lung carcinoma | Miyake et al,, 1988 |
| GM2 - NeuGl | melanoma | Hirabayashi et al., 1987 |
| GD3 - NeuAc | melanoma | Pukel et al., 1982 |
|  | glioblastoma | Fredman et al., 1986 |
|  | astrocytoma | Berra et al., 1985 |
|  | meningioma | Berra et al., 1983 |
|  | neurofibrosarcoma | Tsuchida et al., 1984 |
|  | leukemia | Goff et al., 1983 |
|  | thyroid cancer | Bouchon et al., 1985 |
| GD3 - NeuGl | melanoma | Hirabayashi et al., 1987 |
| GD3 - O-AcNeuAc | melanoma | Cheresh et al., 1984; Thurin et al., 1985; Ravindranath et al., 1988 |
| GD2 - NeuAc | melanoma | Carubia et al., 1984 |
|  | neuroblastoma | Irie et al., 1982; Cahan et al., 1982 |
|  | glioma | Liepkalns et al., 1981 |
|  | astrocytoma | Berra et al., 1985 |

GM3 - NeuAc: NeuAcα2-3Galβ1-4Glcβ1-1Ceramide
GM3 - NeuGl: NeuGlα2-3Galβ1-4Glcβ1-1Ceramide
GM2 - NeuAc: NeuAcα2-3(GalNAcβ1-4)Galβ1-4Glcβ1-1Ceramide
GM2 - NeuGl: NeuGlα2-3(GalNAcβ1-4)Galβ1-4Glcβ1-1Ceramide
GD3 - NeuAc: NeuAcα2-8NeuAcα2-3Galβ1-4Glcβ1-1Ceramide
GD3 - NeuGl: NeuGlα2-8NeuAcα2-3Galβ1-4Glcβ1-1Ceramide
NeuAcα2-8NeuGlα2-3Galβ1-4Glcβ1-1Ceramide
GD3 - O-AcNeuAc: O-AcNeuAcα2-8NeuAcα2-3Galcβ1-4Glcβ1-1Ceramide
GD2 - NeuAc: NeuAcα2-8NeuAcα2-3(GalNAcβ1-4)Galβ1-4Glcβ1-1Ceramide Antibodies prepared using the invention may thus be used in various diagnostic and prognostic embodiments, in an analogous manner to those in the prior art, for example, in the immunodetection methods and associated kits described in U.S. Pat. No. 4,851,510. U.S. Pat. No. 4,851,510 describes an antibody that reacts with melanoma-associated tumors cells and methods for utilizing the antibody in diagnostic procedures, for determining the identity and extent of melanoma associated disease, and other immunological procedures. Anti-tumor antibodies generated using this invention may be employed as described in U.S. Pat. No. 4,851,510, and in medical diagnosis-immunoassays, as described in U.S. Pat. No. 4,808,704. As mentioned above, U.S. Pat. Nos. 5,141,864 and 5,134,075 also teach the use of antibodies in diagnostic methods.

If desired, the antibodies may be linked to a detectable label, such as a radioactive, fluorogenic or a nuclear magnetic spin resonance label. Biolabels, such as biotin, and enzymes that are capable of generating a colored product upon contact with a chromogenic substrate are most preferred. Exemplary enzyme labels include alkaline phosphatase, hydrogen peroxidase and glucose oxidase enzymes.

Fawwaz et al. (1990), describe radiopharmaceutical compositions consisting of Mabs to human melanoma-associated antigens that are labeled with palladium-109. These chelated antibodies demonstrate high uptake in melanoma and are used for tumor therapy. U.S. Pat. No. 4,562,160 also describes antibodies tagged with chromophoric and radioactive labels of diagnostic value for use in immunoassays for melanoma.

Antibodies obtained using the invention, and kits thereof, may thus be used in the immunodetection of compounds in clinical samples, and could also be used in antigen titering, purification, molecular cloning and the like. In general, immunodetection methods using anti-tumor antibodies, such as anti-ganglioside antibodies, will include first obtaining a sample suspected of containing a tumor-antigen, such as a biological sample from a patient, and contacting the sample with a first antibody that binds to a the antigen under conditions effective to allow the formation of an immunocomplex (primary immune complex). One then detects the presence of any primary immunocomplexes that are formed.

Contacting the chosen sample with the antibody under conditions effective to allow the formation of (primary) immune complexes is generally a matter of simply adding the antibody composition to the sample. One then incubates the mixture for a period of time sufficient to allow the added antibodies to form immune complexes with, i.e., to bind to, any antigens present within the sample. After this time, the sample composition, such as a tissue section, ELISA plate, dot blot or western blot, will generally be washed to remove any non-specifically bound antibody species, allowing only those specifically bound species within the immune complexes to be detected.

The detection of immunocomplex formation is well known in the art and may be achieved through the application of numerous approaches known to the skilled artisan and described in various publications. Detection of primary immune complexes is generally based upon the detection of a label or marker, such as a radioactive, fluorigenic, biological or enzymatic label, with enzyme tags such as alkaline phosphatase, horseradish peroxidase and glucose oxidase being suitable. The antibody employed may itself be linked to a detectable label, wherein one would then simply detect this label, thereby allowing the amount of bound antigen present in the composition to be determined.

In one alternative, the primary immune complexes may be detected by means of a second binding ligand that is linked to a detectable label and that has binding affinity for the first antibody. The second binding ligand is itself often an antibody, which may thus be termed a "secondary" antibody. The primary immune complexes are contacted with the labeled, secondary binding ligand, or antibody, under conditions effective and for a period of time sufficient to allow the formation of secondary immune complexes. The secondary immune complexes are then generally washed to remove any non-specifically bound labelled secondary antibodies or ligands, and the remaining bound label is then detected.

In yet another alternative, the secondary immune complexes may be detected by means of a tertiary binding ligand that is linked to a detectable label and that has binding affinity for the second binding ligand or antibody. The tertiary binding ligand will again often be an antibody, which may thus be termed a "tertiary" antibody. The secondary immune complexes are contacted with the labeled, tertiary binding ligand, or antibody, under conditions effective and for a period of time sufficient to allow the formation of tertiary immune complexes. The tertiary immune complexes are then generally washed to remove any non-specifically bound labelled antibodies or ligands, and the remaining bound label is then detected.

This latter alternative is exemplified by the sandwich ELISA. Here, antibodies may first be immobilized and then contacted with a sample suspected of containing, e.g., a tumor antigen, the secondary antibody may be an unlabeled anti-tumor polyclonal or Mab, and the tertiary antibody will often be a commercially available labeled antibody that is specific for a non-variant portion of the second antibody.

With regard to ELISAs to detect ganglioside antigens, the inventors particularly contemplate that the methods described in Ravindranath et al. (1994c, incorporated herein by reference) should be employed. This paper describes the factors affecting the fine specificity and sensitivity of serum anti-ganglioside antibodies in ELISAs. A protocol is presented that minimizes the factors associated with creating the high background values often observed in such assays.

Most of the immunodetection methods may be adapted for use in immunohistochemical detection in which antibodies are used in conjunction with both fresh-frozen and formalin-fixed, paraffin-embedded tissue blocks. For diagnostic purposes, it is proposed that virtually any sample suspected of containing the relevant antigen, e.g., a tumor antigen, sought to be detected may be employed. Exemplary samples include all biopsy samples, which could be analyzed directly using immunohistochemistry, or after homogenization to detect the antigen in standard ELISA or blotting methods. Other clinical samples obtained from patients, such as blood, serum, urine, saliva, and the like may also be used according to the location of the antigen-bearing cells to be detected.

As mentioned, antibodies raised using the present invention may be formulated into kits that may be employed to detect the presence of tumor-associated antigens in a sample. Immunodetection reagents are included in the kits, and may be in the form of a label associated with the antibody, or associated with a secondary binding ligand. Exemplary ligands might include a secondary antibody directed against the first antibody, or a biotin or avidin (or streptavidin) ligand having an associated label. The kits may contain antibody-label conjugates either in fully conjugated form, in the form of intermediates, or as separate moieties to be conjugated by the user of the kit.

The container means in the kits will generally include at least one vial, test tube, flask, bottle, syringe or other container means, into which the antibody may be placed, and preferably suitably allocated. Where a second binding ligand is provided, the kit will also generally contain a second vial or other container into which this ligand or antibody may be placed. The kits of the present invention will also typically include a means for containing the vials in close confinement for commercial sale, such as, e.g., injection or blow-molded plastic containers into which the desired vials are retained.

VIII. Modes of Administration

Gangliosides of melanoma may have a major role in tumor spreading and metastasis. Gangliosides GD3 and GD2 enable spreading of the tumor cells by binding to various adhesion molecules and promote infiltration through the basement membrane barrier resulting in tissue metastasis (Cheresh et al., 1986; Cheresh & Klier, 1986). Monoclonal antibodies directed specifically to the carbohydrate moiety of GD3 and GD2 are believed to inhibit melanoma cell attachment to various basement membrane constituents.

Although the invention is clearly very useful as a general immunological tool, e.g., in antibody and T cell production, as described above, the results presented herein also have significant relevance to immunotherapy of human diseases and disorders, including cancer. In human therapeutics it is important that the adjuvant-incorporated cells of the invention be formulated in a pharmacologically acceptable vehicle. Many such formulations are known, as described herein. In optimizing an adjuvant-incorporated cell for later use in humans, it is important that pre-clinical studies also be conducted in pharmacologically acceptable solutions, such as, by way of example only, RPMI 1640. Other suitable pharmacologically-acceptable media are described, e.g., in Sigma Cell Culture, 1993 (incorporated herein by reference).

In using the adjuvant-incorporated cells of the present invention in treatment methods, other standard treatments may also be employed, such as radiotherapy or chemotherapy. However, it is preferred that the immunotherapy be used alone initially as it effectiveness can be readily assessed. Immunotherapies of cancer can broadly be classified as adoptive, passive and active specific, as described in the following sections.

The present invention is particularly suitable for use with other immunotherapeutic protocols. For example, pretreatment with BCG is currently contemplated. Bast et al. (1974) reviewed the use of BCG in cancer treatment, giving substantial directions as to its various modes of uses. Lamm et. al. (1991) described the use of BCG in superficial bladder cancer. Minden et al. (1976) and Yamamoto et al. (1988) also reported on the mechanisms of action of BCG. Bennet et al. (1988) provided further evidence that pre-treatment with BCG is useful in the specific context of MPL.

A. Adoptive Immunotherapy

In adoptive immunotherapy, the patient's circulating lymphocytes, or tumor infiltrated lymphocytes, are isolated in vitro, activated by lymphokines such as IL-2 or transduced with genes for tumor necrosis, and readministered (Rosenberg et al., 1988; 1989). This form of immunotherapy has produced several cases of regression of melanoma and renal carcinoma, but the percentage of responders were few compared to those who did not respond.

It is proposed that the failure of adoptive immunotherapy may be due to interaction of the activated cells with excess circulating tumor antigens, such as gangliosides, shed from tumor tissues. The present invention is ideally suited to overcome this problem. To achieve this, one would administer to an animal, or human patient, an immunologically effective amount of activated lymphocytes in combination with an adjuvant-incorporated cell composition as described herein. The activated lymphocytes will most preferably be the patient's own cells that were earlier isolated and from a blood or tumor sample and activated (or "expanded") in vitro.

In terms of the doses, it is contemplated that about 24 million adjuvant-incorporated cells would be injected intradermally, possibly followed by one to two further injections of 24 million adjuvant-incorporated cells. Currently, using MPL as an example, 24 million MPL-incorporated melanoma cells would contain, as a minimum, about 25 ng of MPL; on average, about 50 ng of MPL; and up to about 75 ng or so of MPL. This would be followed by the standard administration of IL-2 activated killer cells.

B. Passive Immunotherapy

A number of different approaches for passive immunotherapy of cancer exist. They may be broadly categorized into the following: injection of antibodies alone; injection of antibodies coupled to toxins or chemotherapeutic agents; injection of antibodies coupled to radioactive isotopes; injection of anti-idiotype antibodies; and finally, purging of tumor cells in bone marrow.

In passive immunotherapy, patients are administered monospecific or polyspecific Mabs. In the case of melanoma, the antibodies used are often anti-ganglioside Mabs. Several anti-ganglioside antibodies (R24, 3F8 and Mab 36.1) have been tested in clinical trials (Vadhan-Raj et al., 1988), but complete regression was rare. It is not clear that the antibody always reached its tumor target.

Preferably, human monoclonal antibodies, are employed in passive immunotherapy, as they produce few or no side effects in the patient. However, their application is somewhat limited by their scarcity and have so far only been administered intralesionally. Human monoclonal antibodies to ganglioside antigens have been administered intralesionally to patients suffering from cutaneous recurrent melanoma (Irie & Morton, 1986). Regression was observed in six out of ten patients, following, daily or weekly, intralesional injections. In another study, moderate success was achieved from intralesional injections of two human monoclonal antibodies (Irie et al., 1989).

Certain limitations of passive immunotherapy are likely due to the interaction of administered antibodies with the tumor-derived antigens, again exemplified by gangliosides, shed into the blood. The present invention could be used prior to passive immunotherapy to achieve advantageous results. One would again administer to the animal or patient an immunologically effective amount of the adjuvant-incorporated cell composition, followed later by an immunologically effective amount of the polyclonal or monoclonal antibodies.

U.S. Pat. No. 5,091,178 describes a method for treating human melanoma that includes administering a MG-21-like (HB-9011-like) Mab to a patient in a dose effective to kill melanoma cells. U.S. Pat. No. 5,091,178 is incorporated herein by reference for the purpose of describing methods of passive immunotherapy that may be combined with the present invention. It is also used for the purpose of assisting in the identification effective therapeutic amounts of the adjuvant-incorporated cell compositions described herein. Thus, an amount of an adjuvant-incorporated cell composition that is effective to produce an amount of antibody equivalent to the amounts described in U.S. Pat. No. 5,091,178 will likely be a therapeutically effective amount.

Systemic injection of unconjugated anti-ganglioside monoclonal antibodies was first carried out using an $IgG_3$ class murine monoclonal antibody, R24, in patients suffering from metastatic melanoma (Dippold et al., 1980; 1984; 1985; Houghten et al., 1985; Vadhan-Raj et al., 1988). An effective treatment protocol was developed, which is also contemplated for use in passive immunotherapy in conjunction with the present invention. A phase 1 clinical trial of IL-2 and escalating doses of R24 has also been performed (Bajorin et al., 1988).

The initial R24 treatment protocol includes systemic injection of ganglioside monoclonal antibodies at three dose levels (8, 80, or 240 $mg/m^2$) administered over a period of two weeks (Houghten et al., 1985). Patients are given antibodies in 100 to 200 $\mu$l of 0.9% saline/5% human serum albumin. The effectiveness of the treatment protocol is dose dependent, however, so is the toxicity to the patient. Doses and treatment schedule may be varied in order to optimize immunotherapy.

It may be favorable to administer more than one monoclonal antibody directed against two different gangliosides or even antibodies with multiple ganglioside specificity. Treatment protocols may also include administration of lymphokines or other immune enhancers as in Bajorin et al. (1988).

It is contemplated that doses of about 24 million adjuvant-incorporated cells would be administered, containing about 25 ng to about 75 ng of MPL, with an average of about 50 ng of MPL.

C. Active Immunotherapy

In active immunotherapy, an autologous or allogeneic tumor cell composition or "vaccine" is administered, generally with a distinct bacterial adjuvant (Ravindranath & Morton, 1991; Morton & Ravindranath, 1993; Morton et al., 1992; Mitchell et al., 1990). In melanoma immunotherapy, those patients who elicit high IgM response often survive better than those who elicit no or low IgM antibodies (Morton et al., 1992). IgM antibodies are often transient antibodies and the exception to the rule appears to be anti-ganglioside or anticarbohydrate antibodies.

The use of adjuvant-incorporated tumor cell vaccines would be a valuable addition to active immunotherapy. Here, one could simply replace the irradiated tumor cells with an adjuvant-incorporated irradiated cell composition in accordance with the invention. Alternatively, one may still use the original irradiated tumor cell composition or "vaccine" and mix this with the same, or a related type, of irradiated tumor cells into which an adjuvant has been incorporated. Generally, the adjuvant-incorporated cells would be prepared first and then irradiated, although irradiation prior to or at any point of the preparative process is also possible.

Methods for treatment of melanoma with vaccines that include irradiated autologous melanoma tumor cells are well known, as exemplified by U.S. Pat. No. 5,290,551, incorporated herein by reference. This patent concerns a haptenized tumor vaccine for the treatment of cancer where the cells are attached to dinitrophenyl, trinitrophenyl or N-iodoacetyl-N'-5 sulfonic 1-naphtyl ethylene diamine. Although the adjuvant-incorporated cell compositions of this invention are distinct from the compositions of the U.S. Pat. No. 5,290,551 patent, the method described in U.S. Pat. No. 5,290,551 could be employed in this invention.

An active specific immunotherapy protocol, developed by one of the present inventors (Morton et al., 1992), involves immunization of melanoma patients with a polyvalent, irradiated melanoma cell vaccine (MCV). The patients are stratified by stage and disease status and given, in a random manner, either MCV alone or MCV plus one of the biologic response modifiers (BRM), which have been shown to downregulate suppressor cell activity. These BRMs include Cimetidine (CIM; 1200 mg/d) (Smith/Kline, Pa.); Indomethacin (IND; 150 mg/d) (Lederle, N.J.); or low-dose Cyclophosphamide (CYP; 75, 150 or 300 $mg/m^2$) (Johnson/Mead, N.J.).

MCV is produced in large batches and analyzed for MAA antigen expression to determine variance between lots. The MCV is screened for viral (HIV, hepatitis), bacterial and fungal infectious organisms. Equal amounts of each line are pooled to a total of 24×10$^6$ cells in serum-free medium containing 10% dimethyl sulfoxide and cryopreserved in liquid nitrogen. Before cryopreservation, the cells are irradiated to 100 GY.

Prior to treatment, MCV is thawed and washed 3 times in phosphate buffered saline. MCV is injected intradermally in axillary and inguinal regions on a schedule of every 2 weeks for six weeks, then monthly for a year. For the first two treatments, MCV is mixed with BCG (Glaxo, England) (24×10$^6$ organisms/vial). After one year, the immunization interval is increased to every 3 months for one year, then every 6 months. Follow-up clinical and laboratory evaluations are repeated monthly, with chest x-rays every 3 months.

In using adjuvant-incorporated melanoma cell vaccines, as exemplified by MPL-MCV, one would again generally use about 24 million adjuvant-incorporated cells in the immunotherapy protocol described by Morton et al. (1992). These cells would contain upwards of about 25 ng of MPL, and generally between about 50 ng and about 75 ng of MPL. Although the amounts of MPL are not large, as the "parent" MCV has already been shown to give beneficial results in patients, it is contemplated that the MCV cells supplemented with virtually any amount of MPL in the membrane would give enhanced results. Where pre-treatment with BCG is used (Bast et al., 1974; Bennet et al., 1988) it is contemplated that a ¾ reduced dose may be employed, i.e., about 18 million cells.

Vosika et al. (1984) have shown that levels of MPL up to about 100 $\mu$g/m$^2$ (about 173 $\mu$g for the average adult) are safe for human administration. Therefore, the 50–75 ng of MPL currently proposed could also be increased considerably, either be using more cells or, preferably, by increasing the amount of MPL per cell, and still maintain the MPL dose clearly within the safety limits.

Using adjuvant-incorporated melanoma cell vaccines alone, as exemplified by MPL-MCV, one may be able to administer less cells than previously employed. This is based upon the following line of reasoning: tumors shed tumor-associated antigens into the general circulation; these antigens may be immunogenic or non-immunogenic, and may even be immunosuppressive; the shed immunosuppressive tumor antigens may cause angry and immune exhaustion. One aspect of the present invention is to eliminate the immunosuppressive antigens and to restore immunocompetence. Coupled with the fact that the adjuvant-incorporated cells of the invention are highly effective due to the unique presentation of antigens and adjuvants together, this means that lower numbers of cells may prove to be effective in treatment methods.

IX. Pharmacological and Vaccine Formulations

Aqueous compositions of the present invention comprise an effective amount of the adjuvant-incorporated cells or vaccines dissolved or dispersed in a pharmaceutically acceptable carrier or aqueous medium. The phrases "pharmaceutically or pharmacologically acceptable" refer to molecular entities and compositions that do not produce an adverse, allergic or other untoward reaction when administered to an animal, or a human, as appropriate.

Just one example of a currently preferred pharmaceutical vehicle is RPMI 1640, which is highly suitable for use in humans. Sigma Cell Culture, (1993) describes many other suitable pharmacologically-acceptable media.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

The active compounds will generally be formulated for parenteral administration, e.g., formulated for injection via the intravenous, intramuscular, sub-cutaneous, intralesional, or even intraperitoneal routes. The preparation of an aqueous composition that contains adjuvant-incorporated cells as active components will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

Solutions of the active compounds can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

Adjuvant-incorporated cell conjugates can be formulated into a composition in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi.

The carrier can also be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly, concentrated solutions for intramuscular injection is also possible. In this regard, the use of DMSO as solvent is preferred as this will result in extremely rapid penetration, delivering high concentrations of the cells to a small area.

Upon formulation, solutions will be administered in a manner compatible with the dosage formulation and in such amount as is therapeutically effective. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intralesional and intraperitoneal administration. In this connection, sterile aqueous media which can be employed will be known to those of skill in the art in light of the present disclosure and texts such as "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject.

In addition to the compounds formulated for parenteral administration, other pharmaceutically acceptable forms include, e.g., tablets or other solids for oral administration; time release capsules; and virtually any other form currently used. Therapeutic formulations of the invention may also be prepared in forms suitable for topical administration, such as in cremes and lotions.

EXAMPLE 1

ATTACHMENT OF MONOPHOSPHORYL LIPID A (MPL) AND PRECURSORS TO CELLS AND LIPOSOMES

I. Materials and Methods

A. Adjuvants

Lipid A and MPL purified from *S. Minnesota* R595 were purchased from Ribi Immunochem Research (Hamilton, Montana). LPS from *S. Minnesota* Re595 was purchased from Calbiochem (San Diego, Calif.). For immunization, these adjuvants were administered as aqueous suspensions in saline or Hank's balanced salt solution (HBSS). For human use, a pharmacologically-acceptable medium should be used, such as RMPI 1640.

B. Cells

Murine B-16 melanoma cells syngeneic to C57BL\6J mice and a human melanoma cell line, M25, were used as a xenogeneic model. The M25 cell line is derived from a metastatic melanoma tumor specimen. The ganglioside profiles of both the cell lines were characterized earlier (Ravindranath et al., 1988; Hirabayashi et al., 1985). Both M25 and B16 cells were cultured in the laboratory in a RPMI 1640 medium containing 2 mM of glutamine supplemented with 5% fetal bovine serum. An antibiotic-antimycotic mixture (penicillin, 10,000 units/ml; fungizone, 25 $\mu$g/ml; streptomycin, 10,000 $\mu$g/ml) was added to the medium. Cell viability was assessed using the trypan-blue dye exclusion procedure. After five or six passages, B16 cells were irradiated for 13 or 15 min at 7000 R at UCLA's gamma cell counter facility. Only irradiated B16 cells were used for incorporating MPL and for immunization studies.

C. Gangliosides and Phospholipids $GM_3$ and $GM_2$, purified from bovine brain, were obtained from Sigma (St. Louis, Mo.). Gangliosides were also purified from tumor biopsies or from cultured melanoma cells (M25) as described earlier (Ravindranath et al., 1988). The total lipid bound sialic acid (LBSA) in M25 is 78 $\mu$g/g wet weight (approximately $1\times10^7$ cells). Individual gangliosides were isolated with Iatrobead columns (50 cm$\times$1.6 cm) (Iatron Lab Inc, Tokyo, Japan) using a step gradient of a two-solvent system: chloroform:methanol:water (v/v) (A: 80:20:2 and B: 50:40:3). $GD_3$ and its derivatives were isolated from thin layer chromatographic (TLC) plates (Ravindranath et al., 1988; Hirabayashi et al., 1985). The chromatographic purity of the individual gangliosides was assessed by TLC before coating the ELISA plates. All gangliosides used in this study contained N-acetyl neuraminic acid as assessed by chromatographic mobility in different solvent systems and after base treatment. The phospholipids were purchased from Sigma: phosphatidyl choline (PC:XIIIE from egg yolk), phosphatidyl ethanolamine (PE) and phosphatidyl serine (PS)(from bovine brain).

II. Results

A. Conjugation of LPS, Lipid A and MPL to Cells

Washed and packed tumor cells ($1\times10^6$ cells) were suspended in 1 ml of sterile phosphate-saline buffer, pH 7.2, containing 50 $\mu$g of LPS or lipid A or MPL. With cells intended for subsequent human administration, PBS would not be used and an acceptable buffer, such as sterile RPMI 1640, would be used. The mixture was incubated at 24° C. for 45–60 minutes with occasional agitation. The supernatant was removed after centrifugation. Sedimented cells were then washed in 9 volumes of cold sterile saline and stored on ice until use.

The tumor cells were also grown in culture in the presence of MPL to assess whether MPL can function as a tumor-growth inhibitor. MPL neither promoted nor inhibited the growth of M25 cells in vitro.

The conjugation of LPS and its derivatives to the cell membrane was assessed by a dye-exclusion assay using polymyxin B (an antibiotic that binds to LPS and its lipid A derivatives) (Carr & Morrison, 1984; Shafer & Spitznagel, 1984). The binding of polymyxin B to membrane-attached lipid A or MPL creates porosity of the membrane, which permits the dye to penetrate the cell. Twenty-five $\mu$l of M25 cells ($1\times10^6$ cells/ml) were added to 250 ul of LPS or lipid A or MPL (50 $\mu$g/ml), shaken gently and incubated for different time intervals (sec). Two hundred and fifty ul of polymyxin B (50 $\mu$g/ml) was added and incubated for 5 min. Next, 25 $\mu$l of 0.1% of trypan blue was added, and the viability of cells measured at 24° C. Dye exclusion was studied on cells treated with LPS/lipid A/MPL, polymyxin B, or LPS/lipid A/MPL plus polymyxin B for 15 min. Since maximum binding (50% of the total cells) occurred at 30 min, the incubation time was restricted to 45 min. The attachment of lipid A or MPL micelles with cells was also examined under microscope.

A new assay using the 8NAb 8A1 was developed for quantifying MPL bound on the cell surface. This procedure is described herein in Example 5.

To determine whether significant amount of MPL is left in the supernatant after attaching MPL to tumor cells, the MPL-containing supernatant from the initial batch of tumor cells was added to a fresh batch of $1\times10^6$ packed B16 or M25 cells. After incubation at 24° C. for 1 hr, the cells were tested for attachment of adjuvant using the polymyxin B exclusion assay. The adjuvant attached to only 3 to 5% of cells (for both B16 and M25). This indicates that more than 90% of the adjuvant was attached into the initial batch of tumor cells.

B. Preparation of Small Unit Vesicles (liposomes)

Small unit vesicles, with or without phospholipid (phosphatidyl choline [PC] (type III-B from bovine brain)/ phosphatidyl serine [PS] (from bovine brain), were prepared following the procedure described by Wilschut (1982) and Portoukalian et al. (1991). In brief, the gangliosides, MPL and PC or PS were dissolved in equimolar ratio (vide infra) in chloroform:methanol (1:1, v/v) and evaporated to dryness in small round-bottom flasks over a rotary evaporator. The lipid layer formed in the bottom of the flask was recovered as liposomes by adding 0.5 or 1 ml of warm sterile saline (40° C.) and by intermittent vortexing and sonication for 30 min. The liposomes were not of uniform size but remained stable for more than one hour on ice. The liposomes were administered within one hour after preparation.

EXAMPLE 2

IMMUNIZATION RESPONSE IN HUMAN MELANOMA CELL LINE M25

I. Materials and Methods

All adjuvants, cells, gangliosides, phospholipids and methods were as described in Example 1.

A. Mice

Strain BALB/c female mice, 4 to 5 weeks old (used in Example 2), and strain C57BL/6J male mice, 7 to 8 weeks old (used in Example 3 and Example 4), were obtained from Harlan Sprague Dawley Company (Indianapolis, Ind.) and maintained on mouse chow and water ad libitum in the animal house facility at University of California, Los Angeles (UCLA). Mice were divided into treatment groups of three.

B. ELISA

For determining anti-ganglioside, antiphospholipid and anti-MPL antibody levels (IgM and IgG), ELISA was performed following the protocol described earlier (Freudenberg et al., 1989). Phospholipids were dissolved in chloroform:ethanol (1:9, v/v), and gangliosides and MPL were suspended in ethanol (Freudenberg et al., 1989). In this study, Immunolon #1 microtiter plates were used, which were coated with 1 µg/100 µl of glycolipids in ethanol. Wells without antigen were used to assess the background noise. The mean absorbency was calculated for duplicate serum specimens and were corrected for the background value. The sera from saline (sterile) treated mice were used as a control, and the experimental mean values were corrected against control values. No preimmune sera were collected from experimental mice in order to avoid possible effects of injury.

C. Statistical Analyses

The significance of differences among group means was assessed using Mann-Whitney non-parametric tests of significance. The significance of the values obtained from a particular group is indicated in the Brief Description of the Drawings. Striking differences observed between groups were not subjected to statistical treatments.

D. Immunization Schedule

All immunizations were done intraperitoneally following pretreatment with saline. Antibody levels were measured in serum specimens collected 15 days after the first or second immunization. Each treatment group contained three mice and all treatments within each studies were conducted simultaneously.

Sham controls [saline treated mice (n=3)] were used for each study.

In the first study, three 4–5 week old female BALB/c mice were immunized with M25 cells alone or coated with LPS, lipid A or MPL (as described in Example 1). The first immunization was done on day 16 using $1 \times 10^5$ viable cells (about 780 nanogram of LBSA [gangliosides]) and the first bleeding was done on day 32. The second immunization was carried out on day 35, using $5 \times 10^5$ viable cells (about 3.9 microgram of LBSA [gangliosides]) and the second bleeding was done on day 48.

In the second study, three 4–5 week old female BALB/c mice were immunized on days 14 (first immunization) and 28 (second immunization) with micelles of MPL (4 µg for each immunization), $GM_3$ (2 and then 4 µg), $GD_3$ (2 and then 4 µg), $GM_3$-MPL (2+2 µg and then 4+2 µg), or $GD_3$-MPL (2+2 µg, and then 4+2 µg).

II. Results

A. Anti-ganglioside IgM Antibody Levels in Normal Mice

Using ELISA, low levels of IgM but not IgG antibodies were identified reacting to $GM_3$, $GD_3$, and $GM_2$ in the sera of normal, healthy mice (BALB/c and C57BL/6J) [sham controls]. The ELISA absorbency of anti-ganglioside IgM antibodies in both strains ranged from 0.090 to 0.135 at a dilution of 1:1000, suggesting that the anti-ganglioside antibodies are naturally occurring autoantibodies.

B. Antibody Response Against MPL Alone

The anti-MPL antibody responses in two groups of mice, one treated with MPL on day 0 and the other treated with saline on day 0, were compared. The anti-MPL IgM antibody responses after two immunizations were screened. In all these studies, the dose of MPL administered at one time never exceeded 10 µg/mouse. The results from both groups of mice showed that MPL alone administered two or three times elicited a poor antibody response, suggesting that MPL may not be immunogenic per se, similar to the gangliosides.

Figure 2A:
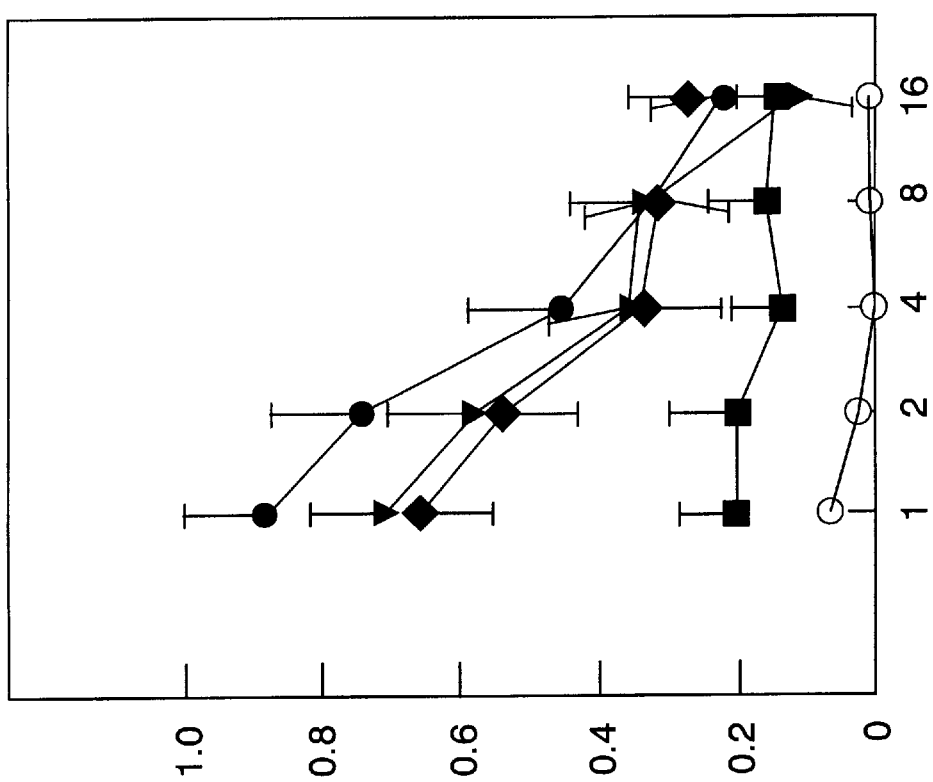
FIG. 2A, FIG. 2B and FIG. 2C. Mean (±SD) ELISA absorbency of anti-phospholipid IgG antibodies after second immunization of M25 human melanoma cells in BALB/c mice (FIG. 1, Example 2, first study).
Figure 2B:
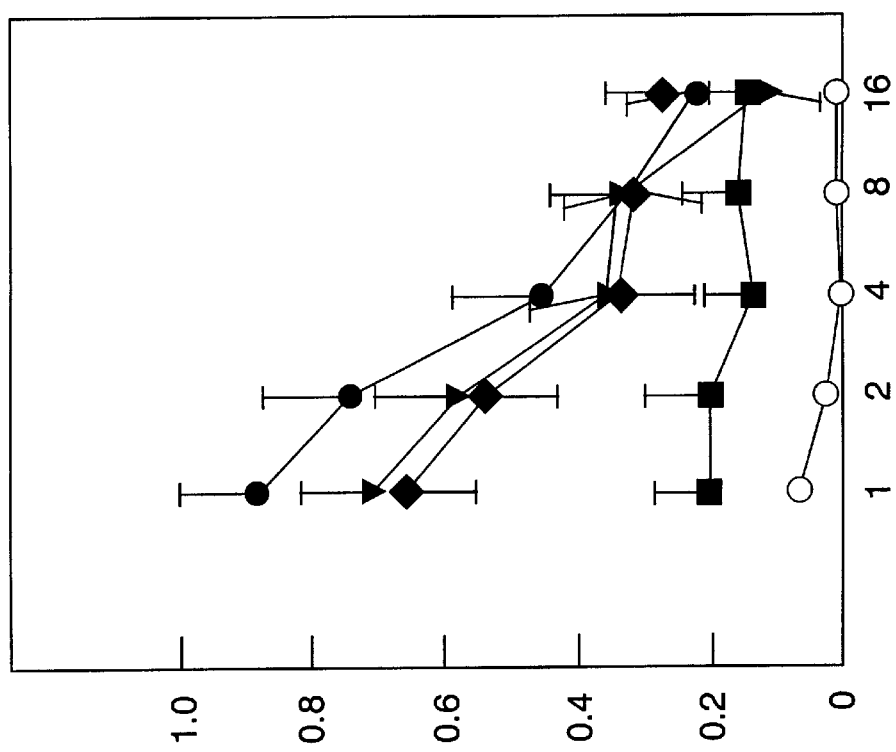
Figure 2C:
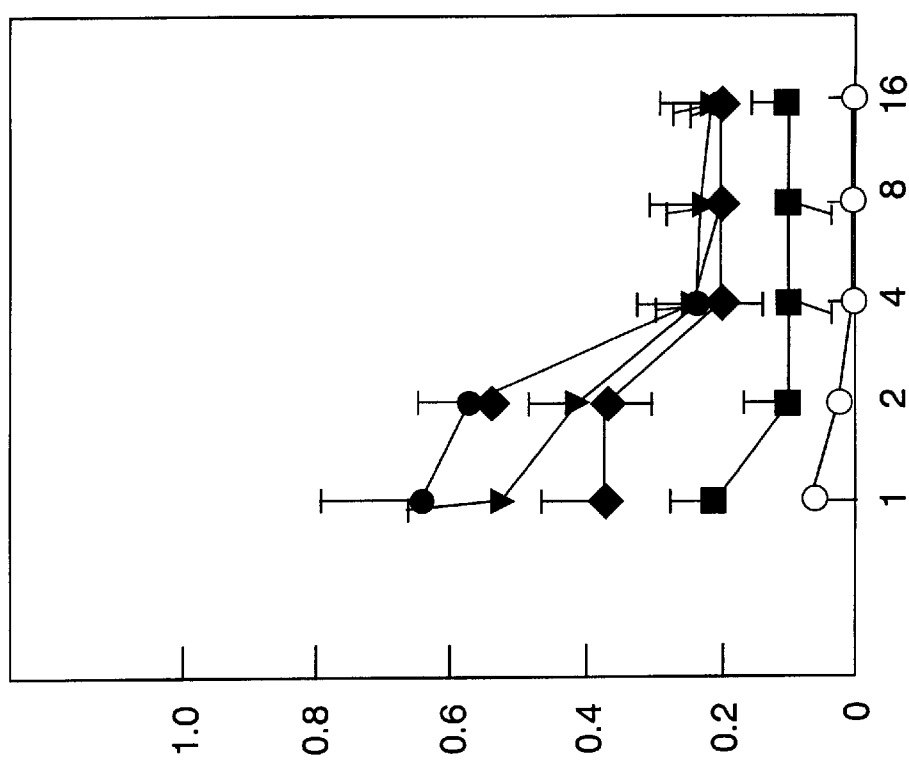

C. Anti-ganglioside IgM Response to M25 Human Melanoma Cells (first study):

Sera of BALB/c mice immunized twice with human melanoma cells (M25) had significantly elevated levels of anti-ganglioside IgM but not IgG antibodies (FIG. 1). The anti-ganglioside antibodies produced after both the first and second immunizations were predominantly IgM, a finding in agreement with a recent report (Freimer et al., 1993). The IgM antibodies reacted to all the gangliosides found in M25 cells. The IgM level was highest when LPS was attached to cells, somewhat lower (not statistically significant) with MPL attachment, and significantly lower without MPL. Phospholipid antibodies were IgM after the first immunization and IgG after second immunization (FIG. 2). The level of antibodies against all phospholipid antigens was higher when M25 cells were coated with LPS, lipid A or MPL.

Figure 3:
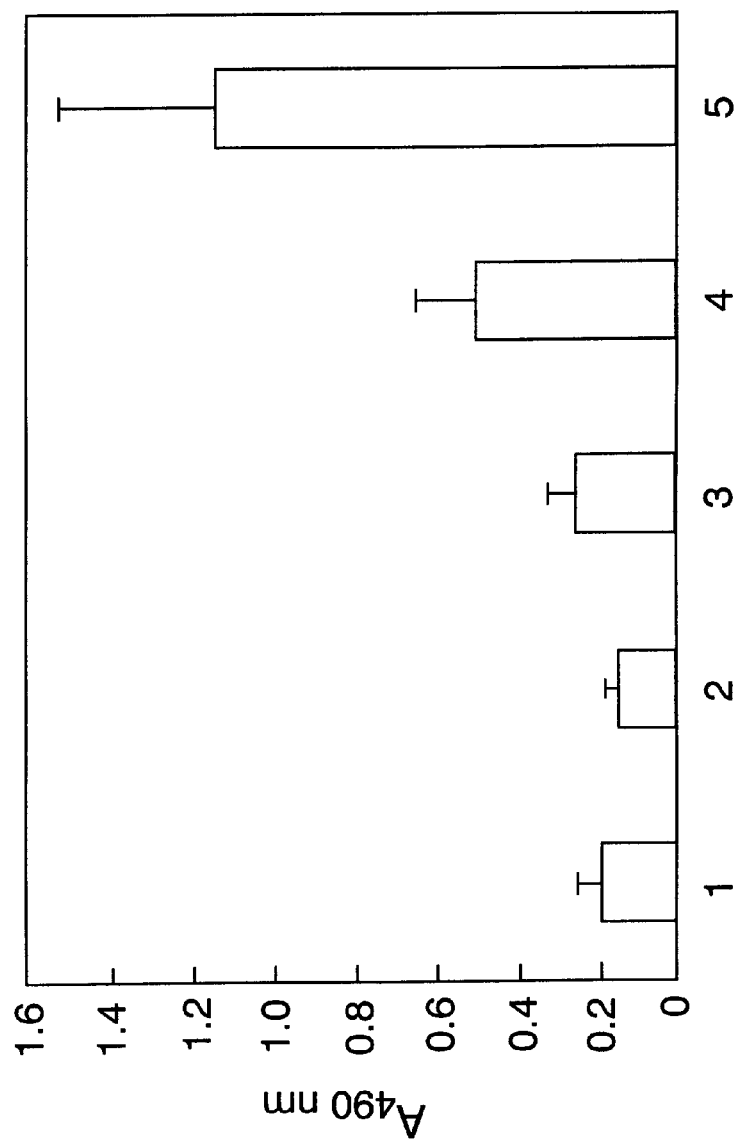
FIG. 3. Mean (±SD) ELISA absorbency ($A_{490\ nm}$, Y axis) of anti-$GM_3$ IgM antibodies in BALB\c mice after two immunization with MPL alone (1), or purified $GM_3$ alone (2), or purified $GM_3$ admixed with MPL (3), or M25 cells (4) or M25 with MPL (5). The protocol used is described in Example 2, second study. The antibody response is compared with that obtained after immunization of free tumor cells or tumor cells with MPL attached. $GM_3$ vs $GM_3$MPL (1:1000): not significant (NS); $GM_3$ vs M25 (1:1000): p=0.04; $GM_3$ vs M25-MPL (1:1000): p=0.001.
Figure 4:
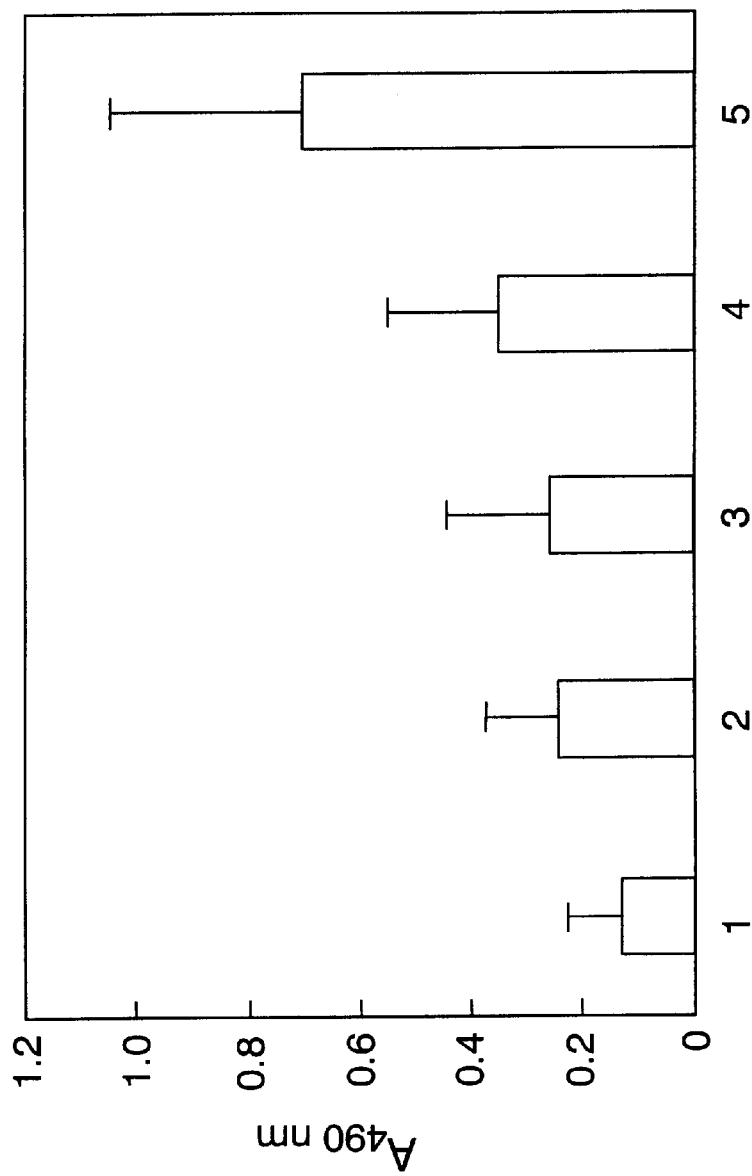
FIG. 4. Mean ELISA absorbency ($A_{490\ nm}$, Y axis) anti-$GD_3$ IgM antibodies in BALB\c mice after two immunization with MPL alone (1), or purified $GD_3$ alone (2), or purified $GD_3$-MPL (3), or M25 with MPL (5) The protocol used is described in Example 2, second study. The antibody response is compared with that obtained after immunization of free tumor cells free or tumor cells coupled to MPL. $GD_3$ vs $GD_3$-MPL (1:1000): NS; $GD_3$ vs M25 (1:1000): p=0.05; $GD_3$ vs M25-MPL (1:1000): p=0.02.

D. Anti-ganglioside IgM Response to Purified Gangliosides (in BALB/C mice) (second study):

When mice were immunized with purified free $GM_3$ or $GD_3$ with or without MPL, the anti-ganglioside IgM responses remained very low (FIG. 3 and FIG. 4). Admixing purified gangliosides with MPL did not improve the antibody response in BALB/c mice.

EXAMPLE 3

IMMUNIZATION RESPONSE IN MURINE B-16 MELANOMA CELLS

I. Materials and Methods

All materials and methods were as described in Example 1 and Example 2.

A. Immunization Schedule

All immunizations were done intraperitoneally on day 14 (first immunization) and on or after day 28 (second immunization) following pretreatment with saline. Antibody levels were measured in serum specimens collected 15 days after the first or second immunization. Each treatment group contained three mice and all treatments within each studies were conducted simultaneously. Sham controls [saline treated mice (n=3)] were used for each study.

Three 7–8 week old male C57BL/6J mice were immunized on days 14 and 28 with one of the following: 1) micelles of MPL (8 µg); 2) $GM_3$ (8 µg); 3) small unit vesicles (liposomes) of $GM_3$+MPL (8+8 µg); 4) $GM_3$+MPL (8+8+8 µg); 5) B16 cells alone or 6) B16 cells coated with MPL at 24° C. For 5) and 6) the first immunization used $2.5 \times 10^4$ viable irradiated B16 cells (200 ng of $GM_3$); the second immunization used $5 \times 10^4$ viable cells (400 ng of $GM_3$).

II. Results

A. Anti-ganglioside IgM Response to Syngeneic B16 Melanoma Cells

In the syngeneic B16 melanoma system, MPL-attached B16 cells elicited a six-fold higher anti-$GM_3$ response than MPL-free B16 cells (P<0.001) (FIG. 5 and Table 5), indicating that attaching MPL to cells significantly enhances the production of anti-ganglioside IgM antibodies.

B. Anti-ganglioside IgM Response to Ganglioside Containing Liposomes (in C57BL/6J mice)

Figure 5:
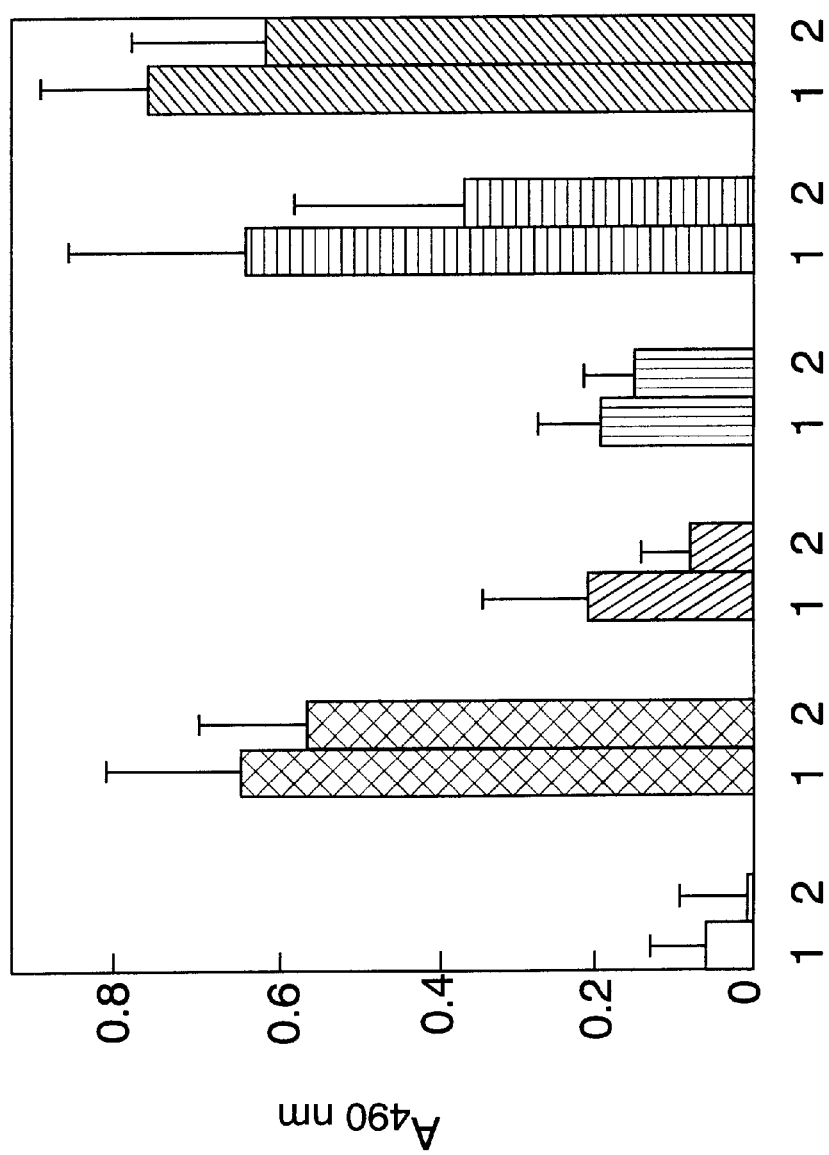
FIG. 5. Mean (±SD) ELISA absorbency ($A_{490\ nm}$, Y axis) of anti-$GM_3$ IgM antibody response is compared after immunizing (two immunizations) C57BL\6J mice with B16 (syngeneic tumor cells) (unfilled); B16 cells attached to MPL (B16-MPL) (cross-hatched); purified MPL (left to right-diagonal); purified $GM_3$ (vertical lines); $GM_3$ admixed with MPL (horizontal lines) and $GM_3$ and MPL attached to a liposome (GM$_3$-MPL-Lpm) (diagonal right to left). Note the extrinsic adjuvanticity provided by MPL. The IgM antibody titers of B16 cells with MPL attached at 1:1000 (1) or 1:2000 (2) dilutions is significantly higher (p=0.001) than with B16 cells alone. Other significant differences can be seen for GM$_3$ or MPL vs GM$_3$-MPL (1:1000): p=0.05; and GM$_3$ or MPL vs GM$_3$-MPL-Lpm (1:1000): p=0.001. The protocol used is described in Example 3. The diagonal-hatched bars are the 1:1000 serum dilution and the open (unmarked) bars are the 1:2000 serum dilution. See Table 5 for 1:1000, 1:2000 and 1:4000 serum dilution results.

The anti-$GM_3$ IgM level was significantly higher after immunization with MPL-attached ganglioside-containing liposomes versus purified ganglioside, and/or MPL (FIG. 5 and Table 5). However, the IgM response to MPL-attached GM3 liposomes (16 μg after 2 immunizations) was not superior to that obtained with MPL-attached tumor cells (0.6 μg of $GM_3$ after 2 immunizations), although a 27-fold higher amount of ganglioside was used. The data clearly documents that the adjuvanticity of MPL is pronounced when MPL is attached to natural membranes.

TABLE 5

Anti-GM3 IgM response in C57BL/6J mice.

| Immunogen | Anti-$GM_3$ IgM antibody levels (ELISA absorbency) | | |
|---|---|---|---|
| | 1:1000 | 1:2000 | 1:4000 |
| MPL (8 μg/immunization/mice) | 0.243 ± 0.028 | 0.150 ± 0.066 | 0.117 ± 0.106 |
| $GM_3$ (8 μg/immunization/mice | 0.253 ± 0.051 | 0.177 ± 0.043 | 0.118 ± 0.077 |
| $GM_3$ + MPL (8 μg-8 μg/immu/mice) | 0.621 ± 0.021 | 0.347 ± 0.008 | 0.215 ± 0.046 |
| MPL-$GM_3$ liposomes | 0.722 ± 0.033 | 0.547 ± 0.064 | 0.318 ± 0.059 |
| B16 | 0.061 ± 0.007 | 0.000 | 0.000 |
| MPL-B16 | 0.642 ± 0.068 | 0.559 ± 0.114 | 0.379 ± 0.121 |

Mice immunized with $GM_3$-MPL, $GM_3$-liposome-MPL or $GM_3$-rich irradiated B-16-MPL showed higher anti-$GM_3$ IgM antibody response than those immunized with $GM_3$ alone or irradiated B-16 cells without MPL (FIG. 5 and Table 5). The antibody response (as measured by absorbency of the sera at a particular dilution) in mice immunized with $GM_3$-MPL showed 2.5 times higher than that immunized with $GM_3$ alone. The level of antibody (as assessed by absorbency) in mice immunized with B16-MPL was ten times more than those immunized with B16 alone. The results indicate 1) the immunological crypticity of the gangliosides, as documented by significantly poor anti-$GM_3$ antibody response in mice immunized with B-16 or $GM_3$ alone, and 2) the adjuvanticity of MPL when incorporated on to natural or artificial membranes, as evidenced by high titers of anti-$GM_3$ IgM obtained after immunization with MPL-$GM_3$ or MPL-B16. MPL alone did not show any increase in anti-$GM_3$ IgM levels.

It may be noted that no anti-ganglioside IgG antibody was produced in any of these studies. Probably the pentameric nature of IgM has a effective role in clearing the tumor derived $GM_3$ from the vicinity of the tumor and from circulation than the monomeric IgG.

If antibodies generated after augmentation with MPL has the capability of clearing the shed $GM_3$, then it is reasonable to anticipate reversal of immunosuppression and restoration of immunocompetence, which should be reflected in tumor regression after immunizing with MPL incorporated membranes containing $GM_3$. Therefore, in Example 4, tumor growth was measured and survival of mice challenged with tumor after immunizing MPL-incorporated $GM_3$-expressing tumor cell membrane.

EXAMPLE 4

ANTITUMOR RESPONSE

I. Materials and Methods

All materials and methods were as described in Example 1 and Example 2.

A. Antitumor Immunity Schedule

In the first study, thirty-eight mice were immunized with 100-μl injections of one of the following: Hank's balanced salt solution (HBSS, n=9), irradiated B16 in HBSS ($10^6$ cells, n=9), irradiated B16-MPL in HBSS ($10^6$ B16 cells with 160 μg MPL, n=9), MPL in HBSS (160 μl, n=8), or Bacillus Calmette Guerin (BCG, Tice strain) +HBSS ($5\times10^6$ bacteria, n=3).

In the second study, mice were immunized with 100-ul injections of one of the following: irradiated B16-MPL in HBSS ($10^6$ cells with 160 μg of MPL, n=the same 11 as in study 1), irradiated B16-MPL in HBSS ($10^5$ with 16 μg of MPL, n=6), irradiated B16-MPL in HBSS ($10^4$ cells with 1.6 μg of MPL, n=6), irradiated B16 in HBSS ($10^6$ cells, n=the same 6 as in study 1), irradiated B16 in HBSS ($10^5$ cells, n=6) or irradiated B16 in HBSS ($10^4$ cells, n=6).

Injections were administered intradermally three times at weekly intervals. One week after the final immunization, mice were challenged subcutaneously with B16 cells whose viability had been confirmed by dye exclusion. The challenge dose was empirically determined by measuring tumor size and days of survival following subcutaneous administration of three different doses of viable B16 cells in 16 untreated mice.

Following the tumor challenge dose the mice were observed for 60 days. The size of external tumors developing at or near the inoculation site was measured with vernier calipers every other day, beginning one week after the challenge dose. The length and width of the tumor was measured; these dimensions were multiplied and their product was divided by 2. Mice dying within 60 days of tumor challenge were examined for internal tumors in the peritoneum or various organs. Mice surviving longer than 60 days were observed for an additional month before they were sacrificed and examined for internal tumor growth.

II. Results

A. Antitumor Response (restoration of immunocompetence after immunization)

In order to assess the restoration of immunocompetence of MPL incorporated to membranes, mice (C57BL/6J were immunized the with irradiated B-16 cells ($1\times10^6$) with or without incorporating MPL or MPL alone or HBSS as control. Development of immunocompetence was assessed by comparing tumor growth and survival in immunized and non immunized mice after challenging with $5\times10^3$ syngeneic B16 cells. The challenge dose was empirically determined after subcutaneous administration varying doses of alive B16 cells as shown in Table 8. No tumor development was observed in mice inoculated with $5\times10^2$ cells, suggesting the possibility of natural immunity in C57BL/6J mice against B16 melanoma cells. However, the immunity was ineffective when the challenge dose was increased by ten fold ($5\times10^3$), suggesting that the natural immunity is not strong enough to eliminate if the cell density increase to $5\times10^3$. The rate of tumor growth in mice inoculated with $5\times10^3$ cells is slower than that inoculated with $5\times10^4$ cells (Table 6). In order to assess the development of immunocompetence in mice administered with MPL or MPL-coupled to membranes, $5\times10^3$ cells was selected as the challenge dose.

Figure 6:
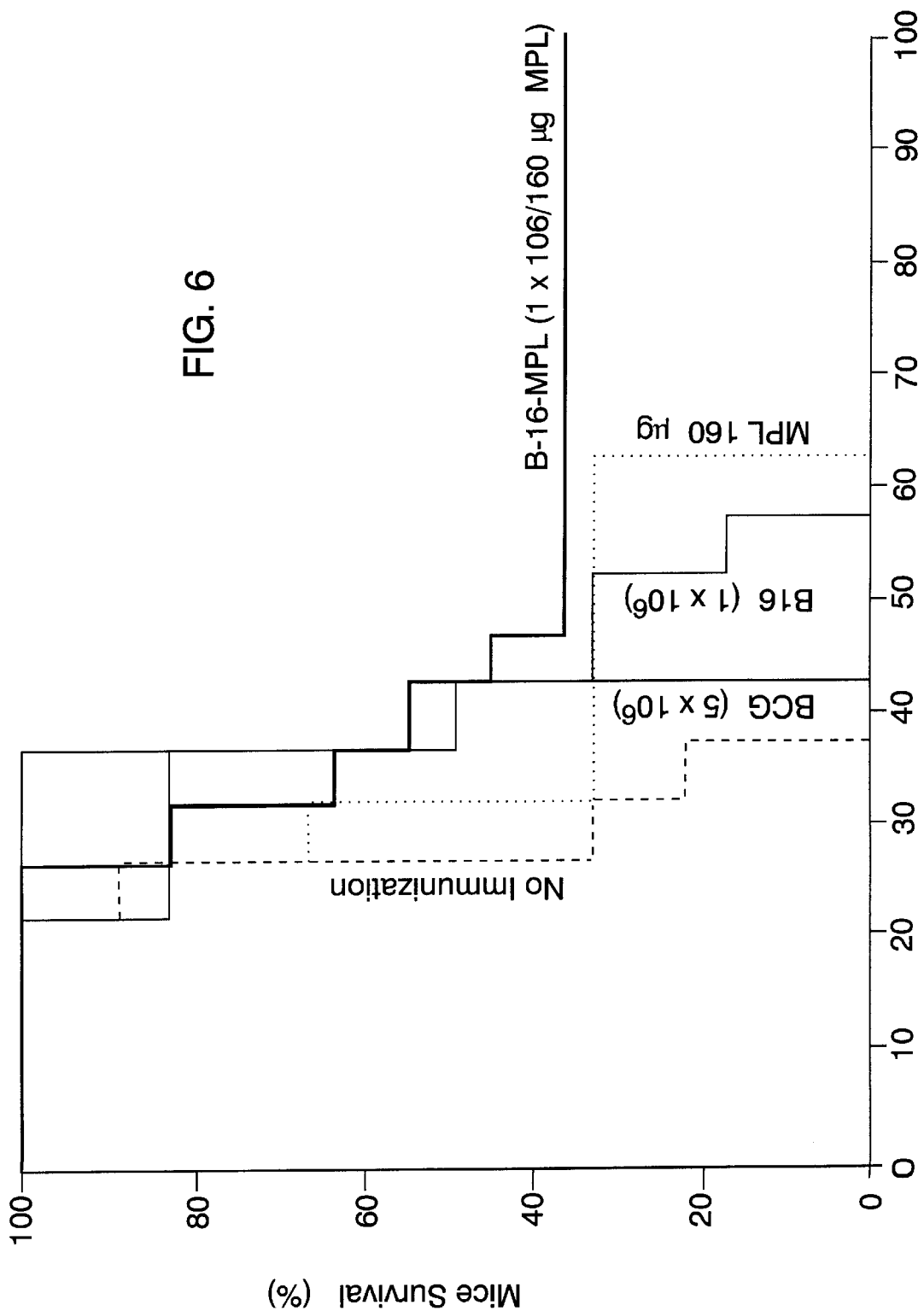
FIG. 6. Effect of immunization of MPL-incorporated irradiated B16 tumor cells on survival profile of syngeneic 7 to 8 weeks old male mouse C57BL/6J after challenge with 5×10$^3$ viable B16 tumor cells. The time axis (x axis) shows days after tumor cell (5,000) inoculation. B16 tumor cells were challenged after no immunization (9 mice); immunization with BCG (bacille Calmette-Guerin, an attenuated strain of *Mycobacterium bovis* used in a vaccine against tuberculosis and leprosy) alone (1×10$^6$) (3 mice); immunization with MPL alone (160 µg) (4 mice); immunization with irradiated B16 cells alone (1×10$^6$) (6 mice); immunization with MPL incorporated into irradiated B16 cells (160 µg of MPL into 1×10$^6$ cells) (11 mice). The immunizing compositions were administered intradermally weekly for three weeks. A week after the final immunization, alive tumor cells were challenged subcutaneously.

FIG. 6 compares survival of mice immunized with B16-MPL ($1\times10^6$) versus experiment B16 alone ($1\times10^6$). Control animals immunized with MPL or BCG alone did not restore any noteworthy immunocompetence. On the other hand, four of the eleven mice immunized with B16-coupled to MPL ($1\times10^6$) showed no evidence of tumor at all and in indeed survived a month after termination of the study (after two months). Although the sample size in this study is small, the data pertaining to tumor growth in mice immunized with B16-MPL (Table 7) further substantiate the anti-tumor effect of membrane bound MPL.

Table 7 shows the rate of tumor growth in mice immunized with various vaccines. On day 30, the tumor size is minimal in mice immunized with MPL-B-16 ($1\times10^6$) than in those immunized with B16 alone ($1\times10^6$) or MPL alone indicating that the development of immunocompetence in mice immunized with MPL-conjugated $GM_3$-rich tumor cells. Better survival and retarded growth of challenged tumor cells in mice immunized with MPL-coupled B16 in contrast to that in mice immunized with B-16 or MPL alone suggest possible reversal of $GM_3$-induced immunosuppression and restoration of immunocompetence of membrane-bound but not free MPL, or $GM_3$-rich tumor cell vaccine without MPL.

TABLE 6

Survival of host and tumor growth in 7 to 8 weeks old male mice C57BL/6J after subcutaneous administration of varying doses of alive syngeneic B16 melanoma cells.

| Number of cells administered[1] | Number of mice | Tumor size (mm$^2$) Day 17 | Day 34 | Days of Survival |
|---|---|---|---|---|
| $5 \times 10^2$ | 4 | 0 | 0 | >75 |
| $5 \times 10^3$ | 9 | 0–45 (9$^2$) | 158–350 (4$^2$) | 24–37 |
| $5 \times 10^4$ | 5 | 72–400 (5$^2$) | — (0$^2$) | 21–30 |

[1]The number of cells refer to viable cells; the cells were administered subcutaneously;
[2]Number of mice still alive.

TABLE 7

Growth of B16 melanoma tumor in 7 to 8 week old male mice C57BL/6J after various immunizations and challenge with syngeneic B16 melanona cells.

| Immunizations | Number of mice survived Day 30 | Day 60 | Tumor size (mm$^2$) Day 30 (number of mice tested) |
|---|---|---|---|
| HBSS/Saline | 3/9 | 0/9 | 220–445 (9[1]) |
| MPL | 3/4 | 0/4 | 140–240 (4[1]) |
| B16 | 5/6 | 0/6 | 48–290 (6[1]) |
| B16-MPL | 7/11 | 4[2]/11 | 15–65 (11[1,2]) |

[1]Number of mice alive on day 30;
[2]Four mice remained without tumor for more than 3 months. In B16-MPL immunized mice, the size of tumor is significantly smaller than in mice immunized with other immunogens.

It is also evident that the development of immunocompetence depends on the challenge dose of MPL-B16. A separate study was performed repeating the above study with varying doses of B16 cells ($1\times10^6$ [with 160 µg of MPL]; $1\times10^5$ [with 16 µg of MPL]; $1\times10^4$ [with 1.6 µg of MPL]). The results were compared with the same doses of B16 cells without MPL. The results (Table 8) showed that the days of survival decreased and the tumor growth increased with decreasing dose of vaccine. Mice immunized with a particular dose of MPL-B16 survived better than that immunized with corresponding dose of irradiated B16 alone.

TABLE 8

Differences in the dose dependant changes in the peraentage survival mice immunized with D16 vaccine with or without incorporating MPL.

| Treatments | n | Days of survival 15 | 25 | 35 | 45 | 55 | 65 | 75 | 85 | 95 |
|---|---|---|---|---|---|---|---|---|---|---|
| B16-MPL ($1 \times 10^6$) | 11 | 100 | 100 | 64 | 46 | 37 | 37 | 37 | 37 | 37* |
| B16-MPL ($1 \times 10^5$) | 6 | 100 | 100 | 50 | 50 | 33 | 33 | 0 | 0 | 0 |
| B16-MPL ($1 \times 10^4$) | 6 | 100 | 100 | 100 | 67 | 0 | 0 | 0 | 0 | 0 |
| B16 ($1 \times 10^6$) | 6 | 100 | 83 | 83 | 33 | 17 | 0 | 0 | 0 | 0 |
| B16 ($1 \times 10^5$) | 6 | 100 | 83 | 83 | 50 | 0 | 0 | 0 | 0 | 0 |

TABLE 8-continued

Differences in the dose dependant changes in the peraentage survival mice immunized with D16 vaccine with or without incorporating MPL.

| Treatments | n | Days of survival | | | | | | | |
|---|---|---|---|---|---|---|---|---|---|
| | | 15 | 25 | 35 | 45 | 55 | 65 | 75 | 85 | 95 |
| B16 (1 × 10$^4$) | 6 | 100 | 100 | 100 | 50 | 0 | 0 | 0 | 0 | 0 |
| No immunization | 9 | 100 | 78 | 22 | 0 | 0 | 0 | 0 | 0 | 0 |

*mice survived without any tumor.

EXAMPLE 5

QUANTITATIVE MEASUREMENTS OF MPL CONJUGATED TO CELLS

I. Materials and Methods

ELISAs in microtiter plates (Falcon 3915), were performed as described in (Ravindranath et al., 1994c). MAb 8A1, is an affinity purified murine IgG monoclonal antibody against lipopolysaccharide, obtained from Centacor Inc, 200 Great Valley Parkway, Malvern, Pa. 19355.

M101, M10 and M24 are human melanoma tumor cell lines used in the John Wayne Cancer Institute's allogeneic whole-cell melanoma vaccine. M101, M10 and M24 cells were cultured in the same manner as described for M25 cells in Example 1.

MPL purified from *Salmonella minnesota* Re595 (Ribi Immunochem Research, Hamilton, Montana) was used. For ELISAs, MPL suspended in absolute ethanol (1 mg/ml) was used. For conjugation, known quantities (ranging from 1.25 μl to 20 μl) of MPL suspended in absolute ethanol (10 mg/ml) were added to 200 μl of RPMI-1640 and sonicated. Each sonication cycle involved vortexing (3 min), sonication (30 min) at 24° C., vortexing (3 min) followed by storage at 4° C.

All other materials and methods were as described in previous examples.

II. Results

The present example describes methods to monitor the conjugation of MPL to cells and also to improve the conjugation of MPL to cells. It also shows that MPL is incorporated both onto the bilayered lipid membrane and conjugated to the cell surface proteins.

To even further improve the immunopotential of MPL conjugated cells, it is favorable to maximize the amount of MPL incorporated on the cell surface. In order to do this, the optimal ratio of MPL to cell needs to be determined. The nanogram concentration of MPL bound to cells and onto wells of microtiter plates was monitored with murine monoclonal IgG antibody 8A1.

Figure 7:
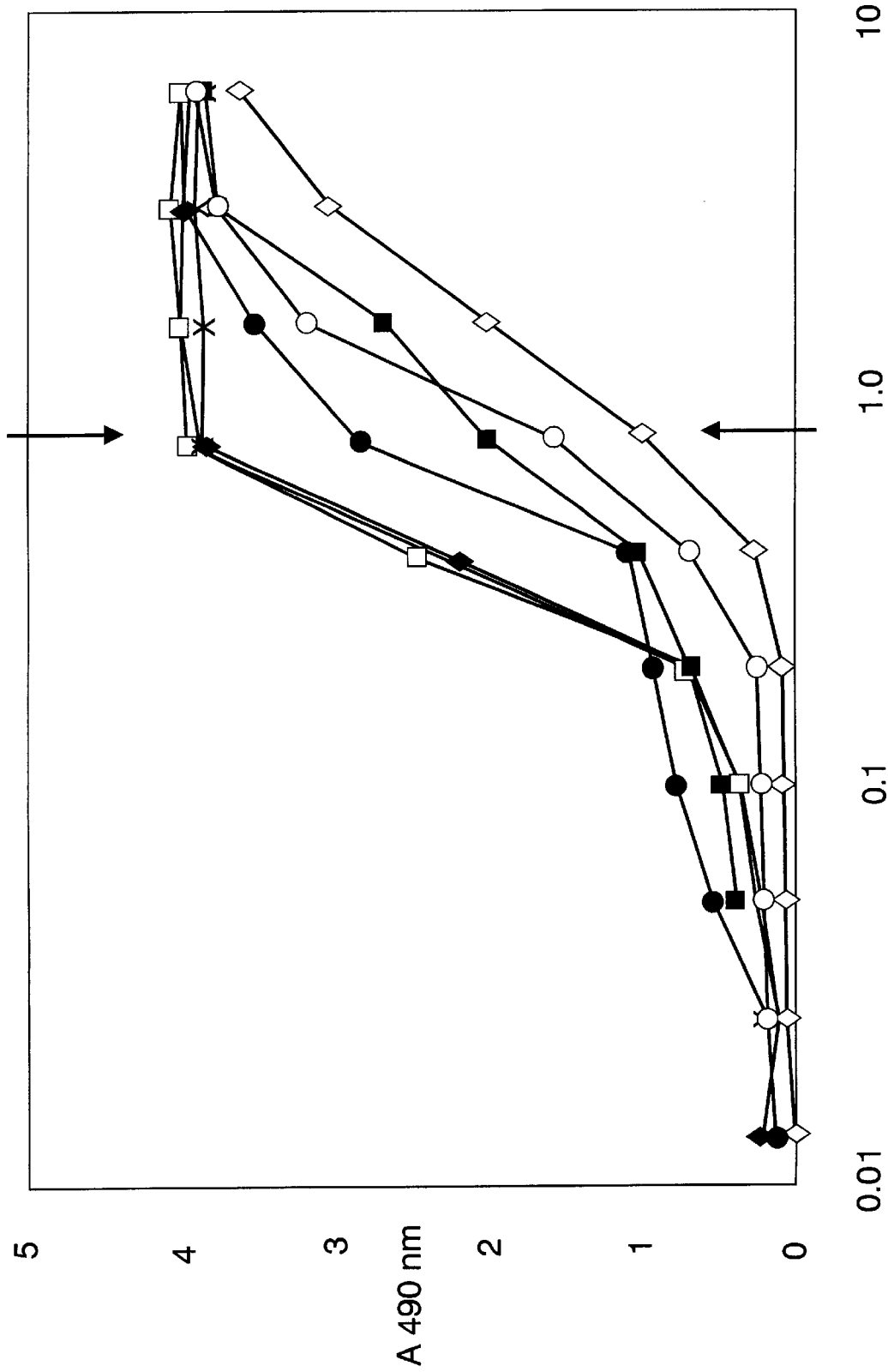
FIG. 7. Is a representative box titration of MPL with MAb 8A1 (initial concentration of 5 mg/ml). The antibody showed a linear relationship to MPL concentration at 1:32,000 or above. The arrow shows where MAb 8A1 dilutions resolve.

A box-titration of MPL with MAb 8A1 in ELISA and a titration of cell-bound MPL with different dilutions of MAb 8A1 enabled selection of a sensitive and appropriate dilution of MAb 8A1 for monitoring cell-bound MPL. Different dilutions of MAb 8A1 were first titrated against different concentrations of MPL (FIG. 7). The use of Tween-20 was found not to be necessary (FIG. 8).

In order to quantify cell-bound MPL against MPL bound to microtiter plates, the experimental conditions for monitoring MPL bound to plates and cells were kept identical. For example, the same buffer was used for washing ELISA plates and cells. The conventional use of Tween-20 for washing microtiter plates was avoided, since there was no difference in the performance of the wash buffer with or without Tween-20.

Figure 9:
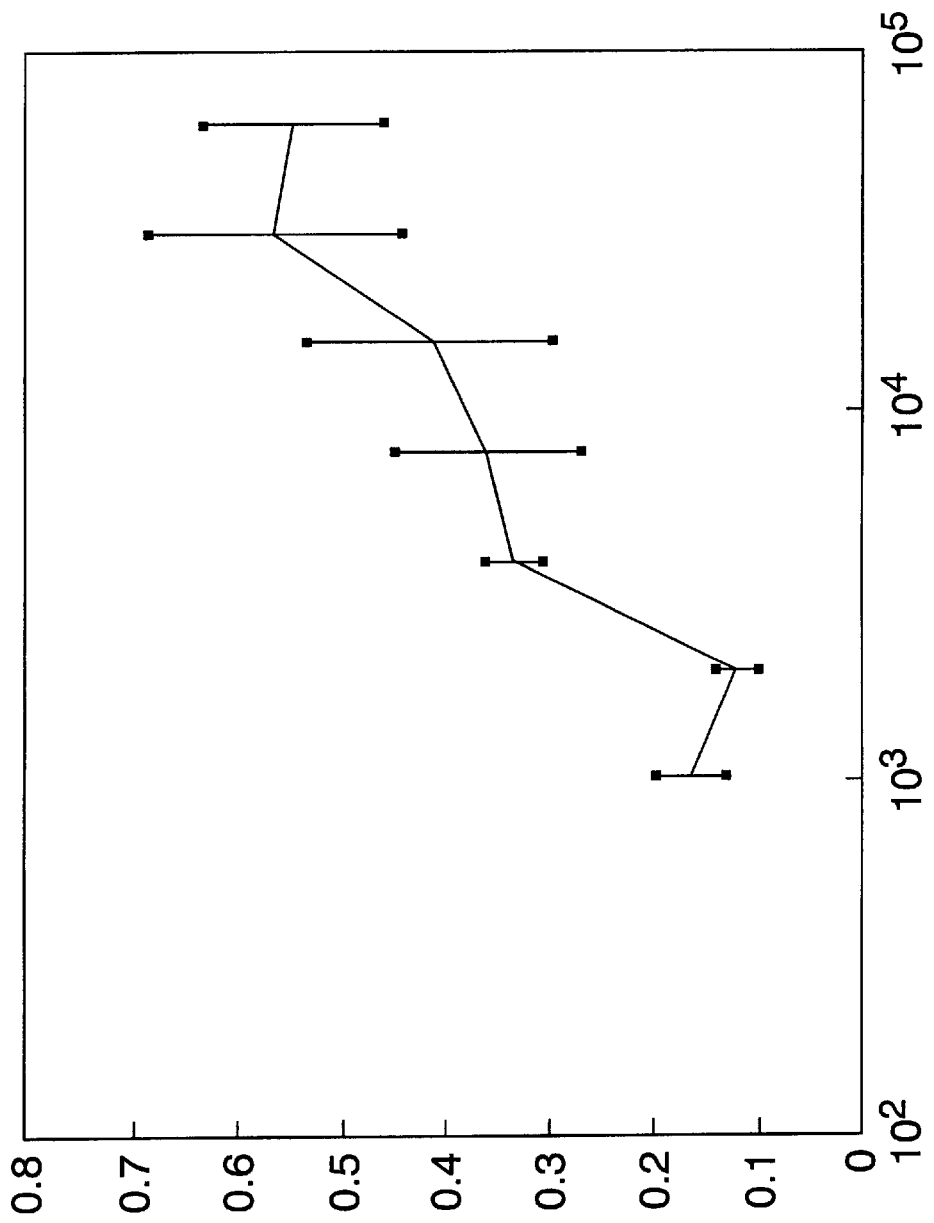
FIG. 9. Binding of MAb 8A1 with MPL conjugated to a cell line using ELISAs. Different dilutions of MAb 8A1 were titrated against the same concentration of MPL conjugated M101 tumor cells. At lower dilutions, 8A1 is not sensitive because of the high background. The background is significantly minimized at dilutions of 1:32,000 (p<0.01) and 1:64,000 (p<0.05). p values are obtained after Bonferroni adjustment. At these dilutions, the values are reproducible and consistent. The MAb 8A1 dilution recommended for monitoring the MPL conjugated tumor cells is 1:32,000. n =4 (Bonferri p values); 1:1000 vs. 1:32,000=p<0.05; 1:2000 vs. 1:64,000=p<0.05.

When titrating different dilutions of MAb 8A1 against the same concentration of MPL-conjugated M101 tumor cells, 1:32,000 proved to be the most sensitive MAb 8A1 dilution (FIG. 9). At lower dilutions, 8A1 is not sensitive because of the high background. The background is significantly minimized at dilutions of 1:32,000 (p<0.01) and 1:64,000 (p<0.05). The 1:32,000 dilution gave reproducible results in quantifying MPL conjugated to cells. Thus a single-point quantitation ELISA assay, with 0.8 nanogram of MPL and 1:32,000 dilution of MAb 8A1, is recommended for routine monitoring.

After establishing a reproducible and sensitive assay, the inventors then optimized MPL conjugation to cells. The previous difficulties in this work were the amphipathic nature of MPL, that made it poorly soluble in aqueous media, and the fact that typical solvents, such as triethanolamine, could not be used—due to the intended development of human therapeutics.

Figure 10:
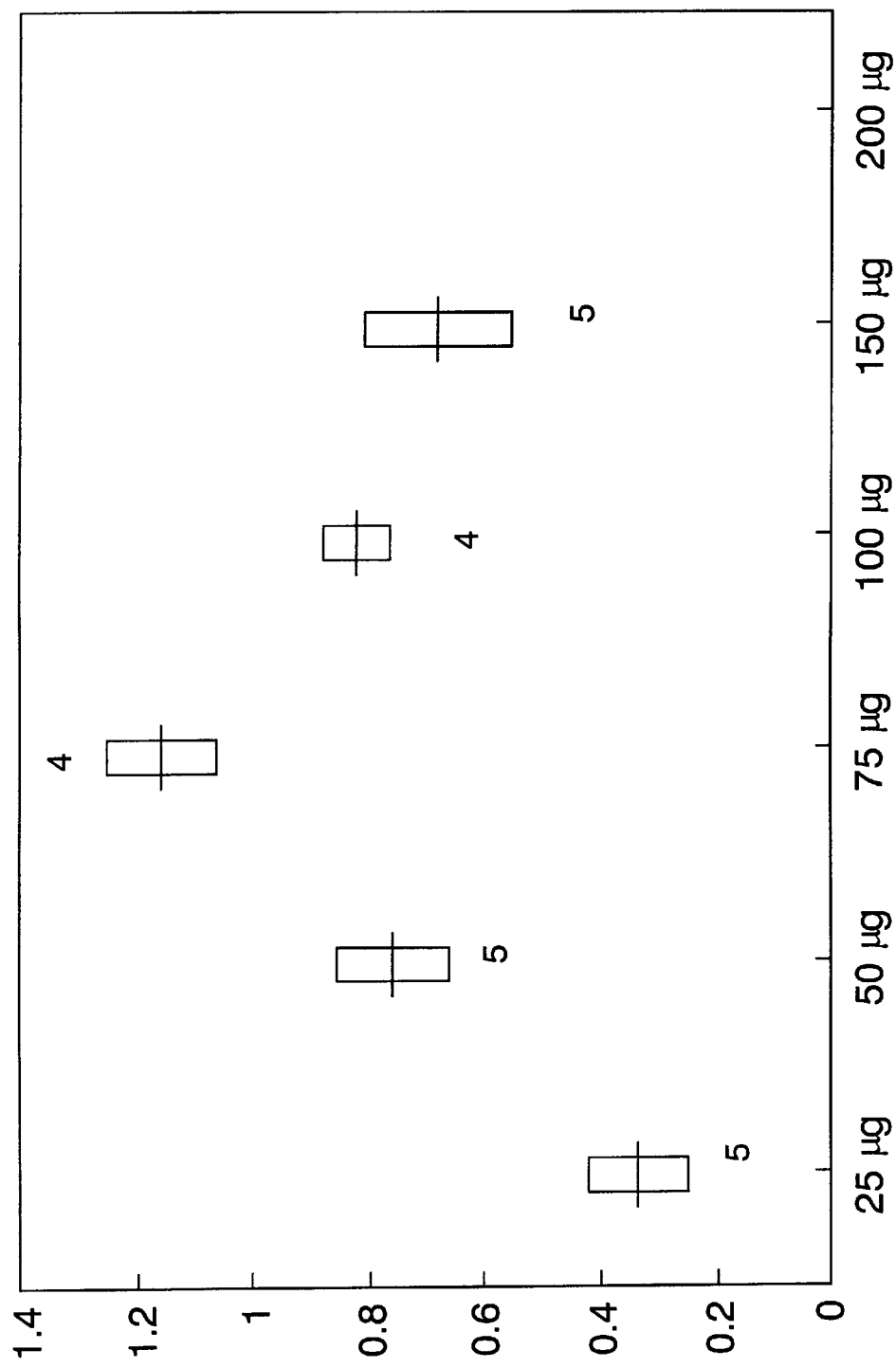
FIG. 10. Quantification of MPL dosimetric conjugation to M101 cells after a single sonication cycle. MPL conjugated to cells in values of ng/half million cells is shown against ng of MPL provided to cells. MPL is conjugated to cells following mixing of various amounts of MPL with 1 million cells. Maximum binding occurs when 75 µg of MPL is added to 1 million cells in 300 µl of RPMI 1640 incubation medium.

The inventors thus developed an adjuvant-suspended culture media by sonicating MPL. Known quantities of MPL were suspended in absolute ethanol, added to 200 μl of RPMI-1640 and sonicated. Each sonication cycle involved vortexing for 3 min., sonicating for 30 min. at 24° C., vortexing again for 3 min, and then storage at 4° C. On mixing the MPL-suspended culture media with 1 million M101 cells, effective binding was observed. Maximum binding occurred using 75 μg of suspended MPL when added to 1 million cells in 300 μl of RPMI 1640 incubation medium (FIG. 10).

The maximum amount of MPL conjugated to M101 tumor cells was found to be about 2.3 ng MPL per million cells (just under 1.2 ng MPL per 0.5 million cells; FIG. 10). The 0.5 million cell number accounts for the loss of cells during the washing period. Importantly, conjugation of MPL can be increased without addition of any cytotoxic chemicals.

Figure 11:
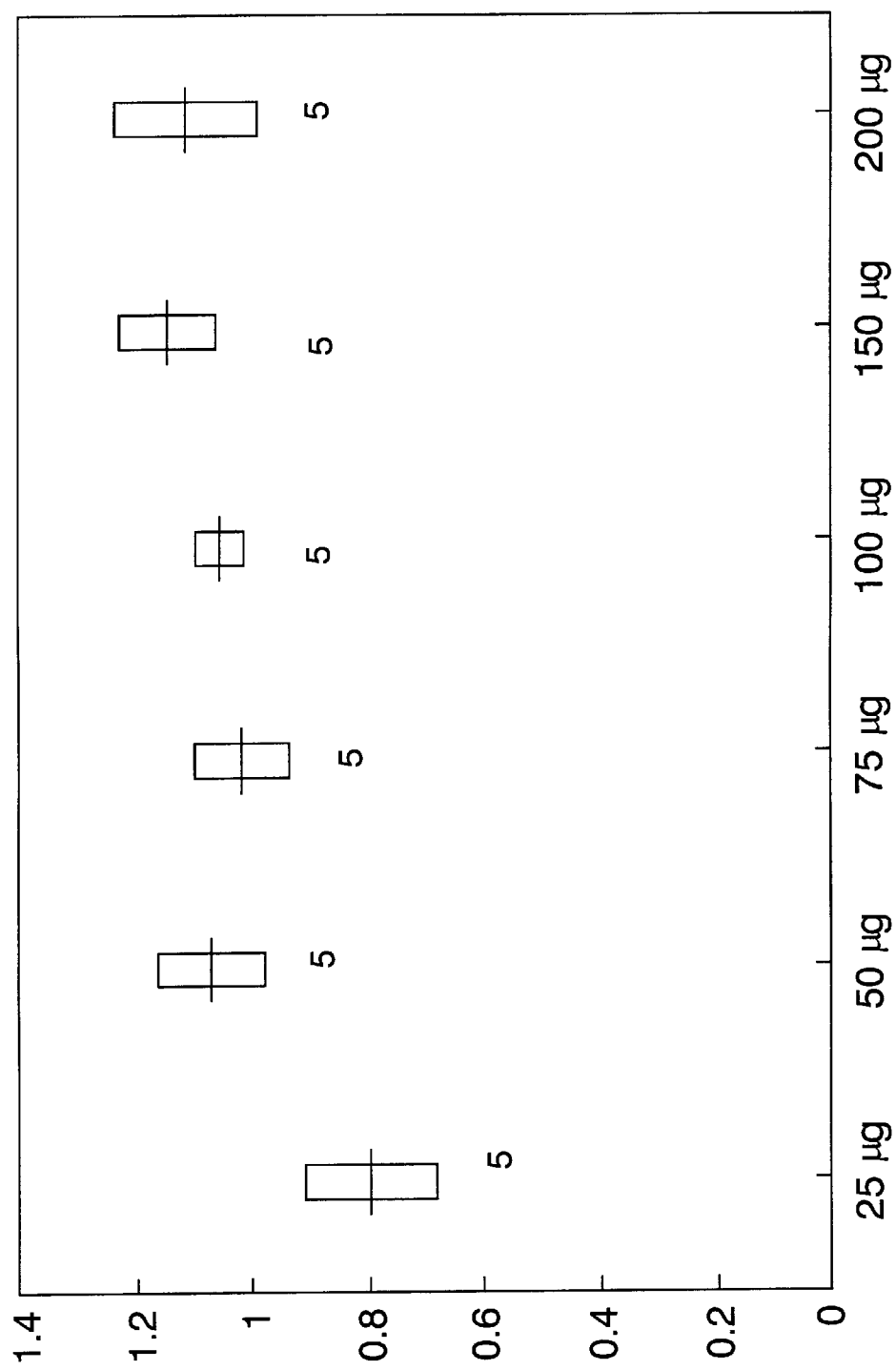
FIG. 11. Quantification of MPL dosimetric conjugation to M101 cells after three sonication cycles. MPL conjugated to cells in values of ng/half million cells is shown against ng of MPL provided to cells. MPL is conjugated to cells following mixing of various amounts of MPL with 1 million cells. Binding is improved by increasing to three sonication cycles. The concentration of MPL in the incubation medium can also be effectively reduced. Adding 50 µg of MPL per million cells, and even 25 µg of MPL per million cells is effective.

In an even further improvement, MPL conjugation to M101 cells was found to be increased after three sonication cycles (FIG. 11). Using three sonication cycles, the concentration of MPL in the incubation medium can also be effectively reduced. Here, adding 50 μg of MPL per million cells, or even 25 μg of MPL per million cells, is also effective.

The amounts of MPL conjugated to tumor cells was now found to be more consistently in the 2.2 to 2.3 ng MPL per million cells range (consistently over 1 ng MPL per 0.5 million cells; FIG. 11). Even using 25 μg of MPL in the medium gave 1.6 ng MPL conjugated per million cells (FIG. 11).

Figure 12:
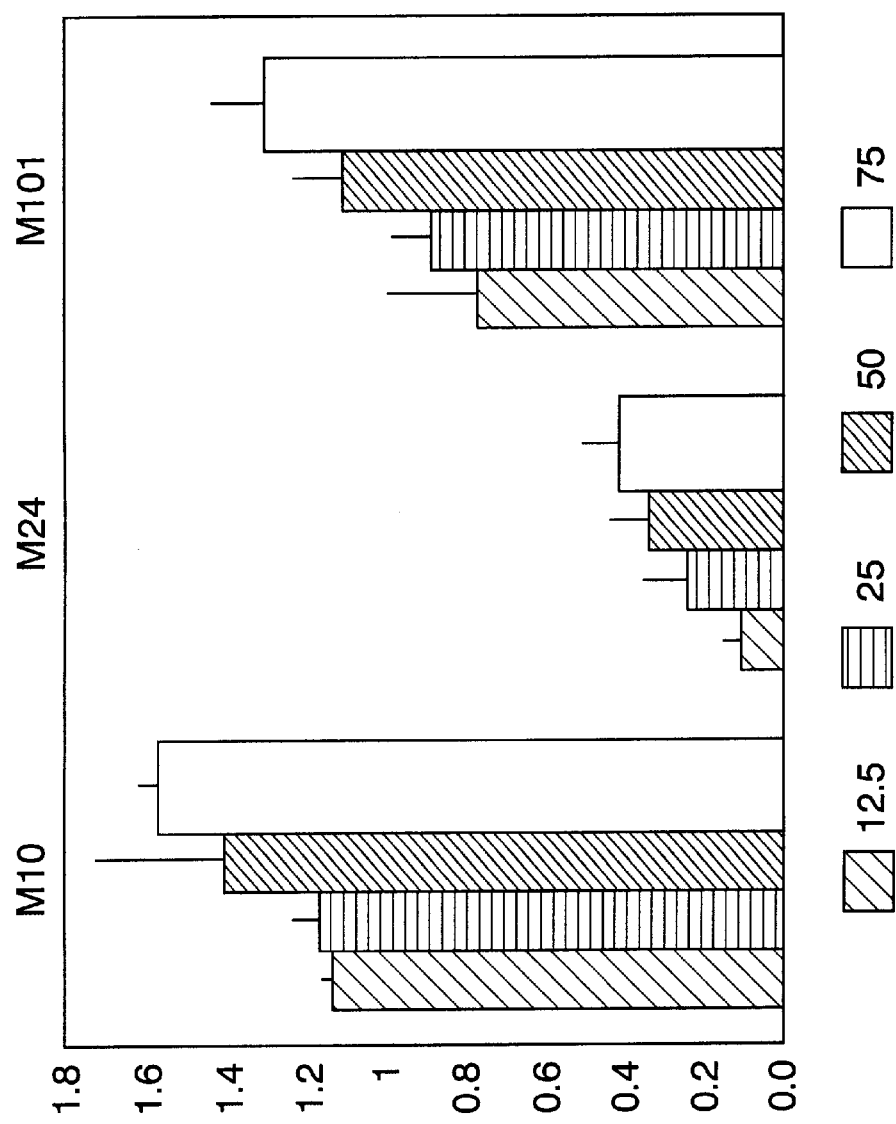
FIG. 12. Conjugation of MPL to different melanoma cells. M10, M24 and M101 cells were incubated with the concentrations of MPL shown; n=5. MPL conjugated to cells in values of ng/half million cells is shown against ng MPL provided to cells. ELISAs were performed to detect the presence of cell-bound MPL. The three sonication cycle method was employed. Dosimetric increases in conjugation of MPL was observed using three different human cell lines used in active specific immunotherapy of melanoma. MPL conjugates to M10 and M101 better than to M24.

It was next determined whether MPL may be effectively conjugated to other tumor cells. As shown in FIG. 12, conjugation of MPL to M10, M24 and M101 cells was achieved. Dosimetric increases in MPL conjugation were observed using these three different human cell lines. Using M10 levels of just over 3.1 ng per million cells were attained. MPL conjugates to M10 and M101 better than to M24. However, even the levels achieved using M24, over 0.8 ng MPL per million cells, are useful. The data in FIG. 10, FIG. 11 and FIG. 12 were produced in three different studies. The mean results are within the SD in all cases.

It was lastly determined whether MPL, conjugated to tumor cells, binds to the bilayered lipid membrane, to cell surface proteins or to both. M101 tumor cells were trypsinized (0.01% trypsin at 37° C. for 30 min.), either before MPL was conjugated to the cell surface or after conjugation (FIG. 13), and ELISAs with MAb 8A1 were performed to detect the presence of cell-bound MPL. As trypsin cleaves extracellular proteins, it therefore removes any easily accessible surface proteins from the cell. MPL conjugated to a tumor cell prior to enzyme treatment, may thus bind to either protein or lipid membrane. However, MPL conjugated to tumor cells after enzyme treatment, may only bind to the lipid membrane.

Figure 13:
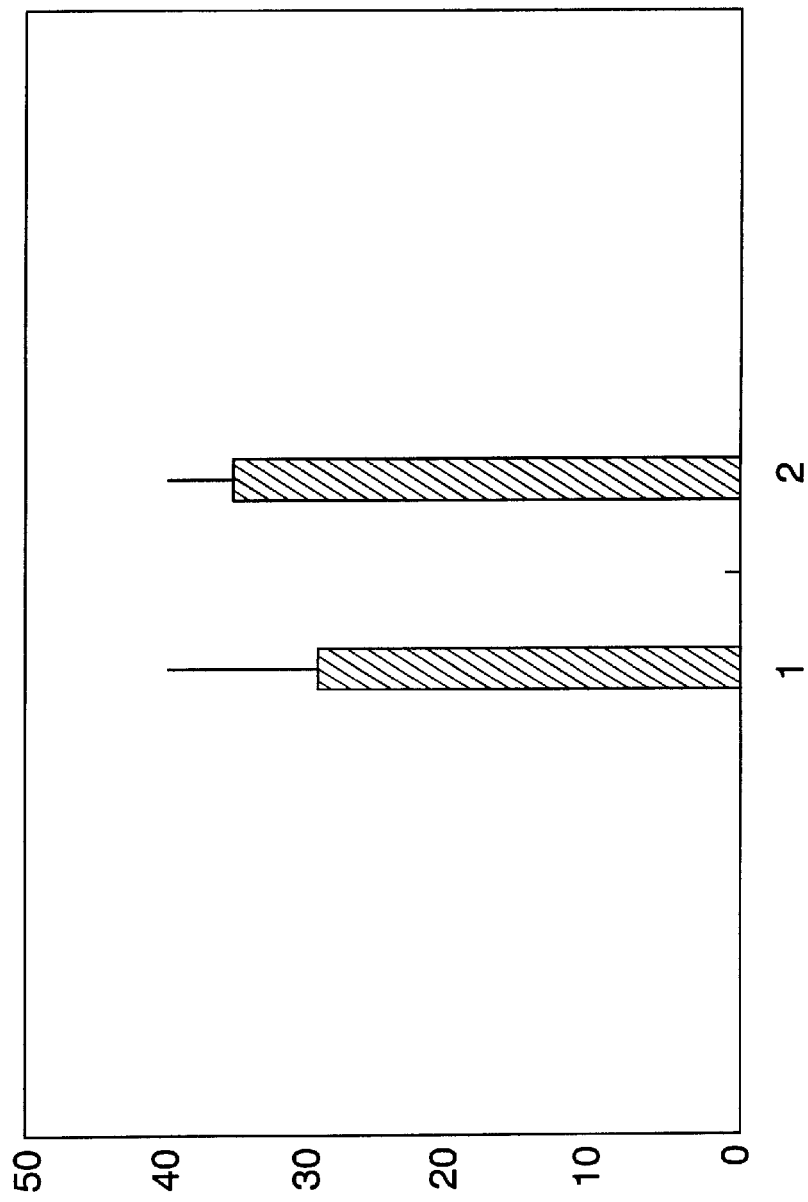
FIG. 13. Site of conjugation of MPL to M101 cells. Cells were treated with 0.01% trypsin at 37° C. for 30 minutes either before or after conjugation with MPL. ELISAs with MAb 8A1 were performed to detect the presence of cell-bound MPL. About 30% to 35% of MPL was bound to cells even after trypsinization by two different methods. The ratio of MPL-binding to cell surface proteins vs. bilayered lipid membranes is 2:1.

The results shown in FIG. 13 indicate that MPL binds to both cell surface proteins and the bilayered lipid membrane, in a ratio of approximately 2:1. About 30% to 35% of MPL was bound to cells even after trypsinization by two different methods. As MAb 8A1 detects the diglucosamine-phosphate residues in MPL, this suggests that it is the fatty acid portion [hydrophobic] domain that is bound to cell surface proteins or incorporated onto the bilayered lipid membrane. Otherwise the antibody would not be able to detect MPL, conjugated to cells.

The quantitative measurement of the amount of monophosphoryl lipid A conjugated to cells is important for increasing the immunogenicity and antitumor activity of the MPL-cell conjugate. Maximizing conjugation of adjuvant to cell, presupposes, maximizing the immunopotency of the cell.

EXAMPLE 6

CRYOPRESERVATION OP ADJUVANT-INCORPORATED TUMOR CELLS

The present example shows that cryopreservation of MPL-incorporated tumor cells does not affect the binding of MPL to the cells.

Figure 14:
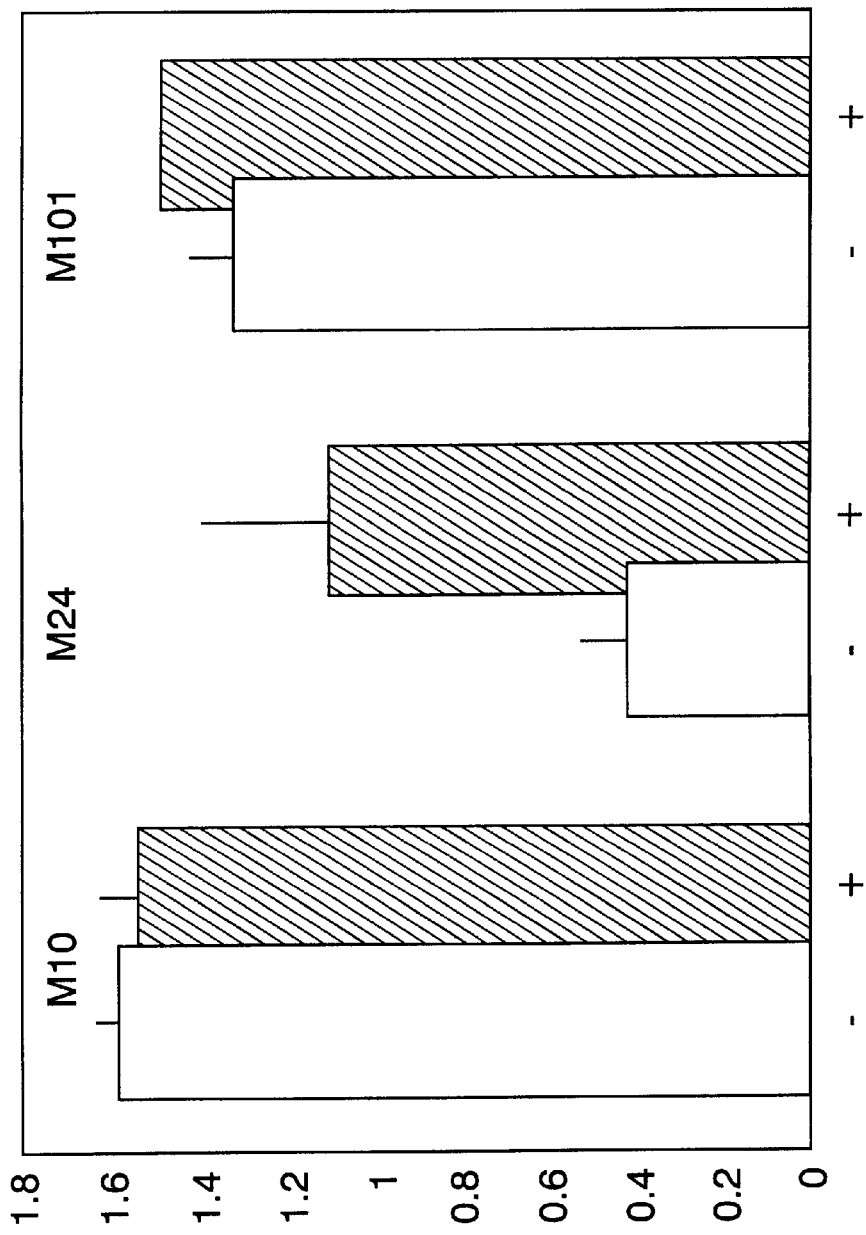
FIG. 14. Histogram to show that freezing with 0.1% dimethylsulfoxide (DMSO), storage at –70° C. and thawing do not affect the quantity of MPL bound to melanoma cells. The values in "y" axis refer to bound MPL (expressed as nanogram/0.5 million cells). Bound MPL on cells with (+) and without (–) freezing, storage at –70° C. and thawing are compared. The values for each protocol were corrected for background (values obtained for cells without MPL, due to non-specific binding of monoclonal antibody 8A1). Each bar represents the mean of four values.

Samples of the adjuvant-incorporated melanoma cells, M10, M24 and M101, were frozen with 0.1% dimethylsulfoxide (DMSO, a commonly used agent to cryopreserve cells), stored at –70° C. and then thawed. The amount of MPL bound per 0.5 million cells was then compared to that bound to cells that had not been freeze-thawed. FIG. 14 shows that dimethylsulfoxide (DMSO, commonly used to cryopreserve cells), storage at –70° C. and thawing do not affect the quantity of MPL.

This finding is important because tumor cell therapeutic formulations are generally cryopreserved, e.g., in dilute dimethylsulfoxide (DMSO) and stored in –70° C. indefinitely. Prior to immunization, the therapeutic cell formulation, or "vaccine", is taken out, thawed, washed and administered. This example shows that such harsh treatment does not have significant adverse effects on the MPL bound to cells. Therefore, cryopreservation will not affect the levels of MPL bound to the tumor cells.

EXAMPLE 7

FLUORESCENCE ACTIVATED CELL SORTER (FACS) ANALYSIS.

The present example provides further direct evidence of the incorporation of MPL onto tumor cell surfaces.

Figure 15A:
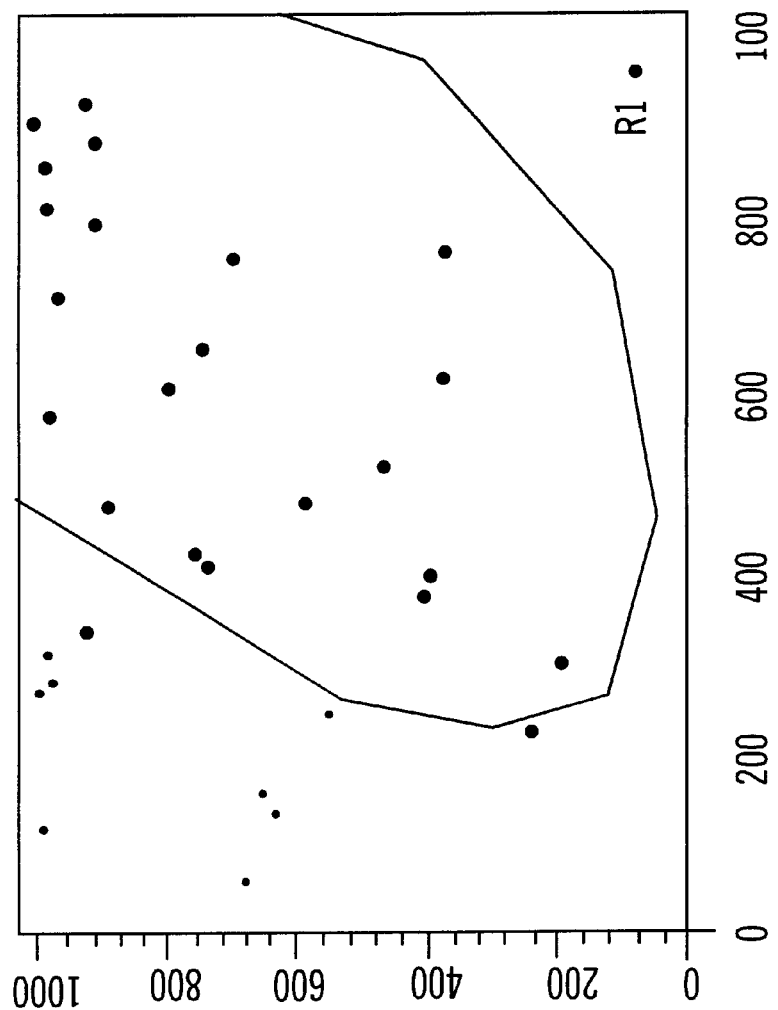
FIG. 15A, FIG. 15B and FIG. 15C. Fluorescence Activated Cell Sorter (FACS) analysis of MPL incorporated melanoma cells (M101).
Figure 15B:
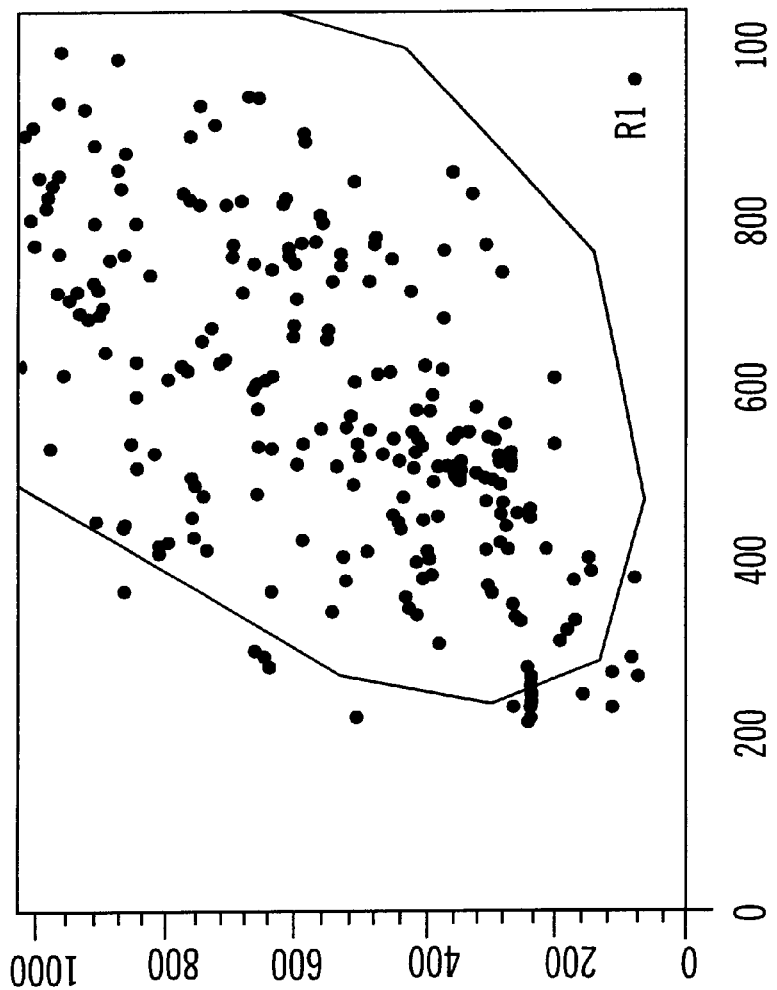
Figure 15C:
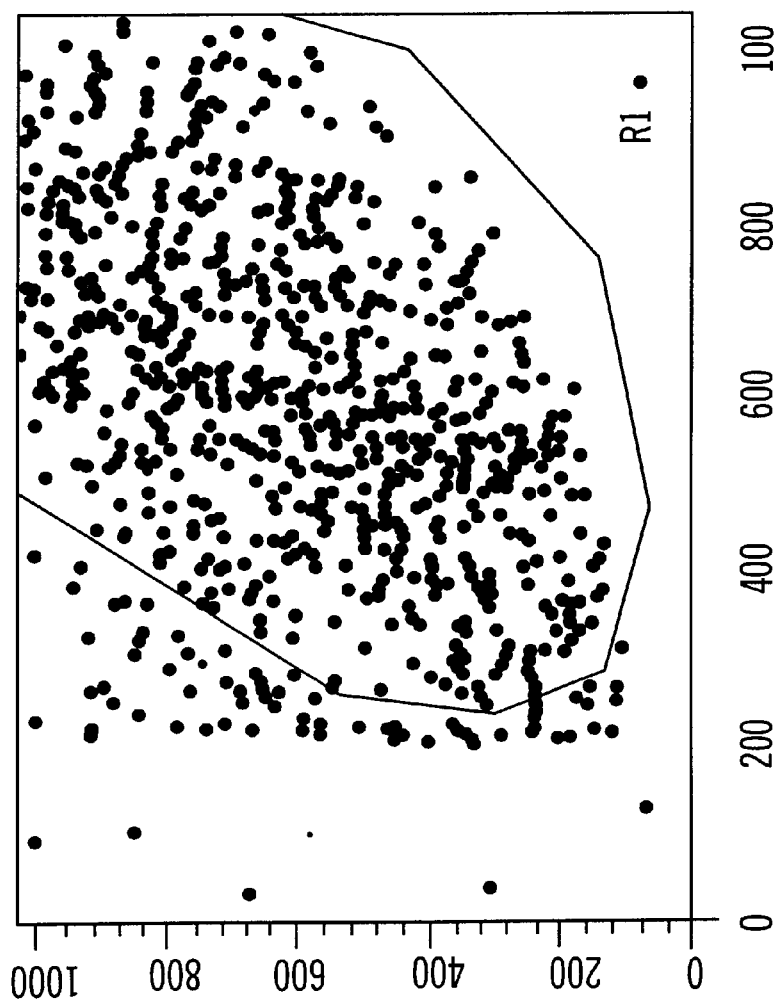

Samples of adjuvant-incorporated melanoma cells were subjected to FACS analysis using a protocol essentially same as that presented for ELISA. After incorporating MPL, and adding MAb 8A1, the presence of MPL on the cell surface was visualized with a second antibody coupled to the fluorescent dye, FITC (fluorescein isothiocyanate). A comparison of FIG. 15A, FIG. 15B and FIG. 15C shows that cells incorporated with MPL do have MPL available on the cell surface, as assessed by staining with MAb 8A1 and the antibody coupled to FITC. In FIG. 15C, the dots represent cells having MPL on their surface. This is in contrast to FIG. 15A and FIG. 15B that show non-specific binding of the FITC-coupled second antibody and the non-specific binding of the MAb 8A1, respectively. Table 9 represents the design of the FACS analyses.

TABLE 9

Plan of FACS analysis

| Numbers Treatments | A Blank | B Control | C Study |
|---|---|---|---|
| M101 cells (1 M) | + | + | + |
| MPL | – | – | + |
| MAb 8A1 | – | + | + |
| FITC-antiMouse IgG | + | + | + |

The gating was recorrected after comparison of the profiles of blank, control and experimental.

EXAMPLE 8

INTERNALIZATION OF ADJUVANT

The present example presents evidence to document that a fraction of an adjuvant, such as MPL, when incorporated onto tumor cell surface, is also endocytosed or taken in.

An adjuvant was incorporated onto cells at two different temperatures, 4° C. and 37° C. At low temperatures, the metabolic activities, such as endocytosis, are known to be lower than at higher temperatures. At 37° C., such activities are at peak for cells. By incorporating adjuvant at low temperatures, such as 4° C., the adjuvant may be expected to stay on the surface. On the other hand, at 37° C., the inventors contemplated that there was a good chance for internal uptake of the adjuvant.

Incorporation was assessed at two different temperatures. Two different methods were used to assess the incorporation: one method, described in Example 5, is essentially based on the ELISA principle. The other method is Fluorescence activated cell sorting [FACS]. FACS, as described in Example 7, documents fluorescence, and hence adjuvants, present on the cell surface.

The design of the temperature studies is shown in Table 10. The results of MPL incorporation at two different temperatures by two methods are presented in Table 11. The table shown results obtained with four samples and their mean values. ELISA values are presented as O.D. or absorbency [at A 490 nm]. FACS values are presented as events, which signify the number of cells showing high density expression of fluorescence due to FITC-conjugated second antibody binding.

TABLE 10

Plan of Temperature -- Incorporation Analyses.

|  | Blank | Control | Study |
|---|---|---|---|
| Cells | + | + | + |
| MPL | – | – | + |
| MAb 8A1 antibody | – | + | + |
| FITC-coupled 2° antibody | + | + | + |

The results of Blank, Control and Table 10 shows the components that were included in each of the temperature analyses. The results of Blank, Control and conjugation studies (four sets and mean) are presented in the Table 11.

TABLE 11

Adjuvants are Incorporated Intracellularly. Differences in the incorporation of MPL to M24 melanoma cells at different temperatures: Differences between the results obtained vith ELIBA and FACS

| Treatments | ELISA [O.D.] 4° C. | ELISA [O.D.] 37° C. | FACS [events] 4° C. | FACS [events] 37° C. |
|---|---|---|---|---|
| Blank-1 | 0.233 | 0.264 | 83 | 100 |
| Blank-1 | 0.261 | — | 79 | — |
| Control-1 | 0.615 | 0.597 | 179 | 111 |
| Control-2 | 0.680 | 0.398 | 132 | 97 |
| Control-3 | — | 0.539 | — | 88 |
| Study-1** | 1.265 | 1.800 | 911 | 630 |
| Study-2 | 1.474 | 1.866 | 1117 | 485 |
| Study-3 | 1.285 | 1.832 | — | 771 |
| Study-4 | 1.363 | 1.502 | 1091 | 551 |
| mean of four studies [control adjusted] | 1.095 | 1.497 | 884 | 509 |
| Standard Deviation | 0.094 | 0.168 | 112 | 123 |
| t-test unpaired two-tailed (p value) | | <0.01 [>4° C.] | | <0.01 [>4° C.] |

**(ELISA absorbency [O.D.] 1.515 represents incorporation of 0.8 nanogram of MPL to 0.5 million cells).

MPL incorporation as assessed by absorbency [as in ELISA] or by events [as in FACS] are seen to be different between the two temperatures. In the ELISA system, MPL incorporation is significantly [p<0.01] higher at 37° C. than at 4° C. In the FACS system, MPL incorporation is significantly [p<0.01] lower at 37° C. than at 4° C.

FACS analysis clearly documents cell surface incorporation of MPL. MPL incorporation is significantly lower at 37° C. than at 4° C. This data may theoretically signify two possibilities: (1) incorporation is poor at higher temperature; or (2) incorporated MPL has been internalized. Conceptually, one would think it unlikely that incorporation would be poor at high temperature, and this is supported by the ELISA data.

In an ELISA, the intensity of oxidized substrate is measured. The oxidation occurs due to the peroxidase coupled second antibody bound onto the cell surface or due to oxidation of substrates by internalized peroxidase coupled second antibody. This possibility is greater because the pH of the substrate is 5.0, which is acidic and would have caused sufficient necrosis to release the internalized enzyme after addition of substrate.

Therefore, the significant increase in absorbency [or O.D.] at 37° C. than at 4° C. is likely due to internalization of the adjuvant-antibody complex. This correlates with the decrease in surface incorporation measured by FACS. This shows that when adjuvant is added for incorporation at higher temperatures, there is internalization of the adjuvant.

This study, establishing that an adjuvant is not only incorporated onto cell surface but also internalized during incorporation, has important implications. When adjuvant-internalized cells are to be phagocytosed by antigen presenting cells, and when the antigens are degraded for presentation by MHC class I and II molecules, the adjuvant, such as MPL, may also be presented on the cell surface. When this occurs, the adjuvant can function as an immunostimulatory or co-stimulatory molecule. This strategy is particularly useful in cancer vaccine preparations as many cancer cells used as vaccines contain internal antigens, such as Mage I in human melanoma. Further examples of intracellular cancer antigens are presented in Table 12 (Houghton, 1994).

TABLE 12

Intracellular Human Cancer Antigens.

| Antigen | Tumor Type | Citation |
|---|---|---|
| gp75/brown | Melanoma | Brichard et al. (1993) |
| Melanotransferrin | Melanoma | Real et al. (1984) |
| MAGE-1,3 | Melanoma, lung, and other cancers | van der Bruggen et al. (1991); Gaugler et al. (1994) |
| Tyrosinase/albino | Melanoma | Kawakami et al. (1994) |
| MUC1 | Pancreas, breast | Bamd et al. (1989); Vijayasaradhi et al. (1990) |
| Melan-A/MART-1 | Melanoma | Coulie et al. (1994); Kawakami et al. (1994); Bakker et al. (1994) |

As an adjuvant can be incorporated both externally (as on cell surface) and internally (as in cytosolic fraction) to improve antigen presentation and immunostimulation, bacterial enterotoxins and exotoxins, which are considered as superantigens, can be used as adjuvants. As the inventors' present technology facilitates internal and external incorporation of the adjuvant, it is particularly suitable to the development of bacterial superantigens in adjuvant therapy.

EXAMPLE 9

PRODUCTION OF ANTIBODIES TO CELLS INCORPORATING ADJUVANTS

In general, means for preparing and characterizing antibodies are well known in the art (See, e.g., Antibodies: A Laboratory Manual, Cold Spring Harbor Laboratory, 1988; incorporated herein by reference). However, in that certain antigens are immunologically cryptic, new methods of antibody generation are still being sought. One example of poorly immunogenic antigens are the tumor related gangliosides. Such molecules generally do not elicit a satisfactory antibody response when given to experimental animals, including when administered as free ganglioside compositions, as gangliosides admixed with standard adjuvants, and even when given in artificial membrane form.

In light of the present invention, the standard methods for generating polyclonal antibodies and MAbs can be manipulated to promote an antibody response against an antigen by immunizing the animal with a composition in which an adjuvant, e.g., MPL, is incorporated into a cell membrane.

To prepare a polyclonal antibody using an immunogenic cellular composition in accordance with this invention, one immunizes an animal with an effective amount of the immunogenic adjuvant-incorporated cell composition. Antisera is then collected from the immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies. A variety of routes can be used to administer the immunogen (subcutaneous, intramuscular, intradermal, intravenous and intraperitoneal).

Optimizing the amount of the composition administered to an experimental animal will be a routine matter known to those of skill in the art in light of published methods and the present disclosure. For example, the amount of immunogen composition used in the production of polyclonal antibodies is know to vary upon the nature of the immunogen as well as the animal used for immunization. The production of polyclonal antibodies may be monitored by sampling blood of the immunized animal at various points following immunization. A second, booster injection, may also be given. The process of boosting and titering is repeated until a suitable titer is achieved. All such studies are routine in the art. When a desired level of immunogenicity is obtained, the immunized animal can be bled and the serum isolated and stored, and/or the animal can be used to generate MAbs.

MAbs may be readily prepared through use of well-known techniques, such as those exemplified in U.S. Pat. No. 4,196,265, incorporated herein by reference. Typically, this technique involves immunizing a suitable animal with a selected immunogen composition, in this case, tumor cells with an adjuvant, e.g., MPL, incorporated into the membrane. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are generally preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the MAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5\times10^7$ to $2\times10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler & Milstein (1975; 1976), and those using polyethylene glycol (PEG), such as 37% (v/v) PEG, by Gefter et al. (1977). The use of electrically induced fusion methods is also appropriate (Goding pp. 71–74, 1986).

Fusion procedures usually produce viable hybrids at low frequencies, about $1\times10^{-6}$ to $1\times10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

In the present case, preparations of the desired antigen could be used in the assay. This is exemplified by the ELISA studies in the previous examples where antibodies against various ganglioside antigens were detected. Specifically, sera from mice immunized with melanoma cells containing gangliosides and adjuvants in their membranes were diluted and analyzed for IgM and IgG antibodies using an enzyme-linked immunosorbent assay (ELISA). Depending on which of the anti-ganglioside antibodies to be detected, a microtiter plate was covered with one of the following gangliosides; $GM_3$, $GM_2$, $GD_3$ or $GD_2$. Antibodies recognizing and adhering to any of the gangliosides were detected with anti-IgG or anti-IgM antibodies linked to an enzyme that allowed for a visual means of detection. These assays are ideally suited for use in selecting a suitable hybridoma from a large population.

The selected hybridomas would then be serially diluted and cloned into individual antibody-producing cell lines, which clones can then be propagated indefinitely to provide MAbs. The cell lines may be exploited for MAb production in two basic ways. A sample of the hybridoma can be injected (often into the peritoneal cavity) into a histocompatible animal of the type that was used to provide the somatic and myeloma cells for the original fusion. The injected animal develops tumors secreting the specific Mab produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. MAbs produced by either means may be further purified, if desired, using filtration, centrifugation and various chromatographic methods such as HPLC or affinity chromatography.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Akaza et al., "Expression of antitumor response. Role of attachment and viability of bacillus Calmette-Guerin to bladder cancer cells," *Cancer*, 72(2):558–563, 1993.

Antibodies: A Laboratory Manual, Cold Springs Harbor Laboratory, 1988.

ATCC Catalogue, Catalogue of Cell Lines & Hybridomas, 7th edition, 1992.

Avrameas, "Natural autoantibodies: Self-recognition and physiological autoimmunity," In: *Natural autoantibodies: Their Physiological Role and Regulatory Significance*, Shoenfeld & Isenberg (Eds.), CRC Press, Boca Raton, Fla., pp. 1–14, 1993.

Azuma et al., "Correlation Between Augmented Resistance to Influenza Virus Infection and Histological Changes in Lung of Mice Treated with Trehalose-6,6'-dimycolate," *Journal of Biological Response Modifiers*, 7:473–482, 1988.

Bajorin et al., *Proc. Annu. Meet. Am. Soc. Clin. Oncol.*, 7:A967, 1988.

Baker et al., "Molecular structures that influence the immunomodulatory properties of the lipid A and inner core region oligosaccharides of bacterial lipopolysaccharides," *Infection Immunity*, 62(6):2257–2269, 1994.

Baker et al., "Structural Features That Influence the Ability of Lipid A and Its Analogs To Abolish Expression of Suppressor T Cell Activity," *Infection and Immunity*, 60(7):2694–2701, 1992.

Baker et al., "Ability of Monophosphoryl Lipid A To Augment the Antibody Response of Young Mice," *Infection and Immunity*, 56(12):3064–3066, 1988a.

Baker et al., "Enrichment of Suppressor T Cells by Means of Binding to Monophosphoryl Lipid A," *Infection and Immunity*, 58(3):726–731, 1990.

Baker et al., "Inactivation of Suppressor T-Cell Activity by Nontoxic Monophosphoryl Lipid A," *Infection and Immunity*, 56(5):1076–1083, 1988b.

Bakker et al., "Melanocyte lineage-specific antigen gp100 is recognized by melanoma-derived tumor-infiltrating lymphocytes," *J. Exp. Med.*, 179:1005, 1994.

Banerji et al., "Membrane lipid composition modulates the binding specificity of a monoclonal antibody against liposomes," *Biochim. Biophys. Acta.* 689:319–326, 1982.

Barnd et al., "Specific tumor histocompatibility complex-unrestricted recognition of tumor-associated mucins by human cytotoxic T cells," *Proc. Natl. Acad. Sci. USA*, 86:7159, 1989.

Bartlett & Zbar, *J. Natl. Cancer Inst*, 48:1709, 1972.

Bast et al., "BCG and Cancer," *N. Engl. J. Med.*, 290(25):1413–1420, 1974.

Bennett et al., "Endogenous Production of Cytotoxic Factors in Serum of BCG-Primed Mice by Monophosphoryl Lipid A, a Detoxified Form of Endotoxin," *Journal of Biological Response Modifiers*, 7:65–76, 1988.

Berra et al., *Int. J. Cancer*, 36:363–366, 1985.

Berra et al., *J. Neurochem.*, 40:777–782, 1983.

Bogoch, "Demonstration of serum precipitin to brain gangliosides," *Nature*, 183:392–393, 1960.

Bouchon et al., *Biochem. Internatl.*, 10:531–538, 1985.

Bowness et al., "Clostridium perfringens enterotoxin is a superantigen reactive with human T cell receptors V beta 6.9 and V beta 22," *J. Exp. Med.*, 176(3):893–896, 1992.

Brade et al., "An Artificial Glycoconjugate Containing the Bisphosphorylated Glucosamine Disaccharide Backbone of Lipid A Binds Lipid A Monoclonal Antibodies," *Infection and Immunity*, 61(10):4514–4517, 1993.

Brichard et al., "The tyrosinase gene codes for an antigen recognized by autologous cytolytic T lymphocytes on HLA-A2 melanomas," *J. Exp. Med.* 178:489, 1993.

Brodin et al., "Mouse monoclonal antibodies with specificity for the melanoma-associated ganglioside disialyllactosyl ceramide (GD3) also react with the structural analogue disialylparagloboside," *Biochim. Biophys. Acta.*, 837:349–353, 1985.

Bystryn et al., *Cancer*, 61:1065, 1988.

Burchell et al., *J. Immunol.*, 131(1):508–13, 1983.

Cahan et al., "Identification of a human neuroectodermal tumor antigen (OFA-I-2) as ganglioside GD2," *Proc. Natl. Acad. Sci. USA*, 79:7629–7633, 1982.

Campbell, In: *Monoclonal Antibody Technology, Laboratory Techniques in Biochemistry and Molecular Biology*, Vol. 13, Burden & Von Knippenberg (Eds.), Amsterdam, Elsevier, pp. 75–83, 1984.

Campbell et al., "Intercellular adhesion molecule-1 expression by bladder cancer cells: functional effects," *J. Urol.*, 151(5):1385–1390, 1994.

Carr & Morrison, "A two-step mechanism for the interaction of Re lipopolysaccharide with erythrocyte membranes," *Rev. Infect. Dis.* 6:497–508, 1984.

Carubia et al., *Biochem. Biophys. Res. Commun.*, 120:500–504, 1984.

Chase et al., "Effect of Monophosphoryl Lipid A on Host Resistance to Bacterial Infection," *Infection and Immunity*, 53(3):711–712, 1986.

Chen et al., "Activation of Macrophages From Aging Mice by Detoxified Lipid A," *Journal of Leukocyte Biology*, 49:416–422, 1991.

Cheng et al., "Bacillus Calmette-Gerin interacts with the carboxyl-terminal heparin bindings domain of fibronectin: implications for BCG-mediated antitumor activity," *J. Urol.*, 152(4):1275–1280, 1994.

Cheresh et al., "Disialogangliosides GD2 and GD3 are involved in the attachment of human melanoma and neuroblastoma cells to extracellular matrix proteins," *J. Cell. Biol.*, 102:688–696,1986.

Cheresh & Klier, "Disialoganglioside GD3 distributes preferentially into substrate associated microprocesses on human melanoma cells during their attachment to fibronectin," *J. Cell. Biol.*, 102:1887–1897, 1986.

Cheresh et al., "Disialoganglioside GD3 on human melanoma serves as a relevant target antigen for monoclonal antibody-mediated tumor cytolysis," *Proc. Natl. Acad. Sci. USA*, 82:5155–5159, 1985.

Cheresh et al., "Localization of gangliosides GD2 and GD3 in adhesion plaques and on the surface of human melanoma cells," *Proc. Natl. Acad. Sci. USA*, 81:5767–5771, 1984.

Cheresh et al., "A monoclonal antibody recognizes an O-acetyl sialic acid in a human melanoma-associated ganglioside," *J. Biol. Chem.*, 259:7453–4759, 1984.

Cheung et al., "Detection of neuroblastoma cells in bone marrow using GD2 specific monoclonal antibodies," *J. Clin. Oncol.*, 4:363–369, 1986.

Chu & Sharom, "Gangliosides inhibit T-lymphocyte proliferation by preventing the interaction of interleukin-2 with its cell surface receptors," *Immunology*, 79:10–16, 1993.

Colcher et al., *PNAS*, 78:3199, 1987.

Coulie et al., "A new gene coding for a differentiation antigen recognized by autologous cytologic T lymphocytes on HLA-A2 melanomas," *J. Exp. Med.*, 180:35, 1994.

Dippold et al., "Immunohistochemical localization of ganglioside GD3 in human malignant melanoma, epithelial tumors and normal tissues," *Cancer Res.*, 45:3699–3705, 1985.

Dippold et al., "Inflammatory response at the tumor site after systemic application of monoclonal anti-GD3-ganglioside antibody to patients with malignant melanoma," *Am. Assoc. Cancer Res.*, 978:247, 1984.

Dippold et al., *PNAS*, 77:6115, 1980.

Dresser & Phillips, In: *Immunopotentiation*, CIBA Foundation Symposium 18, Elsevier, Amsterdam, p.3, 1973.

Dwivedi et al., "Plasma lipid-bound sialic acid alterations in neoplastic diseases," *Experientia*, 46:91–94, 1990.

Elder, "Skin Cancer," *Cancer*, 75(1):245–256, 1995.

Elliott et al., "The D-Galactosamine Loaded Mouse and Its Enhanced sensitivity to Lipopolysaccharide and Monophosphoryl Lipid A: A Role for Superoxide," *J. Immunol.*, 10:69–74, 1991.

Euhus et al., *Cancer Immunol Immunother.*, 29:247–254, 1989.

Fawwaz et al., Statutory Invention Registration Patent No. H819, application no. 6-6-5,439, 1990.

Fischer, *Handb. Lipid Res.*, 6:123–234, 1990.

Fitzgerald, "Syphilis vaccine: up-regulation of immunogenicity by cyclophosphamide, Ribi adjuvant, and indomethacin confers significant protection against challenge infection in rabbits," *Vaccine*, 9:265–272, 1991.

Fleischmann et al., "Fibronectin expression on surgical specimens correlated with the response to intravesical bacillus Calmette-Guerin therapy," *J. Urol.*, 149(2):268–271.

Fredman et al., *Neurol. Res.*, 8:123–126, 1986.

Freimer et al., "Gangliosides elicit a T-cell independent antibody response," *J. Autoimmun.* 6:281–289, 1993.

Freudenberg et al., "ELISA for antibodies to Lipid A, Lipopolyasscharides and other hydrophobic antigens," *Infection*, 17:322–324, 1989.

Garg & Subbarao, "Immune Responses of Systemic and Mucosal Lymphoid Organs to Pnu-Immune Vaccine as a Function of Age and the Efficacy of Monophosphoryl Lipid A as an Adjuvant," *Infection and Immunity*, 60(6):2329–2336, 1992.

Gaugler et al., "Human gene MAGE-3 codes for an antigen recognized on a human melanoma by autologous cytolytic T lymphocytes," *J. Exp. Med.*, 179:921, 1994.

Gefter et al., *Somatic Cell Genet.*, 3:231–236, 1977.

Gillard et al., "Antibodies against ganglioside $GT_3$ in the sera of patients with type I Diabetes mellitus," *J. Immunol.* 142:3826–3832, 1989.

Goding, In: *Monoclonal Antibodies: Principles and Practice*, 2d ed., Orlando, Fla., Academic Press, pp. 60–61, 65–66, 71–74, 1986.

Goff et al., Eur. *J. Biochem.*, 130:553–557, 1983.

Grabarek et al., "Endotoxic Lipid A Interaction with Human Platelets," *The Journal of Biological Chemistry*, 265(14):8117–8121, 1990.

Graus et al., "Distribution of the ganglioside GD3 in the human nervous system detected by R24 mouse monoclonal antibody," *Brain Res.* 324:190–194, 1984.

Hachida et al., *Transplant Proc.*, 22:1663–1670, 1990.

Hachida et al., *Transplantation*, 56:479–482, 1993.

Hardings et al., "Effects of pH and polysaccharides on peptide binding to class II major histocompatibility complex molecules," *Proc. Natl. Acad. Sci. USA*, 88:2740–2744, 1991.

Harel et al., *Cancer Res.*, 50:6311, 1990.

Helling et al., "Construction of Immunogenic $GD_3$-conjugate vaccines," *Ann. N.Y. Acad. Sci.* 690:396–397, 1993.

Hellstrom et al., "Strong anti-tumor activities of IgG 3 antibodies to a human melanoma-associated ganglioside," *Proc. Natl. Acad. Sci. USA*, 82:1499–1502, 1985.

Hirabayashi et al., "Reactivity of mouse monoclonal antibody M2590 against B16 melanoma cells with chemically synthesized GM3 ganglioside," *Biochim. Biophys. Acta*, 875:126–128, 1986.

Hirabayashi et al., *Jpn. J. Cancer Res.*, 78:614–620, 1987.

Hirabayashi et al., "Syngeneic monoclonal antibody against melanoma antigen with interspecies cross-reactivity recognize $GM_3$, a prominent ganglioside of B16 melanoma," *Biol. Chem.* 260:13328–13333, 1985.

Hoon et al., "Gangliosides from melanoma immunomodulate response of T-cells to interleukin-2," *Cell Immunol.* 4:1111–1119, 1988.

Horgan, "Total and lipid-bound sialic acid levels in sera from patients with Cancer," *Clin. Chim. Acta.* 118:327–331, 1982.

Houghten et al., "Mouse monoclonal IgG3 antibody detecting GD3 ganglioside: A phase I trial in patients with malignant melanoma," *Proc. Natl. Acad. Sci. USA*, 82:1242–1246, 1985.

Houghton, Alan N., "Cancer Antigens: Immune Recognition of Self and Altered Self," *J. Exp. Med.*, 180:1–4, 1994.

Hraba et al., "The Influence of Monophosphoryl Lipid A (MPL™) on Erythrocyte Autoantibody Formation," *Immunobiol.*, 189:448–456, 1993.

Hunter et al., *Vaccine*, 9:250: 1991.

Irie & Morton, "Regression of cutaneous metastatic melanoma by intralesional injection with human monoclonal antibody to ganglioside GD2," *Proc. Natl. Acad. Sci. USA* 83:8694–8698, 1986.

Irie & Ravindranath, "Gangliosides as targets for monoclonal antibody therapy of cancer," In: *Therapeutic monoclonal antibodies*, Borrebaeck & Larrick (Eds.), Stockton Press, New York, p. 75–94, 1990.

Irie et al., "Melanoma gangliosides and human monoclonal antibody," In: *Human Tumor Antigens and Specific Tumor Therapy*, Metzgar & Mitchell (eds.), Alan R. Liss, Inc., New York, pp. 115–126, 1989.

Irie et al., "Human antibody to OFA-I, a tumor antigen, produced in vitro by Epstein-Barr virus transformed human B-lymphoid cell lines," *Proc. Natl. Acad. Sci. USA*, 79:5666–5670, 1982.

Ishioka et al., "MHC interaction and T cell recognition of carbohydrates and glycopeptides," *J. Immunol.* 148:2446–2451, 1992.

Jackson et al., "Induction of ICAM 1 expression on bladder tumors by BCG immunotherapy," *J. Clin. Pathol.* 47(4):309–312, 1994.

Johnson et al., "Characterization of a nontoxic monophosphoryl lipid A," *Rev. Infect. Dis.* 9:512–516, 1987.

Johnson & Tomai, "A Study of the Cellular and Molecular Mediators of the Adjuvant Action of a Nontoxic Monophosphoryl Lipid A," *Adv. Exp. Med. Biol*, 133:567–579, 1988.

Johnson et al., "Structural Characterization of Monophosphoryl Lipid A Homologs Obtained from *Salmonella Minnesota* Re595 Lipopolysaccharide," *J. Biol. Chem.*, 265(14):8108–8116, 1990.

Johnston and Bystryn, "Effect of Cell Wall Skeleton and Monophosphoryl Lipid A Adjuvant on the Immunogenicity of a Murine B16 Melanoma Vaccine," *Journal of the National Cancer Institute*, 83(17):1240–1245, 1991.

Jones et al., *J Natl Cancer Inst*, 66:249–254, 1981.

Katopodis et al., "Lipid-associated sialic acid test for the detection of human cancer," *Cancer Res.* 42:5270–5275, 1982.

Kawaguchi et al., "Characteristic mode of action of gangliosides in selective modulation of CD4 on human T lymphocytes," *Biochem. Biophys. Res. Commun.* 158:1050–1055, 1989.

Kawakami et al., "Identification of the immunodominant peptides of the Mart-1 human melanoma antigen recognized by the majority of HLA-A2 restricted tumor infiltrating lymphocytes," *J. Exp. Med*. In press, 1994.

Kawakami et al., "Cloning of the gene coding for a shared human melanoma antigen recognized by autologous T cells infiltrating into tumor," *Proc. Natl. Acad. Sci. USA*, 91:3515, 1994.

Kensil et al., *J. Am. Vet. Med. Assoc.*, 199:1423, 1991.

Kloppel et al., "Glycolipid-bound sialic acid in serum: Increased levels in mice and humans bearing mammary carcinomas," *Proc. Natl. Acad. Sci. USA*, 74:3011–3013, 1977.

Kohler & Milstein, *Eur. J. Immunol.*, 6:511–519, 1976.

Kohler & Milstein, *Nature*, 256:495–497, 1975.

Koscielak et al., "Glycolipid antigen and its antibody," *Immunochemistry*, 5:441–455, 1968.

Kovach et al., "Lipid $IV_A$ Inhibits Synthesis and Release of Tumor Necrosis Factor Induced by Lipopolysaccharide in Human Whole Blood Ex Vivo," *J. Exp. Med.*, 172:77–84, 1990.

Kyogashima et al., *Jpn. J. Cancer Res.*, 78:1229–1232, 1987.

Ladisch et al., "Shedding of GD2 ganglioside by human neuroblastoma," *Int. J. Cancer*, 39:73–76, 1987.

Lamm et al., "A randomized trial of intravesical doxorubicin and immunotherapy with bacille Calmette-Guérin for transitional-cell carcinoma of the bladder," *N. Engl. J. Med.*, 325:1205, 1991.

Lengle et al., "Inhibition of the lectin-induced mitogenic response of thymocytes by glycolipids," *Cancer Res.* 39:817–922, 1979.

Liepkalns et al., *J. Neurochem.*, 36:1959–1965, 1981.

Livingston et al., "The Serologic Response to Meth A Sarcoma Vaccines After Cyclophosphamide Treatment is Additionally Increased by Various Adjuvants," *The Journal of Immunology*, 135(2):1505–1509, 1985.

Livingston et al., "Approaches to augmenting immunogenicity of the ganglioside $GM_2$ in mice: purified $GM_2$ is superior to whole cells," *J. Immunol.*, 138:1524–1529, 1987a.

Livingston et al., "Vaccines containing purified $GM_2$ gangliosides elicit $GM_2$ antibodies in melanoma patients," *Proc. Natl. Acad. Sci. USA*, 84:2911–2915, 1987b.

Madonna and Vogel, "Induction of Early-Phase Endotoxin Tolerance in Athymic (Nude) Mice, B-Cell-Deficient (xid) Mice, and Splenectomized Mice," *Infection and Immunity*, 53(3):707–710, 1986.

Masihi et al., "Effects of Nontoxic Lipid A and Endotoxin on Resistance of Mice to *Toxoplasma gondii,*" *Journal of Biological Response Modifiers*, 7:535–539, 1988.

Miller & Esselman, "Modulation of immune response by antigen reactive lymphocytes after cultivation with gangliosides," *J. Immunol.*, 115:839–843, 1975.

Minden, "Shared Antigens Between Animal and Human Tumors and Microorganisms," In: *BCG in Cancer Immunotherapy*, Eds. Lamoureux, Turcotte & Portelance; pp. 73–81, 1976.

Miotti et al., *Cancer Res.*, 65:826, 1985.

Mitchell et al., "Active specific immunotherapy of melanoma: Phase I trial of allogeneic lysates and a novel adjuvant," *Cancer Res.*, 48:5883–5893, 1988.

Mitchell et al., "Active-Specific Immunotherapy for Melanoma," *Journal of Clinical Oncology*, 8(5):856–859, 1990.

Mitchell et al., "Active specific Immunotherapy of melanoma with allogeneic cell lysates: Rationale, results and possible mechanisms of action," *Ann. N.Y. Acad. Sci.*, 690:153–166, 1993.

Miyake et al., *Cancer Res.*, 48:6154–6160, 1988.

Mooney et al., "Bacterial superantigen signaling via HLA class II on human B lymphocytes," *Mol. Immunol.*, 31(9):675–681, 1994.

Morrison et al., "Specific ganglioside binding to receptor sites on T lymphocytes that couple to ganglioside-induced decrease of CD4 expression," *Life Sci.*, 45:1219–1224, 1989.

Morton et al., *Ann. Surg.*, 216:463, 1992.

Morton et al., "Polyvalent Melanoma Vaccine Improves Survival of Patients with Metastatic Melanoma," John Wayne Cancer Institute at Saint John's Hospital and Health Center, Santa Monica, Calif., reprinted from *Specific Immunotherapy of Cancer with Vaccines*, Volume 690 of the *Annals of the New York Academy of Sciences*, 1993.

Morton & Ravindranath, In: *Cancer Medicine*, 3rd edition, Holland et al. (Eds.), Lea & Febiger, Philadelphia, p.967, 1993.

Morton et al., In: *Biological Function of Gangliosides, Progress in Brain Research*, Volume 101, pp 251–275; 1994.

Munjal et al., "Combined measurement and significance of lipid-bound sialic acid and carcinoembryonic antigen in detection of human cancer," *Diagn. Immunol.*, 2:36–43, 1984.

Myers et al., "Monophosphoryl Lipid A Behaves as a T-Cell-Independent Type 1 Carrier for Hapten-Specific Antibody Responses in Mice," *Infection and Immunity*, 63(1):168–174, 1995.

Naiki et al., "Properties of antisera to ganglioside $GM_1$ and $AsialoGM_1$", *J. Immunol.*, 113:84–93, 1974.

Natoli et al., "A murine monoclonal antibody detecting the ganglioside GM2: Characterization of cell surface reactivity," *Cancer Res.*, 46:4116–4120, 1986.

Nudelman et al., "Characterization of a human melanoma-associated ganglioside antigen defined by a monoclonal antibody 4.2,*" J. Biol. Chem.*, 257:12752–12756, 1982.

Odean et al., "Involvement of Gamma Interferon in Antibody Enhancement by Adjuvants," *Infection and Immunity*, 58(2):427–432, 1990.

Pascal et al., "Immunochemical studies on normal and Tay-Sachs' brain gangliosides," *Proc. Soc. Exp. Biol. Med.*, 121:739–743, 1966.

Portoukalian, "Immunoregulatory activity of gangliosides shed by melanoma tumors," In: *Gangliosides and Cancer*, Oettgen (Ed.), New York, VCH Publishers, p. 207–216, 1989.

Portoukalian et al., "Humoral immune response in disease-free advanced melanoma patients after vaccination with melanoma-associated gangliosides," *Int. J. Cancer*, 49:893–899, 1991.

Portoukalian, "Alteration of gangliosides in plasma and red cells of human bearing melanoma tumors," *Biochem. Biophys. Res. Commun.*, 85:916–920, 1978.

Prokazova et al., "Sialylated lactosylceramides. Possible inducers of non-specific immunosuppression and atherosclerotic lesions," *Eur.J.Biochem.*, 171:1–10, 1988.

Pukel et al., "GD3, a prominent ganglioside of human melanoma: Detection and characterization of mouse monoclonal antibody," *J. Exp. Med.*, 155:1133–1147, 1982.

Qureshi et al., "Purification and structural determination of nontoxic lipid A obtained from the Lipopolysaccharide of *Salmonella typhimurium*," *J. Biol. Chem.*, 257:11808–11815, 1985.

Rabinovich et al., "Vaccine Technologies: View to the Future," *Science*, 265:1401–1402, 1994.

Rapport & Graf, "Immunochemical Reactions of Lipids," *Prog. Allergy*, 13:273–331, 1969.

Ravindranath et al., "Human melanoma antigen O-acetylated Ganglioside $GD_3$ is recognized by *Cancer antennarius* lectin," *J. Biol. Chem.*, 263:2079–2086, 1988.

Ravindranath & Irie, In: *Malignant Melanoma: Biology, Diagnosis, and Therapy*, Nathanson (Ed.), Kluwer Acad., Boston, p. 17, 1988.

Ravindranath et al., "An epitope common to gangliosides O-acetyl GD3 and GD3 recognized by antibodies in melanoma patients after active specific immunotherapy," *Cancer Res.*, 49:3891–3897, 1989.

Ravindranath & Morton, "Role of gangliosides in active immunotherapy with melanoma vaccine," *Int. Rev. Immunol.*, 7:303, 1991.

Ravindranath et al., "Ganglioside $GM_3$:$GD_3$ Ratio as an Index for the Management of Melanoma," *Cancer*, 67(12):3029–3035, 1991.

Ravindranath et al., "Efficacy of tumor cell vaccine after incorporating monophosphoryl lipid A (MPL) in tumor cell membranes containing tumor-associated ganglioside," *Experientia*, 50:648–653, 1994a.

Ravindranath et al., "Attachment of Monophosphoryl Lipid A (MPL) to Cells and Liposomes Augments Antibody Response to membrane-bound Gangliosides," *Journal of Autoimmunity*, 7:803–816, 1994b.

Ravindranath et al., "Factors affecting the fine specificity and sensitivity of serum antiganglioside antibodies in ELISA," *J. Immunol. Methods*, 169:257–272, 1994c.

Real et al., "Class I (unique) tumor antigens of human melanoma. Identification of a 90,000 dalton cell surface glycoprotein by autologous antibody," *J. Exp. Med.*, 160:1219, 1984.

Reisfeld et al., *Melanoma Antigens and Antibodies*, p. 317, 1982.

Ribi et al., "Lipid A and immunotherapy," *Rev. Infect. Dis.*, 6:567–572, 1984.

Ribi, "Beneficial modification of the endotoxin molecule," *J. Biol. Resp. Mod.*, 3:1–9, 1984.

Ribi et al., "Modulation of humoral and cell mediated immune responses by a structurally established nontoxic lipid A," In: *Immunobiology and Immunopharmacology of Bacterial Endotoxins*, Szentivanji & Friedman (Eds.), Plenum Press, New York, pp. 407–420, 1986.

Rickman et al., *Lancet* 337:998, 1991.

Rosenberg et al., *N. Engl. J. Med.*, 319:1676, 1988.

Rosenberg et al., *Ann. Surg.*, 210:474, 1989.

Rott et al., "Protection from experimental allergic encephalomyelitis by application of a bacterial superantigen," *Int. Immunol.*, 4(3):347–353, 1992.

Sato et al., "Cytoplasmic membrane-associated protein (CAP) isolated from *Streptococcus pyogenes*: as a new bacterial superantigen," *Microbiol. Immunol.*, 38(2):139–147, 1994.

Schuster et al., "Production of antibodies against phosphocholine, phosphatidylcholine, sphingomyelin, and lipid A by injection of liposomes containing lipid A," *J. Immunol.*, 122:900–905, 1979.

Schwab et al., "Superantigen can reactivate bacterial cell wall-induced arthritis," *J. Immunol.*, 150(9):4151–4159, 1993.

Shafer & Spitznagel, "Sensitivity of *Salmonella typhimurium* to polymorphonuclear granulocyte extracts: Role of lipid A," *Rev. Infect. Dis.*, 6:577–581, 1984.

Shepard et al., *J. Clin. Immunol.*, 11:117–127, 1991.

Sherwin et al., "The production of antisera to gangliosides from human nervous tissue," *Canad. J. Biochem.*, 42:1640–1648, 1964.

Shy et al., "Antibodies to $GM_1$ and $GD_{1b}$ in patients with motor neuron disease with plasma cell dyscrasia," *Ann. Neurol.*, 25:511–518, 1989.

Siddiqui et al., *Cancer Res.*, 44:5262–5265, 1984.

Sidell et al., *Cancer Immunol Immunother*, 7:151–155, 1979.

Sigma Cell Culture, Volume 9, Number 2, 1993.

Stiess & Krüger, "Mammalian Cell Culture Media— Overview and Applications," *The Source* (Sigma Cell Culture Technical and Product News), 9(2):1–8, 1993.

Svennerholm et al., "Tumor gangliosides as targets for active specific immunotherapy of melanoma in man," In: *Biological Function of Gangliosides, Progress in Brain Research*, Volume 101, 1994.

Tai et al., "Ganglioside GM2 as a human tumor antigen (OFA-I-1)," *Proc. Natl. Acad. Sci.*, 80:5392–5396, 1983.

Takada et al., "Molecular and Structural Requirements of a Lipoteichoic Acid from *Enterococcus hirae* ATCC 9790 for Cytokine-Inducing, Antitumor, and Antigenic Activities," *Infection and Immunity*, 63(1):57–65, 1995.

Takahashi et al., *J. Immunol.*, 140:3244, 1988.

Tamauchi et al., *Immunology*, 50:605, 1983.

Tanamoto, "Free Hydroxyl Groups Are Not Required for Endotoxic Activity of Lipid A," *Infection and Immunity*, 62(5):1705–1709, 1994a.

Tanamoto, *FEBS Lett.*, 351:325–329, 1994b.

Tanamoto, "Dissociation of Endotoxic Activities in a Chemically Synthesized Lipid A Precursor after Acetylation," *Infection and Immunity*, 63(2):690–692, 1995.

Tautu et al., "Improved procedure for determination of serum lipid-associated sialic acid: Application for early diagnosis of colorectal cancer," *J. Natl. Cancer Inst.*, 80:1333–1337, 1988.

Thor et al., *Cancer Res.*, 46:3118, 1986.

Thurin et al., "Proton NMR and fast-atom bombardment mass spectrometry analysis of the melanoma-associated ganglioside 9O-acetyl GD3," *J. Biol. Chem.*, 260:14556–14563, 1985.

Tomai et al., "The Adjuvant Properties of a Nontoxic Monophosphoryl Lipid A in Hyporesponsive and Aging Mice," *Journal of Biological Response Modifiers*, 6:99–107, 1987.

Tomai and Johnson, "T Cell and Interferon-γ Involvement in the Adjuvant Action of a Detoxified Endotoxin," *Journal of Biological Response Modifiers*, 8(6):625–643, 1989.

Tsuchida et al., *J. Dermatol.*, 11:129–138, 1984.

Tsuchida et al., "Gangliosides of Human Melanoma: Altered Expression in Vivo and in Vitro," *Cancer Research*, 47:1278–1281, 1987.

Tsuchida et al., "Gangliosides as tumor markers of human melanoma: bio-chemical and immunologic assays," In: *New Horizons of Tumor Immunotherapy*, Eds. Torisu & Yoshida, pp315–325, 1989.

Vadhan-Raj et al., *J. Clin. Oncol.*, 6:1636, 1988.

van der Bruggen et al., "A gene encoding an antigen recognized by cytolytic T lymphocytes on a human melanoma," *Science* (Wash. D.C.), 264:716, 1991.

Verma et al., "Adjuvant Effects of Liposomes Containing Lipid A: Enhancement of Liposomal Antigen Presentation and Recruitment of Macrophages," *Infection and Immunity*, 60(6):2438–2444, 1992.

Vijayasaradhi et al., "The melanoma antigen gp75 is the human homologue of the mouse b (brown) locus gene product," *J. Exp. Med.*, 171:1375, 1990.

Vosika et al., *Cancer Immunol. Immunother.*, 18:107, 1984.

Westrick et al., *Cancer Res.*, 43:5890–5894, 1983b.

Westrick et al., *Biochim. Biophys. Acta*, 750:141–148, 1983a.

Whisler & Yates, "Regulation of lymphocyte responses by human gangliosides. I. Characteristics of inhibitory effects and the induction of impaired activation," *J. Immuunol.*, 125:2106–2112, 1980.

Wilschut, "Preparation and properties of phospholipid vesicles," In: *Methodologie des liposomes appliquee a la pharmacologie et a la biologies cellulaire*, Leserman & Barbet (Eds.), INSERM, Paris, pp. 1–10, 1982.

Yamaguchi et al., "Cell-surface antigens of melanoma recognized by human monoclonal antibodies," *Proc. Natl. Acad. Sci. USA*, 84:2416–2420, 1987.

Yamamoto et al., "In vitro Augmentation of Natural Killer Cell Activity and Production of Interferon-a/β and -γ with Deoxyribonucleic Acid Fraction from *Mycobacterium bovis* BCG," *Jpn. J. Cancer Res.*, 79:866–873, 1988.

Yeh et al., "A cell-surface antigen which is present in the ganglioside fraction and shared by human melanomas," *Int. J. Cancer*, 29:269–275, 1982.

Yin et al., "Effect of Various Adjuvants on the Antibody Response of Mice to Pneumococcal Polysaccharides," *Journal of Biological Response Modifiers*, 8:190–205, 1989.

Yokoyama et al., "Immunochemical studies with gangliosides," *J. Immunol.*, 90:372–380, 1963.

U.S. patent application Ser. No. 07/961/786
U.S. Pat. No. 4,196,265
U.S. Pat. No. 4,435,386
U.S. Pat. No. 4,436,727
U.S. Pat. No. 4,436,728
U.S. Pat. No. 4,505,899
U.S. Pat. No. 4,505,900
U.S. Pat. No. 4,520,019
U.S. Pat. No. 4,562,160
U.S. Pat. No. 4,579,945
U.S. Pat. No. 4,629,722
U.S. Pat. No. 4,808,704
U.S. Pat. No. 4,844,894
U.S. Pat. No. 4,849,509
U.S. Pat. No. 4,851,510
U.S. Pat. No. 4,866,034
U.S. Pat. No. 4,877,611
U.S. Pat. No. 4,950,645
U.S. Pat. No. 4,987,237
U.S. Pat. No. 5,006,470
U.S. Pat. No. 5,009,995
U.S. Pat. No. 5,030,621
U.S. Pat. No. 5,055,559
U.S. Pat. No. 5,091,178
U.S. Pat. No. 5,102,663
U.S. Pat. No. 5,104,652
U.S. Pat. No. 5,126,262
U.S. Pat. No. 5,134,075
U.S. Pat. No. 5,141,864
U.S. Pat. No. 5,194,384
U.S. Pat. No. 5,270,202
U.S. Pat. No. 5,286,643
U.S. Pat. No. 5,286,644
U.S. Pat. No. 5,286,645
U.S. Pat. No. 5,288,628
U.S. Pat. No. 5,290,551
U.S. Pat. No. 5,292,656
U.S. Pat. No. 5,312,620
PCT Patent WO 91/16347.

What is claimed is:

1. A composition comprising a cell that includes an adjuvant non-covalently incorporated into the cell surface membrane or an intracellular compartment of said cell.

2. The composition of claim 1, comprising a cell in which an adjuvant is non-covalently incorporated into the cell surface membrane of said cell.

3. The composition of claim 1, comprising a cell that includes an adjuvant non-covalently incorporated into the cell surface membrane and an adjuvant non-covalently incorporated into an intracellular compartment of said cell.

4. The composition of claim 1, wherein said cell is a human cell.

5. The composition of claim 1, wherein said cell is an erythrocyte.

6. The composition of claim 1, wherein said cell comprises an intracellular antigen.

7. The composition of claim 1, wherein said cell is a tumor cell.

8. The composition of claim 7, wherein said cell is a tumor cell listed in Table 2 or Table 3.

9. The composition of claim 7, wherein said cell is an irradiated tumor cell.

10. The composition of claim 7, wherein said cell is a tumor cell that comprises a tumor-associated intracellular antigen.

11. The composition of claim 7, wherein said cell is a tumor cell that comprises a tumor-associated ganglioside antigen.

12. The composition of claim 7, wherein said cell is a melanoma cell.

13. The composition of claim 12, wherein said cell is a mouse melanoma cell.

14. The composition of claim 13, wherein said cell is the mouse melanoma cell B16.

15. The composition of claim 12, wherein said cell is a human melanoma cell.

16. The composition of claim 15, wherein said cell is the human melanoma cell M27, M18, M14, M111, M22, M7, M102, M108, M16, M104, M109, M25, M24, M10 or M101.

17. The composition of claim 16, wherein said cell is the human melanoma cell M14, M7, M24, M25, M10 or M101.

18. The composition of claim 1, comprising a cell that includes two or more distinct adjuvants non-covalently incorporated into the cell surface membrane or an intracellular compartment of said cell.

19. The composition of claim 1, further comprising a combination of cell types, wherein at least one of which cell types includes an adjuvant non-covalently incorporated into the cell surface membrane or an intracellular compartment of said cell.

20. The composition of claim 1, wherein said adjuvant is an adjuvant listed in Table 1.

21. The composition of claim 20, wherein said adjuvant is lipoteichoic acid (LTA), ribitol technic acid (RTA), glycerol teichoic acid (GTA), hemocyanin from keyhole limpet (KLH), chitin, chitosan, muramyl dipeptide (MDP), threonyl-MDP, a fatty acid derivative of muramyl dipeptide (MTPPE), bacillus Calmette-Guérin (BCG), cell wall skeleton (CWS), trehalose dimycolate, QS21, Quil A or lentinen.

22. The composition of claim 20, wherein said adjuvant is a bacterial superantigen.

23. The composition of claim 20, wherein said adjuvant is of the lipopolysaccharide group of adjuvants.

24. The composition of claim 23, wherein said adjuvant is a detoxified endotoxin.

25. The composition of claim 24, wherein said adjuvant is monophosphoryl lipid A (MPL).

26. The composition of claim 1, comprising a population of cells that includes between about 0.4 ng and about 3.1 ng of cell surface-associated adjuvant per $10^6$ cells, wherein said adjuvant is non-covalently incorporated into the cell surface membrane of said cells.

27. The composition of claim 26, comprising a population of cells that includes between about 1.6 ng and about 2.4 ng of cell surface-associated adjuvant per $10^6$ cells, wherein said adjuvant is non-covalently incorporated into the cell surface membrane of said cells.

28. The composition of claim 1, dispersed in a pharmacologically acceptable formulation.

29. The composition of claim 1, prepared by a method comprising the steps of:
   (a) preparing an adjuvant-suspended culture media composition by sonicating an adjuvant with a culture medium;
   (b) obtaining a cell composition; and
   (c) admixing said adjuvant-suspended culture media composition and said cell composition under conditions effective and for a period of time suitable to allow non-covalent incorporation of the adjuvant into the cell surface membrane or an intracellular compartment of a cell, thereby preparing said composition.

30. The composition of claim 12, prepared by a method comprising the steps of:
   (a) preparing an MPL-suspended culture media composition by sonicating MPL with a culture medium;
   (b) obtaining a melanoma cell composition; and
   (c) admixing said MPL-suspended culture media composition and said melanoma cell composition under conditions effective and for a period of time suitable to allow non-covalent incorporation of the MPL into the cell surface membrane or an intracellular compartment of a cell, thereby preparing said composition.

31. A method of preparing an adjuvant-cell composition in which an adjuvant is non-covalently incorporated into the cell surface membrane or an intracellular compartment of a cell, comprising admixing an adjuvant composition with a cell composition under conditions effective and for a period of time suitable to allow non-covalent incorporation of the adjuvant into a cell surface membrane or an intracellular compartment of a cell, thereby preparing said adjuvant-cell composition.

32. The method of claim 31, comprising the steps of:
   (a) preparing an adjuvant-suspended culture media composition;
   (b) obtaining a cell composition; and
   (c) admixing said adjuvant-suspended culture media composition and said cell composition under conditions effective and for a period of time suitable to allow non-covalent incorporation of the adjuvant into a cell surface membrane or an intracellular compartment of a cell, thereby preparing said adjuvant-cell composition.

33. The method of claim 32, wherein said adjuvant-suspended culture media composition is prepared by sonication.

34. The method of claim 32, wherein said adjuvant-suspended culture media and said cell composition are admixed at a temperature of between about 10° C. and about 40° C.

35. The method of claim 34, wherein said adjuvant-suspended culture media and said cell composition are admixed at a temperature of about 37° C.

36. A method for stimulating an immune response, comprising administering to an animal an immunologically effective amount of an adjuvant-cell composition comprising a cell that includes an adjuvant non-covalently incorporated into the cell surface membrane or an intracellular compartment of said cell.

37. The method of claim 36, wherein a biological sample is obtained from said animal to provide an antibody.

38. The method of claim 37, wherein a blood sample is obtained from said animal to provide a polyclonal antibody.

39. The method of claim 37, wherein a spleen cell sample is obtained from said animal to provide a monoclonal antibody.

40. The method of claim 36, wherein a biological sample is obtained from said animal to provide an antigen-specific T cell.

41. The method of claim 36, wherein said adjuvant-cell composition comprises an erythrocyte that includes an adjuvant non-covalently incorporated into the erythrocyte cell surface membrane or an intracellular compartment of said erythrocyte.

42. The method of claim 36, wherein said adjuvant-cell composition comprises an irradiated tumor cell that includes an adjuvant non-covalently incorporated into the tumor cell surface or an intracellular compartment of said tumor cell.

43. The method of claim 42, wherein said adjuvant-cell composition comprises an irradiated melanoma cell that includes an adjuvant non-covalently incorporated into the melanoma cell surface or an intracellular compartment of said melanoma cell.

44. The method of claim 36, wherein said adjuvant-cell composition comprises a cell that is obtained from an animal, non-covalently incorporated into said adjuvant in vitro, and then administered to the same animal.

45. The method of claim 36, wherein said adjuvant-cell composition comprises an LTA, RTA, GTA, KLH, chitin, chitosan, MDP, threonyl-MDP, MTPPE, BCG, cell wall skeleton (CWS), trehalose dimycolate, QS21, Quil A or lentinen adjuvant in non-covalent association with the cell surface or an intracellular compartment of said cell.

46. The method of claim 36, wherein said adjuvant-cell composition comprises a bacterial superantigen adjuvant in non-covalent association with the cell surface or an intracellular compartment of said cell.

47. The method of claim 36, wherein said adjuvant-cell composition comprises a detoxified endotoxin adjuvant non-covalently incorporated into the cell surface membrane or an intracellular compartment of said cell.

48. The method of claim 36, wherein said animal is a human subject.

49. The method of claim 36, wherein said adjuvant-cell composition comprises a cell that includes an adjuvant non-covalently incorporated into the cell surface membrane and an adjuvant in non-covalent association with an intracellular compartment of said cell.

50. The method of claim 36, wherein said cell that includes an adjuvant non-covalently incorporated into the cell surface membrane or an intracellular compartment is selected from the group consisting of: an adenocarcinoma cell, adenoma cell, astrocytoma cell, bladder tumor cell, brain tumor cell, Burkitt lymphoma cell, breast carcinoma cell, cervical carcinoma cell, colon carcinoma cell, kidney carcinoma cell, liver carcinoma cell, lung carcinoma cell, ovarian carcinoma cell, pancreatic carcinoma cell, prostate carcinoma cell, rectal carcinoma cell, skin carcinoma cell, stomach carcinoma cell, testis carcinoma cell, thyroid carcinoma cell, chondrosarcoma cell, choriocarcinoma cell, fibroma cell, fibrosarcoma cell, glioblastoma cell, glioma cell, hepatoma cell, histiocytoma cell, leiomyoblastoma cell, leiomyosarcoma cell, leukemia cell, lymphoma cell, liposarcoma cell, mammary tumor cell, medulloblastoma cell, myeloma cell, plasmacytoma cell, neuroblastoma cell, neuroglioma cell, osteogenic sarcoma cell, pancreatic tumor cell, pituitary tumor cell, retinoblastoma cell, rhabdomyosarcoma cell, sarcoma cell, testicular tumor cell, thymoma cell or a Wilms' tumor cell.

51. The method of claim 36, wherein said animal has cancer.

52. The method of claim 48, wherein said human has cancer.

53. A composition comprising a cell that includes an adjuvant that is integrated into the cell surface membrane of the cell, non-covalently incorporated into a cell surface membrane protein of the cell, or that is incorporated into an intracellular compartment of the cell.

54. A method for stimulating an immune response, comprising administering to an animal an immunologically effective amount of an adjuvant-cell composition comprising a cell that includes an adjuvant that is integrated into the cell surface membrane of the cell, non-covalently incorporated into a cell surface membrane protein of the cell, or that is incorporated into an intracellular compartment of the cell.

55. The composition of claim 2, comprising a cell that includes an adjuvant that is integrated into the membrane bilayer at the cell surface of said cell.

56. The composition of claim 2, comprising a cell that includes an adjuvant that is non-covalently incorporated into a membrane protein within the cell surface membrane of said cell.

57. A composition comprising a cell that includes an adjuvant that is integrated into the cell surface membrane of the cell or that is non-covalently incorporated into an intracellular compartment of the cell.

58. A method for stimulating an immune response, comprising administering to an animal an immunologically effective amount of an adjuvant-cell composition comprising a cell that includes an adjuvant that is integrated into the cell surface membrane of the cell or that is non-covalently incorporated into an intracellular compartment of the cell.

59. A composition comprising a cell that includes an adjuvant non-covalently incorporated into the cell surface of the cell and an adjuvant non-covalently incorporated into an intracellular compartment of the cell.

60. The composition of claim 59, wherein said cell is a human cell.

61. The composition of claim 59, wherein said cell is a tumor cell.

62. The composition of claim 61, wherein said cell is a tumor cell listed in Table 2 or Table 3.

63. The composition of claim 61, wherein said cell is an irradiated tumor cell.

64. The composition of claim 61, wherein said cell is a tumor cell that comprises a tumor-associated intracellular antigen.

65. The composition of claim 61, wherein said cell is a tumor cell that comprises a tumor-associated ganglioside antigen.

66. The composition of claim 61, wherein said cell is a melanoma cell.

67. The composition of claim 59, wherein said adjuvant is an adjuvant listed in Table 1.

68. The composition of claim 67, wherein said adjuvant is a detoxified endotoxin.

69. The composition of claim 68, wherein said adjuvant is monophosphoryl lipid A (MPL).

70. A method for stimulating an immune response, comprising administering to an animal an immunologically effective amount of an adjuvant-cell composition comprising a cell that includes an adjuvant non-covalently incorporated into the cell surface membrane of the cell and an adjuvant non-covalently incorporated into an intracellular compartment of the cell.

71. A composition comprising a cell that includes an adjuvant non-covalently incorporated into an intracellular compartment of the cell.

72. The composition of claim 71, wherein said cell is a human cell.

73. The composition of claim 71, wherein said cell is a tumor cell that comprises an intracellular tumor-associated antigen.

74. The composition of claim 73, wherein said cell is a tumor cell that comprises an intracellular tumor-associated antigen listed in Table 12.

75. The composition of claim 73, wherein said cell is an irradiated tumor cell.

76. The composition of claim 71, wherein said adjuvant is monophosphoryl lipid A (MPL).

77. A method for stimulating an immune response, comprising administering to an animal an immunologically effective amount of an adjuvant-cell composition comprising a cell that includes an adjuvant non-covalently incorporated into an intracellular compartment of the cell.

78. A composition comprising an erythrocyte that includes an adjuvant non-covalently incorporated into the erythrocyte cell surface or an intracellular compartment of the erythrocyte.

79. The composition of claim 78, wherein said erythrocyte is a human erythrocyte.

80. The composition of claim 78, wherein said erythrocyte is coated with a tumor-associated antigen.

81. The composition of claim 78, wherein said adjuvant is monophosphoryl lipid A (MPL).

82. A method for stimulating an immune response, comprising administering to an animal an immunologically effective amount of an adjuvant-cell composition comprising an erythrocyte that includes an adjuvant non-covalently incorporated into the erythrocyte cell surface membrane or an intracellular compartment of the erythrocyte.

83. A composition comprising a tumor cell that comprises a tumor-associated ganglioside antigen, the cell including an adjuvant non-covalently incorporated into the cell surface membrane or an intracellular compartment of the cell.

84. The composition of claim 83, wherein said tumor cell is an irradiated tumor cell.

85. A m method for stimulating an immune response, comprising administering to an animal an immunologically effective amount of an adjuvant-cell composition comprising a tumor cell that comprises a tumor-associated ganglioside antigen and that includes an adjuvant non-covalently incorporated into the cell surface membrane or an intracellular compartment of the tumor cell.

86. A composition comprising a melanoma cell that includes an adjuvant non-covalently incorporated into the cell surface or an intracellular compartment of the melanoma cell.

87. The composition of claim 86, wherein said melanoma cell is an irradiated melanoma cell.

88. The composition of claim 86, wherein said melanoma cell is a human melanoma cell.

89. The composition of claim 88, wherein said melanoma cell is the human melanoma cell M27, M18, M14, M111, M22, M7, M102, M108, M16, M104, M109, M25, M24, M10 or M101.

90. The composition of claim 89, wherein said melanoma cell is the human melanoma cell M14, M7, M24, M25, M10 or M101.

91. The composition of claim 86, wherein said adjuvant is monophosphoryl lipid A (MPL).

92. A method for stimulating an immune response, comprising administering to an animal an immunologically effective amount of an adjuvant-cell composition comprising a melanoma cell that includes an adjuvant non-covalently incorporated into the cell surface or an intracellular compartment of the melanoma cell.

93. A composition comprising a cell that includes a detoxified endotoxin adjuvant non-covalently incorporated into the cell surface or an intracellular compartment of the cell.

94. The composition of claim 93, wherein said detoxified endotoxin adjuvant is monophosphoryl lipid A (MPL).

95. The composition of claim 94, prepared by a method comprising the steps of:
(a) preparing an MPL-suspended culture media composition by sonicating MPL with a culture medium; and
(b) admixing said MPL-suspended culture media composition with a cell composition under conditions effective and for a period of time suitable to allow incorporation of the MPL into the membrane or an intracellular compartment of a cell, thereby preparing said composition.

96. The composition of claim 93, wherein said cell is a human cell.

97. The composition of claim 93, wherein said cell is a tumor cell.

98. The composition of claim 97, wherein said cell is an irradiated tumor cell.

99. The composition of claim 97, wherein said cell is a tumor cell that comprises a tumor-associated intracellular antigen.

100. The composition of claim 97, wherein said cell is a melanoma cell.

101. A method for stimulating an immune response, comprising administering to an animal an immunologically effective amount of an adjuvant-cell composition comprising a cell that includes a detoxified endotoxin adjuvant non-covalently incorporated into the cell surface membrane or an intracellular compartment of the cell.

102. A composition comprising a cell that includes an adjuvant non-covalently incorporated into the cell surface or an intracellular compartment of the cell, the composition prepared by admixing an adjuvant composition with a cell composition under conditions effective and for a period of time suitable to allow incorporation of the adjuvant into the cell surface membrane or an intracellular compartment of the cell.

103. A method for stimulating an immune response, comprising administering to an animal an immunologically effective amount of an adjuvant-cell composition comprising a cell that includes an adjuvant non-covalently incorporated into the cell surface membrane or an intracellular compartment of the cell, the adjuvant-cell composition prepared by admixing an adjuvant composition with a cell composition under conditions effective and for a period of time suitable to allow incorporation of the adjuvant into the cell surface membrane or an intracellular compartment of the cell.

* * * * *

UNITED STATES PATENT AND TRADEMARK OFFICE
CERTIFICATE OF CORRECTION

PATENT NO. : 6,218,166 B1  
DATED : April 17, 2001  
INVENTOR(S) : Ravindranath et al.

Page 1 of 1

It is certified that error appears in the above-identified patent and that said Letters Patent is hereby corrected as shown below:

<u>Column 84, claim 85,</u>  
Line 54, please delete "A m method" and insert -- A method -- therefor.

Signed and Sealed this

Eighth Day of January, 2002

Attest:

Attesting Officer

JAMES E. ROGAN  
*Director of the United States Patent and Trademark Office*